(12) United States Patent
Lazarus et al.

(10) Patent No.: US 9,624,269 B2
(45) Date of Patent: Apr. 18, 2017

(54) PEPTIDE INHIBITORS OF BACE1

(71) Applicant: GENENTECH, INC., South San Francisco, CA (US)

(72) Inventors: Robert A. Lazarus, South San Francisco, CA (US); Yingnan Zhang, South San Francisco, CA (US); Weiru Wang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/948,173

(22) Filed: Nov. 20, 2015

(65) Prior Publication Data

US 2016/0304563 A1    Oct. 20, 2016

Related U.S. Application Data

(62) Division of application No. 14/351,525, filed as application No. PCT/US2012/059962 on Oct. 12, 2012, now Pat. No. 9,193,766.

(60) Provisional application No. 61/627,573, filed on Oct. 14, 2011.

(51) Int. Cl.
    *C07K 7/08* (2006.01)
    *G01N 33/68* (2006.01)
    *C07K 16/38* (2006.01)
    *A61K 38/00* (2006.01)

(52) U.S. Cl.
    CPC ............... *C07K 7/08* (2013.01); *C07K 16/38* (2013.01); *G01N 33/6896* (2013.01); *A61K 38/00* (2013.01)

(58) Field of Classification Search
    None
    See application file for complete search history.

(56) References Cited

U.S. PATENT DOCUMENTS

| 4,522,811 | A | 6/1985 | Eppstein et al. |
| 4,816,567 | A | 3/1989 | Cabilly et al. |
| 5,112,596 | A | 5/1992 | Malfroy-Camine et al. |
| 5,208,020 | A | 5/1993 | Chari et al. |
| 5,268,164 | A | 12/1993 | Kozarich et al. |
| 5,328,470 | A | 7/1994 | Nabel et al. |
| 5,416,064 | A | 5/1995 | Chari et al. |
| 5,428,130 | A | 6/1995 | Capon et al. |
| 5,506,206 | A | 4/1996 | Kozarich et al. |
| 5,580,723 | A | 12/1996 | Wells et al. |
| 5,635,483 | A | 6/1997 | Pettit et al. |
| 5,686,416 | A | 11/1997 | Kozarich et al. |

(Continued)

FOREIGN PATENT DOCUMENTS

| EP | 0425235 B1 | 9/1996 |
| WO | WO 99/54345 A | 10/1999 |

(Continued)

OTHER PUBLICATIONS

Atwal et al. "A therapeutic antibody targeting BACE1 inhibits anyloid-β production in vivo", Science Translational Med. 3(84):84ra43, 2011.

(Continued)

*Primary Examiner* — Addison D Ault
(74) *Attorney, Agent, or Firm* — Julie Heider; Christopher DeVry; Arnold & Porter Kaye Scholer LLP

(57) ABSTRACT

The invention provides peptide inhibitors of BACE1 that bind to the active site in a noncanonical fashion, and methods of use thereof.

12 Claims, 14 Drawing Sheets
(12 of 14 Drawing Sheet(s) Filed in Color)

(56) References Cited

U.S. PATENT DOCUMENTS

| | | | |
|---|---|---|---|
| 5,712,374 | A | 1/1998 | Kuntsmann et al. |
| 5,714,586 | A | 2/1998 | Kunstmann et al. |
| 5,739,116 | A | 4/1998 | Hamann et al. |
| 5,750,373 | A | 5/1998 | Garrard et al. |
| 5,767,285 | A | 6/1998 | Hamann et al. |
| 5,770,701 | A | 6/1998 | McGahren et al. |
| 5,770,710 | A | 6/1998 | McGahren et al. |
| 5,773,001 | A | 6/1998 | Hamann et al. |
| 5,780,588 | A | 7/1998 | Pettit et al. |
| 5,834,250 | A | 11/1998 | Wells et al. |
| 5,877,296 | A | 3/1999 | Hamann et al. |
| 6,121,416 | A | 9/2000 | Clark et al. |
| 6,630,579 | B2 | 10/2003 | Chari et al. |
| 7,498,298 | B2 | 3/2009 | Doronina et al. |
| 2002/0025313 | A1 | 2/2002 | Micklus et al. |
| 2002/0038086 | A1 | 3/2002 | Hynynen et al. |
| 2003/0083299 | A1 | 5/2003 | Ferguson |
| 2004/0131692 | A1 | 7/2004 | Kreuter et al. |
| 2004/0204354 | A1 | 10/2004 | Nelson et al. |

FOREIGN PATENT DOCUMENTS

| | | |
|---|---|---|
| WO | WO 00/06717 | 2/2000 |
| WO | WO 00/47618 A2 | 8/2000 |
| WO | WO 2004/035606 A | 4/2004 |

OTHER PUBLICATIONS

Barbas et al. "In vitro evolution of a neutralizing human antibody to human immunodeficiency virus type 1 to enhance affinity and broaden strain cross-reactivity", Proc Natl. Acad. Sci. USA 91:3809-3813, 1994.

Chari et al. "Immunoconjugates containing novel maytansinoids: promising anticancer drugs", Cancer Res. 52:127-131, 1992.

Charrier et al. "Second generation of hydroxyethylamine BACE-1 inhibitors: optimizing potency and oral bioavailability", J. Med. Chem. 51:3313-3317, 2008.

Chen et al. "Gene therapy for brain tumors: regression of experimental gliomas by adenovirus-mediated gene transfer in vivo", Proc Natl. Acad. Sci. USA 9(18):3054-3057, 1994.

Crooks et al. "WebLogo: a sequence logo generator", Genome Res. 14(6):1188-1190, 2004.

Database UniProt [Online] "Subname: full=putative uncharacterized protein", XP002697692, Database accession No. A6Q4Z2, Aug. 21, 2007.

Database UniProt [Online] Klotz et al. Nitrosococcus oceni', XP002690392, Database accession No. B6BXD5, Nov. 25, 2008.

Gill et al. "Direct brain infusion of glial cell line-derived neutotrophic factor in Parkinson's disease", Nature Med. 9:589-595, 2003.

Gruniger-Leitch et al. "Substrate and inhibitor profile of BACE (beta-secretase) and comparison with other mammalian aspartic proteases", Journal of Biological Chemistry 277(7):4687-4693, 2002.

Guo et al. "Development of BACE1 inhibitors for Alzheimer's disease", Current Medicinal Chemistry, 13(15):1811-1829, 2006.

Hawkins et al. "Selection of phage antibodies by binding affinity. Mimicking affinity maturation", J Mol. Biol. 226(3):889-896, 1992.

Hinman et al. "Preparation and characterization of monoclonal antibody conjugates of the calicheamicins: a novel and potent family of antitumor antibiotics", Cancer Res. 53(14):3336-3342, 1993.

Hong et al. "Structure of the protease domain of memapsin 2 (beta-secretase) complexed with inhibitor", Science 290:150-153, 2000.

Hussain et al. "Identification of a novel aspartic protease (Asp 2) as beta-secretase", Mol Cell Neurosci. 14:419-427, 1999.

Jackson et al. "In vitro antibody maturation. Improvement of a high affinity, neutralizing antibody against IL-1 beta", J Immunol. 154(7):3310-3319, 1995.

Jones et al. "Replacing the complementarity-determining regions in a human antibody with those from a mouse", Nature 321:522-525, 1986.

Kornacker et al. "An inhibitor binding pocket distinct from the catalytic active site on human beta-APP cleaving enzyme", Biochemistry 44(34):11567-11573, 2005.

Laird et al. "BACE1, a major determinant of selective vulnerability of the brain to amyloid-beta amyloidogenesis, is essential for cognitive, emotional, and synaptic functions", Journal Neuroscience 25:11693-11709, 2005.

Lin et al. "Human aspartic protease memapsin 2 cleaves the beta-secretase site of beta-amyloid precursor protein", Proc. Natl. Acad. Sci. USA 97:1456-1460, 2000.

Lode et al. "Targeted therapy with a novel enediyene antibiotic calicheamicin theta(I)1 effectively suppresses growth and dissemination of liver metastases in a syngeneic model o fmurine neuroblastoma", Cancer Res. 58:2925-2958, 1998.

Luo et al. "Inhibition of BACE1 for therapeutic use in Alzheimer's disease", Int. J Clin. Exp Pathol. 3:618-628, 2010.

McConlogue et al. "Partial reduction of BACE1 has dramatic effects on Alzheimer plaque and synaptic pathology in APP transgenic mice", J Biol Chem. 282:26326-26334, 2007.

McCoy et al. "Phaser crystallographic software", J Appl Crystallogr. 40:658-674, 2007.

Minkeviciene et al. "Memantine improves spatial learning in a transgenic mouse model of Alzheimer's disease", J Pharmacology and Experimental Therapeutics 311(2):677-682, 2001.

Morrison et al. "Chimeric human antibody molecules: mouse antigen-binding domains with human constant region domains", Proc. Natl. Acad. Sci. USA 81:6851-6855, 1984.

Mouri et al. "Oral vaccination with a viral vector containing Abeta c DNA attenuates age-related Abeta accumulation and memory deficits without causing inflammation in a mouse Alzheimer model", FASEB J. 21:2135-2148, 2007.

Nagy et al. "Stability of cytotoxic luteinizing hormone-releasing hormone conjugate (AN-152) containing doxorubicin 14-O-hemiglutarate in mouse and human serum in vitro: implications for the design of preclinical studies", Proc Natl. Acad. Sci. USA 97:829-834, 2000.

Ohno et al. "BACE1 deficiency rescues memory deficits and cholinergic dysfunction in a mouse model of Alzheimer's disease", Neuron 41:27-33, 2004.

Pul et al. "Antibody-based therapy in Alzheimer's disease", Expert Opinion Biol. Ther. 11:343-357, 2011.

Roberds et al. "Bace knockout mice are healthy despite lacking the primary beta-secretase activity in brain: implications for Alzheimer's disease therapeutics", Human Molecular Genetics 10:1317-1324, 2001.

Sandberg et al. "New chemical descriptors relevant for the design of biologically active peptides. A multivariate characterization of 87 amino acids", J. Med. Chem. 41(14):2481-2491, 1998.

Schneider et al. "Sequence logos: a new way to display consensus sequences", Nucleic Acids Research 18(20)6097-6100, 1990.

Silvestri et al. "Boom in the development of non-peptidic beta-secretase (BACE1) inhibitors for the treatment of Alzheimer's disease", Med Res Rev. 29(2):295-338, 2009.

Sinha et al. "Purification and cloning of amyloid precursor protein beta-secretase from human brain", Nature 402:537-540, 1999.

Vassar et al. "Beta-secretase cleavage of Alzheimer's amyloid precursor protein by the transmembrane aspartic protease BACE", Science 286:735-741, 1999.

Vassar et al. "The beta-secretase enzyme BACE in health and Alzheimer's diseas: regulation, cell biology, function, and therapeutic potential", J Neurosci. 29(41):12787-12794, 2009.

Yan et al. "Membrane-anchored aspartyl protase with Alzheimer's disease beta-secretase activity", Nature 402:533-537, 1999.

Yelton et al. "Affinity maturation of the BR96 anti-carcinoma antibody by codon-based mutagenesis", J Immunol. 155:1994-2004, 1995.

Yu et al. "Boosting brain uptake of a therapeutic antibody by reducing its affinity for a transcytosis target", Science Translational Medicine 3:84ra44, 2011.

(56) References Cited

OTHER PUBLICATIONS

Yuede et al. "Anti-dementia drugs and hippocampal-dependent memory in rodents", Behav Pharmacol. 18:347-363, 2007.
Zhou et al. "Inhibition of beta-secretase in vivo via antibody binding to unique loops (D and F) of BACE1", J. Biol. Chem. 286:8677-8687, 2010.
Ziora et al. "Small-sized BACE1 inhibitors", Drugs of the Future 31(1):53-63, 2006.

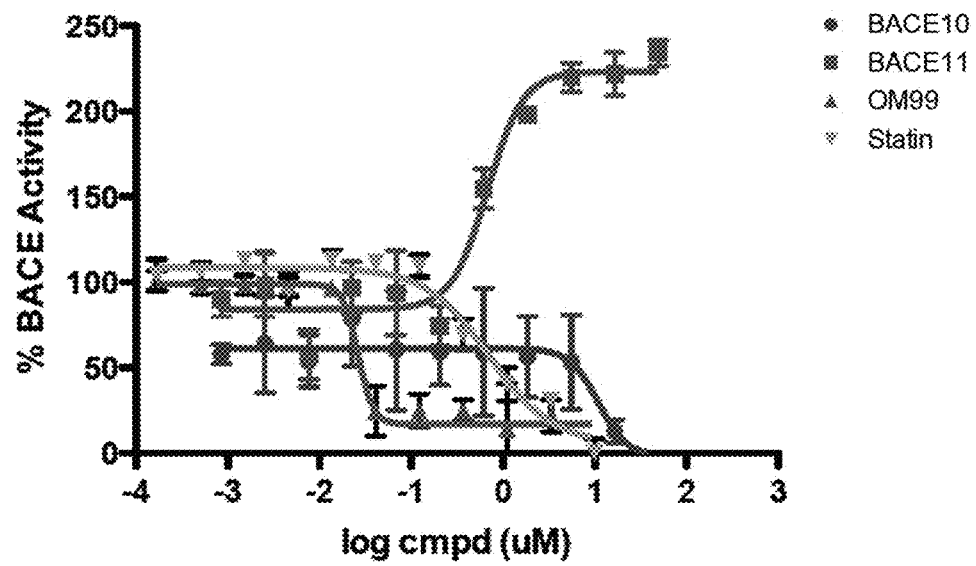

FIG. 2

| Peptide pepID | | | | | | | | | | | | | | | | ELISA | s/n ratio |
|---|---|---|---|---|---|---|---|---|---|---|---|---|---|---|---|---|---|
| BACE017 | N | E | E | H | I | Y | C | R | L | L | G | L | G | C | G | 1.321 | 4.29 |
| BACE018 | K | E | E | S | I | Y | C | R | L | M | G | L | G | C | G | 1.734 | 22.2 |
| | N | M | E | S | V | H | C | R | L | L | G | L | G | C | G | 1.903 | 14.9 |
| | N | E | E | S | I | Y | C | R | L | L | G | L | G | C | G | 1.672 | 12.2 |
| | K | E | E | N | I | Y | C | R | L | L | S | L | G | C | S | 0.934 | 8.5 |
| | N | E | E | S | I | Y | C | R | L | L | G | L | A | C | G | 0.925 | 12.2 |
| | K | E | D | S | M | Y | C | R | L | L | G | L | G | C | G | 1.041 | 12.4 |
| BACE019 | N | E | L | S | P | Y | C | R | L | M | G | L | G | C | D | 1.885 | 20.1 |
| | V | E | E | S | I | Y | C | R | L | L | G | L | G | C | G | 0.779 | 10.4 |
| | I | E | E | S | I | Y | C | R | L | L | G | F | G | C | G | 0.886 | 10.8 |
| | N | G | D | N | M | Y | C | R | L | L | G | L | G | C | E | 0.845 | 15.4 |
| | D | V | E | S | V | Y | C | R | L | L | G | L | G | C | G | 1.022 | 7.9 |
| | N | D | E | S | V | Y | C | R | L | L | G | I | G | C | G | 0.82 | 13.4 |
| BACE020 | N | E | E | S | M | Y | C | R | L | L | G | I | G | C | G | 1.394 | 24.0 |
| | T | E | E | S | L | Y | C | R | L | L | G | V | G | C | G | 2.081 | 15.9 |
| | K | E | E | S | I | H | C | R | L | L | G | L | G | C | G | 1.563 | 8.4 |
| | N | V | E | H | I | H | C | R | L | L | G | L | G | C | G | 1.463 | 14.8 |
| | N | D | D | S | L | Y | C | R | L | L | G | L | G | C | G | 1.379 | 18.4 |
| | Y | E | E | S | I | Y | C | R | L | L | G | I | G | C | G | 1.244 | 10.4 |
| | T | D | E | S | I | Y | C | R | L | L | S | I | A | C | G | 1.145 | 6.7 |
| | K | E | E | S | I | Y | C | R | L | L | G | H | G | C | G | 1.419 | 17.1 |
| | N | E | E | N | M | Y | C | R | L | M | G | I | G | C | G | 0.901 | 14.8 |
| BACE021 | P | E | E | S | L | Y | C | R | L | L | A | L | G | C | G | 2.025 | 22.3 |
| | Y | E | E | S | I | Y | C | R | L | L | G | L | G | C | G | 1.601 | 6.5 |
| | H | E | D | H | L | Y | C | R | L | L | G | I | G | C | G | 1.81 | 15.5 |
| | K | E | E | S | L | Y | C | R | L | L | G | L | G | C | G | 1.492 | 10.7 |
| | T | E | E | S | I | Y | C | R | L | L | G | L | G | C | D | 1.173 | 7.5 |
| | A | E | E | S | I | Y | C | R | L | L | G | L | G | C | G | 0.897 | 12.8 |
| | N | E | V | S | L | Y | C | R | L | L | D | L | G | C | G | 0.957 | 11.0 |
| | N | P | E | N | N | Y | C | R | L | L | N | L | G | C | G | 0.764 | 10.8 |
| | N | D | E | H | M | Y | C | R | L | L | G | L | D | C | N | 1.099 | 8.3 |
| | N | D | E | N | M | Y | C | R | L | L | G | L | G | C | A | 1.23 | 12.9 |

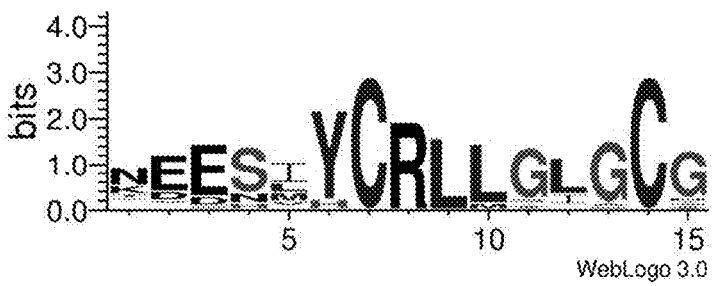

SEQUENCE LISTING

<160> NUMBER OF SEQ ID NOS: 96

<210> SEQ ID NO 1
<211> LENGTH: 501
<212> TYPE: PRT
<213> ORGANISM: Homo sapiens

<400> SEQUENCE: 1

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
        50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
```

-continued

```
              275                 280                 285
Asp Ser Gly Thr Thr Asn Leu Arg Leu Pro Lys Lys Val Phe Glu Ala
    290                 295                 300
Ala Val Lys Ser Ile Lys Ala Ala Ser Ser Thr Glu Lys Phe Pro Asp
305                 310                 315                 320
Gly Phe Trp Leu Gly Glu Gln Leu Val Cys Trp Gln Ala Gly Thr Thr
                325                 330                 335
Pro Trp Asn Ile Phe Pro Val Ile Ser Leu Tyr Leu Met Gly Glu Val
            340                 345                 350
Thr Asn Gln Ser Phe Arg Ile Thr Ile Leu Pro Gln Gln Tyr Leu Arg
        355                 360                 365
Pro Val Glu Asp Val Ala Thr Ser Gln Asp Asp Cys Tyr Lys Phe Ala
    370                 375                 380
Ile Ser Gln Ser Ser Thr Gly Thr Val Met Gly Ala Val Ile Met Glu
385                 390                 395                 400
Gly Phe Tyr Val Val Phe Asp Arg Ala Arg Lys Arg Ile Gly Phe Ala
                405                 410                 415
Val Ser Ala Cys His Val His Asp Glu Phe Arg Thr Ala Ala Val Glu
            420                 425                 430
Gly Pro Phe Val Thr Leu Asp Met Glu Asp Cys Gly Tyr Asn Ile Pro
        435                 440                 445
Gln Thr Asp Glu Ser Thr Leu Met Thr Ile Ala Tyr Val Met Ala Ala
    450                 455                 460
Ile Cys Ala Leu Phe Met Leu Pro Leu Cys Leu Met Val Cys Gln Trp
465                 470                 475                 480
Cys Cys Leu Arg Cys Leu Arg Gln Gln His Asp Asp Phe Ala Asp Asp
                485                 490                 495
Ile Ser Leu Leu Lys
            500

<210> SEQ ID NO 2
<211> LENGTH: 476
<212> TYPE: PRT
<213> ORGANISM: Homo sapiens

<400> SEQUENCE: 2

Met Ala Gln Ala Leu Pro Trp Leu Leu Trp Met Gly Ala Gly Val
1               5                   10                  15
Leu Pro Ala His Gly Thr Gln His Gly Ile Arg Leu Pro Leu Arg Ser
                20                  25                  30
Gly Leu Gly Gly Ala Pro Leu Gly Leu Arg Leu Pro Arg Glu Thr Asp
            35                  40                  45
Glu Glu Pro Glu Glu Pro Gly Arg Arg Gly Ser Phe Val Glu Met Val
    50                  55                  60
Asp Asn Leu Arg Gly Lys Ser Gly Gln Gly Tyr Tyr Val Glu Met Thr
65                  70                  75                  80
Val Gly Ser Pro Pro Gln Thr Leu Asn Ile Leu Val Asp Thr Gly Ser
                85                  90                  95
Ser Asn Phe Ala Val Gly Ala Ala Pro His Pro Phe Leu His Arg Tyr
            100                 105                 110
Tyr Gln Arg Gln Leu Ser Ser Thr Tyr Arg Asp Leu Arg Lys Gly Val
        115                 120                 125
Tyr Val Pro Tyr Thr Gln Gly Lys Trp Glu Gly Glu Leu Gly Thr Asp
    130                 135                 140
```

```
Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Leu Cys Gly
                180                 185                 190

Ala Gly Phe Pro Leu Asn Gln Ser Glu Val Leu Ala Ser Val Gly Gly
                195                 200                 205

Ser Met Ile Ile Gly Gly Ile Asp His Ser Leu Tyr Thr Gly Ser Leu
                210                 215                 220

Trp Tyr Thr Pro Ile Arg Arg Glu Trp Tyr Tyr Glu Val Ile Ile Val
225                 230                 235                 240

Arg Val Glu Ile Asn Gly Gln Asp Leu Lys Met Asp Cys Lys Glu Tyr
                245                 250                 255

Asn Tyr Asp Lys Ser Ile Val Asp Ser Gly Thr Thr Asn Leu Arg Leu
                260                 265                 270

Pro Lys Lys Val Phe Glu Ala Ala Val Lys Ser Ile Lys Ala Ala Ser
                275                 280                 285

Ser Thr Glu Lys Phe Pro Asp Gly Phe Trp Leu Gly Glu Gln Leu Val
                290                 295                 300

Cys Trp Gln Ala Gly Thr Thr Pro Trp Asn Ile Phe Pro Val Ile Ser
305                 310                 315                 320

Leu Tyr Leu Met Gly Glu Val Thr Asn Gln Ser Phe Arg Ile Thr Ile
                325                 330                 335

Leu Pro Gln Gln Tyr Leu Arg Pro Val Glu Asp Val Ala Thr Ser Gln
                340                 345                 350

Asp Asp Cys Tyr Lys Phe Ala Ile Ser Gln Ser Ser Thr Gly Thr Val
                355                 360                 365

Met Gly Ala Val Ile Met Glu Gly Phe Tyr Val Val Phe Asp Arg Ala
                370                 375                 380

Arg Lys Arg Ile Gly Phe Ala Val Ser Ala Cys His Val His Asp Glu
385                 390                 395                 400

Phe Arg Thr Ala Ala Val Glu Gly Pro Phe Val Thr Leu Asp Met Glu
                405                 410                 415

Asp Cys Gly Tyr Asn Ile Pro Gln Thr Asp Glu Ser Thr Leu Met Thr
                420                 425                 430

Ile Ala Tyr Val Met Ala Ala Ile Cys Ala Leu Phe Met Leu Pro Leu
                435                 440                 445

Cys Leu Met Val Cys Gln Trp Cys Cys Leu Arg Cys Leu Arg Gln Gln
450                 455                 460

His Asp Asp Phe Ala Asp Asp Ile Ser Leu Leu Lys
465                 470                 475

<210> SEQ ID NO 3
<211> LENGTH: 457
<212> TYPE: PRT
<213> ORGANISM: Homo sapiens

<400> SEQUENCE: 3

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
                35                  40                  45
```

```
Glu Pro Glu Glu Pro Gly Arg Arg Gly Ser Phe Val Glu Met Val
 50              55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
             85                  90                  95

Ser Asn Phe Ala Val Gly Ala Ala Pro His Pro Phe Leu His Arg Tyr
             100             105             110

Tyr Gln Arg Gln Leu Ser Ser Thr Tyr Arg Asp Leu Arg Lys Gly Val
         115             120             125

Tyr Val Pro Tyr Thr Gln Gly Lys Trp Glu Gly Glu Leu Gly Thr Asp
     130             135             140

Leu Pro Asp Asp Ser Leu Glu Pro Phe Phe Asp Ser Leu Val Lys Gln
145             150             155                 160

Thr His Val Pro Asn Leu Phe Ser Leu Gln Leu Cys Gly Ala Gly Phe
                 165             170             175

Pro Leu Asn Gln Ser Glu Val Leu Ala Ser Val Gly Gly Ser Met Ile
             180             185             190

Ile Gly Gly Ile Asp His Ser Leu Tyr Thr Gly Ser Leu Trp Tyr Thr
         195             200             205

Pro Ile Arg Arg Glu Trp Tyr Tyr Glu Val Ile Ile Val Arg Val Glu
     210             215             220

Ile Asn Gly Gln Asp Leu Lys Met Asp Cys Lys Glu Tyr Asn Tyr Asp
225             230             235                 240

Lys Ser Ile Val Asp Ser Gly Thr Thr Asn Leu Arg Leu Pro Lys Lys
                 245             250             255

Val Phe Glu Ala Ala Val Lys Ser Ile Lys Ala Ala Ser Ser Thr Glu
             260             265             270

Lys Phe Pro Asp Gly Phe Trp Leu Gly Glu Gln Leu Val Cys Trp Gln
         275             280             285

Ala Gly Thr Thr Pro Trp Asn Ile Phe Pro Val Ile Ser Leu Tyr Leu
     290             295             300

Met Gly Glu Val Thr Asn Gln Ser Phe Arg Ile Thr Ile Leu Pro Gln
305             310             315                 320

Gln Tyr Leu Arg Pro Val Glu Asp Val Ala Thr Ser Gln Asp Asp Cys
                 325             330             335

Tyr Lys Phe Ala Ile Ser Gln Ser Ser Thr Gly Thr Val Met Gly Ala
             340             345             350

Val Ile Met Glu Gly Phe Tyr Val Val Phe Asp Arg Ala Arg Lys Arg
         355             360             365

Ile Gly Phe Ala Val Ser Ala Cys His Val His Asp Glu Phe Arg Thr
     370             375             380

Ala Ala Val Glu Gly Pro Phe Val Thr Leu Asp Met Glu Asp Cys Gly
385             390             395                 400

Tyr Asn Ile Pro Gln Thr Asp Glu Ser Thr Leu Met Thr Ile Ala Tyr
                 405             410             415

Val Met Ala Ala Ile Cys Ala Leu Phe Met Leu Pro Leu Cys Leu Met
             420             425             430

Val Cys Gln Trp Cys Cys Leu Arg Cys Leu Arg Gln Gln His Asp Asp
         435             440             445

Phe Ala Asp Asp Ile Ser Leu Leu Lys
     450             455
```

<210> SEQ ID NO 4
<211> LENGTH: 432
<212> TYPE: PRT
<213> ORGANISM: Homo sapiens

<400> SEQUENCE: 4

```
Met Ala Gln Ala Leu Pro Trp Leu Leu Leu Trp Met Gly Ala Gly Val
 1               5                  10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Leu Cys Gly Ala Gly Phe Pro Leu Asn Gln Ser Glu Val Leu Ala
145                 150                 155                 160

Ser Val Gly Gly Ser Met Ile Ile Gly Gly Ile Asp His Ser Leu Tyr
                165                 170                 175

Thr Gly Ser Leu Trp Tyr Thr Pro Ile Arg Arg Glu Trp Tyr Tyr Glu
            180                 185                 190

Val Ile Ile Val Arg Val Glu Ile Asn Gly Gln Asp Leu Lys Met Asp
        195                 200                 205

Cys Lys Glu Tyr Asn Tyr Asp Lys Ser Ile Val Asp Ser Gly Thr Thr
    210                 215                 220

Asn Leu Arg Leu Pro Lys Lys Val Phe Glu Ala Ala Val Lys Ser Ile
225                 230                 235                 240

Lys Ala Ala Ser Ser Thr Glu Lys Phe Pro Asp Gly Phe Trp Leu Gly
                245                 250                 255

Glu Gln Leu Val Cys Trp Gln Ala Gly Thr Thr Pro Trp Asn Ile Phe
            260                 265                 270

Pro Val Ile Ser Leu Tyr Leu Met Gly Glu Val Thr Asn Gln Ser Phe
        275                 280                 285

Arg Ile Thr Ile Leu Pro Gln Gln Tyr Leu Arg Pro Val Glu Asp Val
    290                 295                 300

Ala Thr Ser Gln Asp Asp Cys Tyr Lys Phe Ala Ile Ser Gln Ser Ser
305                 310                 315                 320

Thr Gly Thr Val Met Gly Ala Val Ile Met Glu Gly Phe Tyr Val Val
                325                 330                 335

Phe Asp Arg Ala Arg Lys Arg Ile Gly Phe Ala Val Ser Ala Cys His
            340                 345                 350

Val His Asp Glu Phe Arg Thr Ala Ala Val Glu Gly Pro Phe Val Thr
        355                 360                 365

Leu Asp Met Glu Asp Cys Gly Tyr Asn Ile Pro Gln Thr Asp Glu Ser
    370                 375                 380
```

```
Thr Leu Met Thr Ile Ala Tyr Val Met Ala Ala Ile Cys Ala Leu Phe
385                 390                 395                 400

Met Leu Pro Leu Cys Leu Met Val Cys Gln Trp Cys Cys Leu Arg Cys
                405                 410                 415

Leu Arg Gln Gln His Asp Asp Phe Ala Asp Asp Ile Ser Leu Leu Lys
            420                 425                 430

<210> SEQ ID NO 5
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Lys Thr Glu Glu Ile Ser Glu Val Asn Leu Asp Ala Glu Phe Arg His
1               5                   10                  15

Asp Ser Gly Tyr Glu Val His His Gln Lys Leu
            20                  25

<210> SEQ ID NO 6
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: misc_feature
<222> LOCATION: (1)..(1)
<223> OTHER INFORMATION: /note="Residue given in the sequence has no
      preference with respect to the annotation for said position"
<220> FEATURE:
<221> NAME/KEY: VARIANT
<222> LOCATION: (3)..(3)
<223> OTHER INFORMATION: /replace="Leu" or "Ile" or "Val"
<220> FEATURE:
<221> NAME/KEY: misc_feature
<222> LOCATION: (3)..(3)
<223> OTHER INFORMATION: /note="Residue given in the sequence has no
      preference with respect to those in the annotation for said
      position"
<220> FEATURE:
<221> NAME/KEY: VARIANT
<222> LOCATION: (8)..(8)
<223> OTHER INFORMATION: /replace="Met"
<220> FEATURE:
<221> NAME/KEY: VARIANT
<222> LOCATION: (9)..(9)
<223> OTHER INFORMATION: /replace="Ser" or "Ala"
<220> FEATURE:
<221> NAME/KEY: VARIANT
<222> LOCATION: (10)..(10)
<223> OTHER INFORMATION: /replace="Ile" or "Val"
<220> FEATURE:
<221> NAME/KEY: VARIANT
<222> LOCATION: (11)..(11)
<223> OTHER INFORMATION: /replace="Ala"
<220> FEATURE:
<221> NAME/KEY: misc_feature
<222> LOCATION: (8)..(11)
<223> OTHER INFORMATION: /note="Residues given in the sequence have
      no preference with respect to those in the annotations for said
      positions"
<220> FEATURE:
```

```
<221> NAME/KEY: VARIANT
<222> LOCATION: (13)..(13)
<223> OTHER INFORMATION: /replace="Asp" or "Glu" or " "
<220> FEATURE:
<221> NAME/KEY: misc_feature
<222> LOCATION: (13)..(13)
<223> OTHER INFORMATION: /note="Residue given in the sequence has no
      preference with respect to those in the annotation for said
      position"

<400> SEQUENCE: 6

Glu Ser Met Tyr Cys Arg Leu Leu Gly Leu Gly Cys Gly
1               5                   10

<210> SEQ ID NO 7
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: misc_feature
<222> LOCATION: (1)..(1)
<223> OTHER INFORMATION: /note="Residue given in the sequence has no
      preference with respect to the annotation for said position"
<220> FEATURE:
<221> NAME/KEY: VARIANT
<222> LOCATION: (3)..(3)
<223> OTHER INFORMATION: /replace="Leu" or "Ile" or "Val"
<220> FEATURE:
<221> NAME/KEY: misc_feature
<222> LOCATION: (3)..(3)
<223> OTHER INFORMATION: /note="Residue given in the sequence has no
      preference with respect to those in the annotation for said
      position"
<220> FEATURE:
<221> NAME/KEY: VARIANT
<222> LOCATION: (8)..(8)
<223> OTHER INFORMATION: /replace="Met"
<220> FEATURE:
<221> NAME/KEY: VARIANT
<222> LOCATION: (9)..(9)
<223> OTHER INFORMATION: /replace="Ser" or "Ala"
<220> FEATURE:
<221> NAME/KEY: VARIANT
<222> LOCATION: (10)..(10)
<223> OTHER INFORMATION: /replace="Ile" or "Val"
<220> FEATURE:
<221> NAME/KEY: VARIANT
<222> LOCATION: (11)..(11)
<223> OTHER INFORMATION: /replace="Ala"
<220> FEATURE:
<221> NAME/KEY: misc_feature
<222> LOCATION: (8)..(11)
<223> OTHER INFORMATION: /note="Residues given in the sequence have
      no preference with respect to those in the annotations for said
      positions"

<400> SEQUENCE: 7

Glu Ser Met Tyr Cys Arg Leu Leu Gly Leu Gly Cys
1               5                   10

<210> SEQ ID NO 8
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
```

```
         Synthetic peptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: misc_feature
<222> LOCATION: (1)..(1)
<223> OTHER INFORMATION: /note="Residue given in the sequence has no
      preference with respect to the annotation for said position"
<220> FEATURE:
<221> NAME/KEY: VARIANT
<222> LOCATION: (3)..(3)
<223> OTHER INFORMATION: /replace="Leu" or "Ile" or "Val"
<220> FEATURE:
<221> NAME/KEY: misc_feature
<222> LOCATION: (3)..(3)
<223> OTHER INFORMATION: /note="Residue given in the sequence has no
      preference with respect to those in the annotation for said
      position"
<220> FEATURE:
<221> NAME/KEY: VARIANT
<222> LOCATION: (8)..(8)
<223> OTHER INFORMATION: /replace="Met"
<220> FEATURE:
<221> NAME/KEY: VARIANT
<222> LOCATION: (9)..(9)
<223> OTHER INFORMATION: /replace="Ser" or "Ala"
<220> FEATURE:
<221> NAME/KEY: VARIANT
<222> LOCATION: (10)..(10)
<223> OTHER INFORMATION: /replace="Ile" or "Val"
<220> FEATURE:
<221> NAME/KEY: VARIANT
<222> LOCATION: (11)..(11)
<223> OTHER INFORMATION: /replace="Ala"
<220> FEATURE:
<221> NAME/KEY: misc_feature
<222> LOCATION: (8)..(11)
<223> OTHER INFORMATION: /note="Residues given in the sequence have
      no preference with respect to those in the annotations for said
      positions"
<220> FEATURE:
<221> NAME/KEY: VARIANT
<222> LOCATION: (13)..(13)
<223> OTHER INFORMATION: /replace="Asp" or "Glu"
<220> FEATURE:
<221> NAME/KEY: misc_feature
<222> LOCATION: (13)..(13)
<223> OTHER INFORMATION: /note="Residue given in the sequence has no
      preference with respect to those in the annotation for said
      position"

<400> SEQUENCE: 8

Glu Ser Met Tyr Cys Arg Leu Leu Gly Leu Gly Cys Gly
1               5                   10

<210> SEQ ID NO 9
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: misc_feature
<222> LOCATION: (1)..(1)
<223> OTHER INFORMATION: /note="Residue given in the sequence has no
      preference with respect to the annotation for said position"
<220> FEATURE:
<221> NAME/KEY: VARIANT
<222> LOCATION: (3)..(3)
```

```
<223> OTHER INFORMATION: /replace="Leu" or "Ile" or "Val"
<220> FEATURE:
<221> NAME/KEY: misc_feature
<222> LOCATION: (3)..(3)
<223> OTHER INFORMATION: /note="Residue given in the sequence has no
      preference with respect to those in the annotation for said
      position"
<220> FEATURE:
<221> NAME/KEY: VARIANT
<222> LOCATION: (9)..(9)
<223> OTHER INFORMATION: /replace="Ser" or "Ala"
<220> FEATURE:
<221> NAME/KEY: VARIANT
<222> LOCATION: (10)..(10)
<223> OTHER INFORMATION: /replace="Ile" or "Val"
<220> FEATURE:
<221> NAME/KEY: VARIANT
<222> LOCATION: (11)..(11)
<223> OTHER INFORMATION: /replace="Ala"
<220> FEATURE:
<221> NAME/KEY: misc_feature
<222> LOCATION: (9)..(11)
<223> OTHER INFORMATION: /note="Residues given in the sequence have
      no preference with respect to those in the annotations for said
      positions"
<220> FEATURE:
<221> NAME/KEY: VARIANT
<222> LOCATION: (13)..(13)
<223> OTHER INFORMATION: /replace="Asp" or "Glu" or " "
<220> FEATURE:
<221> NAME/KEY: misc_feature
<222> LOCATION: (13)..(13)
<223> OTHER INFORMATION: /note="Residue given in the sequence has no
      preference with respect to those in the annotation for said
      position"

<400> SEQUENCE: 9

Glu Ser Met Tyr Cys Arg Leu Leu Gly Leu Gly Cys Gly
1               5                   10

<210> SEQ ID NO 10
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: misc_feature
<222> LOCATION: (1)..(1)
<223> OTHER INFORMATION: /note="Residue given in the sequence has no
      preference with respect to the annotation for said position"
<220> FEATURE:
<221> NAME/KEY: VARIANT
<222> LOCATION: (3)..(3)
<223> OTHER INFORMATION: /replace="Leu" or "Ile" or "Val"
<220> FEATURE:
<221> NAME/KEY: misc_feature
<222> LOCATION: (3)..(3)
<223> OTHER INFORMATION: /note="Residue given in the sequence has no
      preference with respect to those in the annotation for said
      position"
<220> FEATURE:
<221> NAME/KEY: VARIANT
<222> LOCATION: (8)..(8)
<223> OTHER INFORMATION: /replace="Met"
<220> FEATURE:
<221> NAME/KEY: misc_feature
<222> LOCATION: (8)..(8)
<223> OTHER INFORMATION: /note="Residue given in the sequence has no
      preference with respect to the annotation for said position"
<220> FEATURE:
```

```
<221> NAME/KEY: VARIANT
<222> LOCATION: (10)..(10)
<223> OTHER INFORMATION: /replace="Ile" or "Val"
<220> FEATURE:
<221> NAME/KEY: VARIANT
<222> LOCATION: (11)..(11)
<223> OTHER INFORMATION: /replace="Ala"
<220> FEATURE:
<221> NAME/KEY: misc_feature
<222> LOCATION: (10)..(11)
<223> OTHER INFORMATION: /note="Residues given in the sequence have
      no preference with respect to those in the annotations for said
      positions"
<220> FEATURE:
<221> NAME/KEY: VARIANT
<222> LOCATION: (13)..(13)
<223> OTHER INFORMATION: /replace="Asp" or "Glu" or " "
<220> FEATURE:
<221> NAME/KEY: misc_feature
<222> LOCATION: (13)..(13)
<223> OTHER INFORMATION: /note="Residue given in the sequence has no
      preference with respect to those in the annotation for said
      position"

<400> SEQUENCE: 10

Glu Ser Met Tyr Cys Arg Leu Leu Gly Leu Gly Cys Gly
1               5                   10

<210> SEQ ID NO 11
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: misc_feature
<222> LOCATION: (1)..(1)
<223> OTHER INFORMATION: /note="Residue given in the sequence has no
      preference with respect to the annotation for said position"
<220> FEATURE:
<221> NAME/KEY: VARIANT
<222> LOCATION: (3)..(3)
<223> OTHER INFORMATION: /replace="Leu" or "Ile" or "Val"
<220> FEATURE:
<221> NAME/KEY: misc_feature
<222> LOCATION: (3)..(3)
<223> OTHER INFORMATION: /note="Residue given in the sequence has no
      preference with respect to those in the annotation for said
      position"
<220> FEATURE:
<221> NAME/KEY: VARIANT
<222> LOCATION: (8)..(8)
<223> OTHER INFORMATION: /replace="Met"
<220> FEATURE:
<221> NAME/KEY: VARIANT
<222> LOCATION: (9)..(9)
<223> OTHER INFORMATION: /replace="Ser" or "Ala"
<220> FEATURE:
<221> NAME/KEY: misc_feature
<222> LOCATION: (8)..(9)
<223> OTHER INFORMATION: /note="Residues given in the sequence have
      no preference with respect to those in the annotations for said
      positions"
<220> FEATURE:
<221> NAME/KEY: VARIANT
<222> LOCATION: (11)..(11)
<223> OTHER INFORMATION: /replace="Ala"
<220> FEATURE:
<221> NAME/KEY: misc_feature
<222> LOCATION: (11)..(11)
<223> OTHER INFORMATION: /note="Residue given in the sequence has no
```

-continued

```
      preference with respect to the annotation for said position"
<220> FEATURE:
<221> NAME/KEY: VARIANT
<222> LOCATION: (13)..(13)
<223> OTHER INFORMATION: /replace="Asp" or "Glu" or " "
<220> FEATURE:
<221> NAME/KEY: misc_feature
<222> LOCATION: (13)..(13)
<223> OTHER INFORMATION: /note="Residue given in the sequence has no
      preference with respect to those in the annotation for said
      position"

<400> SEQUENCE: 11

Glu Ser Met Tyr Cys Arg Leu Leu Gly Ile Gly Cys Gly
1               5                   10

<210> SEQ ID NO 12
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: misc_feature
<222> LOCATION: (1)..(1)
<223> OTHER INFORMATION: /note="Residue given in the sequence has no
      preference with respect to the annotation for said position"
<220> FEATURE:
<221> NAME/KEY: VARIANT
<222> LOCATION: (3)..(3)
<223> OTHER INFORMATION: /replace="Leu" or "Ile" or "Val"
<220> FEATURE:
<221> NAME/KEY: misc_feature
<222> LOCATION: (3)..(3)
<223> OTHER INFORMATION: /note="Residue given in the sequence has no
      preference with respect to those in the annotation for said
      position"
<220> FEATURE:
<221> NAME/KEY: VARIANT
<222> LOCATION: (8)..(8)
<223> OTHER INFORMATION: /replace="Met"
<220> FEATURE:
<221> NAME/KEY: VARIANT
<222> LOCATION: (9)..(9)
<223> OTHER INFORMATION: /replace="Ser" or "Ala"
<220> FEATURE:
<221> NAME/KEY: VARIANT
<222> LOCATION: (10)..(10)
<223> OTHER INFORMATION: /replace="Ile" or "Val"
<220> FEATURE:
<221> NAME/KEY: misc_feature
<222> LOCATION: (8)..(10)
<223> OTHER INFORMATION: /note="Residues given in the sequence have
      no preference with respect to those in the annotations for said
      positions"
<220> FEATURE:
<221> NAME/KEY: VARIANT
<222> LOCATION: (13)..(13)
<223> OTHER INFORMATION: /replace="Asp" or "Glu" or " "
<220> FEATURE:
<221> NAME/KEY: misc_feature
<222> LOCATION: (13)..(13)
<223> OTHER INFORMATION: /note="Residue given in the sequence has no
      preference with respect to the annotation for said
      position"

<400> SEQUENCE: 12

Glu Ser Met Tyr Cys Arg Leu Leu Gly Leu Gly Cys Gly
1               5                   10
```

```
<210> SEQ ID NO 13
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Asp"
<220> FEATURE:
<221> NAME/KEY: misc_feature
<222> LOCATION: (1)..(1)
<223> OTHER INFORMATION: /note="Residue given in the sequence has no
      preference with respect to the annotation for said position"
<220> FEATURE:
<221> NAME/KEY: VARIANT
<222> LOCATION: (3)..(3)
<223> OTHER INFORMATION: /replace="Leu" or "Ile" or "Val"
<220> FEATURE:
<221> NAME/KEY: misc_feature
<222> LOCATION: (3)..(3)
<223> OTHER INFORMATION: /note="Residue given in the sequence has no
      preference with respect to those in the annotation for said
      position"
<220> FEATURE:
<221> NAME/KEY: VARIANT
<222> LOCATION: (8)..(8)
<223> OTHER INFORMATION: /replace="Met"
<220> FEATURE:
<221> NAME/KEY: VARIANT
<222> LOCATION: (9)..(9)
<223> OTHER INFORMATION: /replace="Ser" or "Ala"
<220> FEATURE:
<221> NAME/KEY: VARIANT
<222> LOCATION: (10)..(10)
<223> OTHER INFORMATION: /replace="Ile" or "Val"
<220> FEATURE:
<221> NAME/KEY: VARIANT
<222> LOCATION: (11)..(11)
<223> OTHER INFORMATION: /replace="Ala"
<220> FEATURE:
<221> NAME/KEY: misc_feature
<222> LOCATION: (8)..(11)
<223> OTHER INFORMATION: /note="Residues given in the sequence has no
      preference with respect to those in the annotations for said
      positions"

<400> SEQUENCE: 13

Glu Ser Met Tyr Cys Arg Leu Leu Gly Leu Gly Cys Gly
1               5                   10

<210> SEQ ID NO 14
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Lys Glu Glu Ser Ile Tyr Cys Arg Leu Met Gly Leu Gly Cys Gly
1               5                   10                  15

<210> SEQ ID NO 15
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                            Synthetic peptide"

<400> SEQUENCE: 15

Asn Glu Leu Ser Pro Tyr Cys Arg Leu Met Gly Leu Gly Cys Asp
1               5                   10                  15

<210> SEQ ID NO 16
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Asn Glu Glu Ser Met Tyr Cys Arg Leu Leu Gly Ile Gly Cys Gly
1               5                   10                  15

<210> SEQ ID NO 17
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Pro Glu Glu Ser Leu Tyr Cys Arg Leu Leu Ala Leu Gly Cys Gly
1               5                   10                  15

<210> SEQ ID NO 18
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ser Met Tyr Cys Arg Leu Leu Gly Ile Gly Cys Gly
1               5                   10

<210> SEQ ID NO 19
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Glu Ser Met Tyr Cys Arg Leu Leu Gly Ile Gly Cys Gly
1               5                   10

<210> SEQ ID NO 20
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20
```

Lys Thr Glu Glu Ile Ser Glu Val Asn Leu Asp Ala Glu Phe Arg Trp
1               5                   10                  15

Lys Lys

<210> SEQ ID NO 21
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Gly Pro Tyr Phe Ile Glu Tyr Met Ser Ala Val
1               5                   10

<210> SEQ ID NO 22
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asn Leu Thr Thr Tyr Pro Tyr Phe Ile Pro Leu Pro
1               5                   10

<210> SEQ ID NO 23
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ala Leu Tyr Pro Tyr Phe Leu Pro Ile Ser Ala Lys
1               5                   10

<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Tyr Pro Tyr Phe Ile Pro Leu
1               5

<210> SEQ ID NO 25
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ser Gly Cys Leu Asp Tyr Pro Cys Phe Val Pro Ile Ser
1               5                   10

```
<210> SEQ ID NO 26
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asn Glu Glu His Ile Tyr Cys Arg Leu Leu Gly Leu Gly Cys Gly
1               5                   10                  15

<210> SEQ ID NO 27
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Lys Glu Glu Ser Ile Tyr Ser Arg Leu Met Gly Leu Gly Ser Gly
1               5                   10                  15

<210> SEQ ID NO 28
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Asn Glu Leu Ser Pro Tyr Ser Arg Leu Met Gly Leu Gly Ser Asp
1               5                   10                  15

<210> SEQ ID NO 29
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asn Glu Glu Ser Met Tyr Ser Arg Leu Leu Gly Ile Gly Ser Gly
1               5                   10                  15

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Pro Glu Glu Ser Leu Tyr Ser Arg Leu Leu Ala Leu Gly Ser Gly
1               5                   10                  15

<210> SEQ ID NO 31
<211> LENGTH: 14
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Glu Glu Ser Met Tyr Cys Arg Leu Leu Gly Ile Gly Cys Gly
1               5                   10

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Met Tyr Cys Arg Leu Leu Gly Ile Gly Cys Gly
1               5                   10

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Tyr Cys Arg Leu Leu Gly Ile Gly Cys Gly
1               5                   10

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Cys Arg Leu Leu Gly Ile Gly Cys Gly
1               5

<210> SEQ ID NO 35
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ala Glu Glu Ser Met Tyr Cys Arg Leu Leu Gly Ile Gly Cys Gly
1               5                   10                  15

<210> SEQ ID NO 36
<211> LENGTH: 15
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 36

Asn Ala Glu Ser Met Tyr Cys Arg Leu Leu Gly Ile Gly Cys Gly
1               5                   10                  15

<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Asn Glu Ala Ser Met Tyr Cys Arg Leu Leu Gly Ile Gly Cys Gly
1               5                   10                  15

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Asn Glu Glu Ala Met Tyr Cys Arg Leu Leu Gly Ile Gly Cys Gly
1               5                   10                  15

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Asn Glu Glu Ser Ala Tyr Cys Arg Leu Leu Gly Ile Gly Cys Gly
1               5                   10                  15

<210> SEQ ID NO 40
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Asn Glu Glu Ser Met Ala Cys Arg Leu Leu Gly Ile Gly Cys Gly
1               5                   10                  15

<210> SEQ ID NO 41
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41
```

Asn Glu Glu Ser Met Tyr Cys Ala Leu Leu Gly Ile Gly Cys Gly
1               5                   10                  15

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Asn Glu Glu Ser Met Tyr Cys Arg Ala Leu Gly Ile Gly Cys Gly
1               5                   10                  15

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Asn Glu Glu Ser Met Tyr Cys Arg Leu Ala Gly Ile Gly Cys Gly
1               5                   10                  15

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Asn Glu Glu Ser Met Tyr Cys Arg Leu Leu Ala Ile Gly Cys Gly
1               5                   10                  15

<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Asn Glu Glu Ser Met Tyr Cys Arg Leu Leu Gly Ala Gly Cys Gly
1               5                   10                  15

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Asn Glu Glu Ser Met Tyr Cys Arg Leu Leu Gly Ile Ala Cys Gly
1               5                   10                  15

```
<210> SEQ ID NO 47
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Asn Glu Glu Ser Met Tyr Cys Arg Leu Leu Gly Ile Gly Cys Ala
1               5                   10                  15

<210> SEQ ID NO 48
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Asn Glu Glu Ser Met Phe Cys Arg Leu Leu Gly Ile Gly Cys Gly
1               5                   10                  15

<210> SEQ ID NO 49
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Asn Glu Glu His Met Tyr Cys Arg Leu Leu Gly Ile Gly Cys Gly
1               5                   10                  15

<210> SEQ ID NO 50
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Glu Ser Met Tyr Cys Ala Leu Leu Gly Ile Gly Cys Gly
1               5                   10

<210> SEQ ID NO 51
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Glu Ser Met Tyr Cys Lys Leu Leu Gly Ile Gly Cys Gly
1               5                   10

<210> SEQ ID NO 52
<211> LENGTH: 13
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: L-Ornithine

<400> SEQUENCE: 52

Glu Ser Met Tyr Cys Xaa Leu Leu Gly Ile Gly Cys Gly
1               5                   10

<210> SEQ ID NO 53
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: L-citrulline

<400> SEQUENCE: 53

Glu Ser Met Tyr Cys Xaa Leu Leu Gly Ile Gly Cys Gly
1               5                   10

<210> SEQ ID NO 54
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 8xHis tag"

<400> SEQUENCE: 54

His His His His His His His His
1               5

<210> SEQ ID NO 55
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 55

His His His His His His
1               5

<210> SEQ ID NO 56
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ser Gly Ser Asp Ile Ala Ser Leu Pro Thr Pro Tyr Phe Leu Ser Ile
1               5                   10                  15
```

```
<210> SEQ ID NO 57
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Gly Thr Met Phe Pro Tyr Phe Leu Glu Val Gly
1               5                   10

<210> SEQ ID NO 58
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ser Gly Cys Phe Asp Tyr Pro Cys Phe Leu Thr Ile Asp Ile
1               5                   10

<210> SEQ ID NO 59
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ser Gly Asn Ile Pro Phe Phe Tyr Gly Asp Arg Phe Leu Asp
1               5                   10

<210> SEQ ID NO 60
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ser Gly Gly Leu Gly Phe Pro Tyr Phe Ile His Val Gly Ala
1               5                   10

<210> SEQ ID NO 61
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ser Gly Pro Tyr Phe Val Glu Phe Leu Ser Ala Val Val Val Arg Ser
1               5                   10                  15

Gly

<210> SEQ ID NO 62
```

```
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ser Gly Tyr Pro Tyr Phe Pro Ile Ile Asn Ser Glu Asn Ile Ser Ser
1               5                   10                  15

Ile Asp

<210> SEQ ID NO 63
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ser Gly Thr Met Phe Pro Tyr Phe Leu Glu Val
1               5                   10

<210> SEQ ID NO 64
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ser Gly Gly Leu Pro Ser Gly Cys Leu Asp Tyr Pro Cys Phe Val Pro
1               5                   10                  15

Ile Ser

<210> SEQ ID NO 65
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ser Gly Tyr Phe Leu Cys Leu Phe Glu Asp Val Trp Val Ser Cys Gly
1               5                   10                  15

Leu Leu

<210> SEQ ID NO 66
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Ser Gly Tyr Phe Leu Cys Ala Phe Ala His Gly Trp Ala Leu Cys Asn
1               5                   10                  15
```

Ala Asp

<210> SEQ ID NO 67
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

```
Ser Gly Val His Tyr Phe Leu Cys Ile Val Glu Ser Cys Ser Val Tyr
1               5                   10                  15

Pro Ala
```

<210> SEQ ID NO 68
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

```
Ser Gly Val Phe Phe Met Ala Cys Asp Tyr Val Asn Cys Thr Asp Phe
1               5                   10                  15

Ser Val
```

<210> SEQ ID NO 69
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

```
Asn Met Glu Ser Val His Cys Arg Leu Leu Gly Leu Gly Cys Gly
1               5                   10                  15
```

<210> SEQ ID NO 70
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

```
Asn Glu Glu Ser Ile Tyr Cys Arg Leu Leu Gly Leu Gly Cys Gly
1               5                   10                  15
```

<210> SEQ ID NO 71
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

```
Lys Glu Glu Asn Ile Tyr Cys Arg Leu Leu Ser Leu Gly Cys Ser
```

<210> SEQ ID NO 72
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Asn Glu Glu Ser Ile Tyr Cys Arg Leu Leu Gly Leu Ala Cys Gly
1               5                   10                  15

<210> SEQ ID NO 73
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Lys Glu Asp Ser Met Tyr Cys Arg Leu Leu Gly Leu Gly Cys Gly
1               5                   10                  15

<210> SEQ ID NO 74
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Val Glu Glu Ser Ile Tyr Cys Arg Leu Leu Gly Leu Gly Cys Gly
1               5                   10                  15

<210> SEQ ID NO 75
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ile Glu Glu Ser Ile Tyr Cys Arg Leu Leu Gly Phe Gly Cys Gly
1               5                   10                  15

<210> SEQ ID NO 76
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Asn Gly Asp Asn Met Tyr Cys Arg Leu Leu Gly Leu Gly Cys Glu
1               5                   10                  15

<210> SEQ ID NO 77

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Asp Val Glu Ser Val Tyr Cys Arg Leu Leu Gly Leu Gly Cys Gly
1               5                  10                  15

<210> SEQ ID NO 78
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Asn Asp Glu Ser Val Tyr Cys Arg Leu Leu Gly Ile Gly Cys Gly
1               5                  10                  15

<210> SEQ ID NO 79
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Thr Glu Glu Ser Leu Tyr Cys Arg Leu Leu Gly Val Gly Cys Gly
1               5                  10                  15

<210> SEQ ID NO 80
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Lys Glu Glu Ser Ile His Cys Arg Leu Leu Gly Leu Gly Cys Gly
1               5                  10                  15

<210> SEQ ID NO 81
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Asn Val Glu His Ile His Cys Arg Leu Leu Gly Leu Gly Cys Gly
1               5                  10                  15

<210> SEQ ID NO 82
<211> LENGTH: 15
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 82

Asn Asp Asp Ser Leu Tyr Cys Arg Leu Leu Gly Leu Gly Cys Gly
1               5                  10                  15

<210> SEQ ID NO 83
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Tyr Glu Glu Ser Ile Tyr Cys Arg Leu Leu Gly Ile Gly Cys Gly
1               5                  10                  15

<210> SEQ ID NO 84
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Thr Asp Glu Ser Ile Tyr Cys Arg Leu Leu Ser Ile Ala Cys Gly
1               5                  10                  15

<210> SEQ ID NO 85
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Lys Glu Glu Ser Ile Tyr Cys Arg Leu Leu Gly His Gly Cys Gly
1               5                  10                  15

<210> SEQ ID NO 86
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Asn Glu Glu Asn Met Tyr Cys Arg Leu Met Gly Ile Gly Cys Gly
1               5                  10                  15

<210> SEQ ID NO 87
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 87

Tyr Glu Glu Ser Ile Tyr Cys Arg Leu Leu Gly Leu Gly Cys Gly
1               5                   10                  15

<210> SEQ ID NO 88
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

His Glu Asp His Leu Tyr Cys Arg Leu Leu Gly Ile Gly Cys Gly
1               5                   10                  15

<210> SEQ ID NO 89
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Lys Glu Glu Ser Leu Tyr Cys Arg Leu Leu Gly Leu Gly Cys Gly
1               5                   10                  15

<210> SEQ ID NO 90
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Thr Glu Glu Ser Ile Tyr Cys Arg Leu Leu Gly Leu Gly Cys Asp
1               5                   10                  15

<210> SEQ ID NO 91
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Ala Glu Glu Ser Ile Tyr Cys Arg Leu Leu Gly Leu Gly Cys Gly
1               5                   10                  15

<210> SEQ ID NO 92
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Asn Glu Val Ser Leu Tyr Cys Arg Leu Leu Asp Leu Gly Cys Gly
1               5                   10                  15
```

```
<210> SEQ ID NO 93
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Asn Pro Glu Asn Asn Tyr Cys Arg Leu Leu Asn Leu Gly Cys Gly
1               5                   10                  15

<210> SEQ ID NO 94
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Asn Asp Glu His Met Tyr Cys Arg Leu Leu Gly Leu Asp Cys Asn
1               5                   10                  15

<210> SEQ ID NO 95
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Asn Asp Glu Asn Met Tyr Cys Arg Leu Leu Gly Leu Gly Cys Ala
1               5                   10                  15

<210> SEQ ID NO 96
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Leu Gly Leu Gly
1
```

US 9,624,269 B2

PEPTIDE INHIBITORS OF BACE1

CROSS REFERENCE TO RELATED APPLICATIONS

This application is a divisional of U.S. Ser. No. 14/351,525, (now U.S. Pat. No. 9,193,766), filed Apr. 11, 2014, which is a national stage application filed under 35 USC §371 of PCT Application No. PCT/US2012/059962, filed Oct. 12, 2012, which claims benefit of priority under 35 USC §119(e) of provisional application No. 61/627,573, filed Oct. 14, 2011, the entire contents of each application are incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 27, 2012, is named GNE0394P.txt and is 52,415 bytes in size.

FIELD OF THE INVENTION

The present invention relates generally to peptides which are BACE1 antagonists that, for example, inhibit or decrease BACE1 activity and to compositions comprising such peptides. Additional embodiments include methods for treating various neurological diseases or disorders, as well as methods of reducing Aβ polypeptides in a patient.

BACKGROUND

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least 15 different types of amyloidosis. The major forms are primary amyloidosis without known antecedent, secondary amyloidosis following some other condition, and hereditary amyloidosis.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis, Creutzfeld Jacob disease, Parkinson's disease, HIV-related dementia, ALS (amyotropic lateral sclerosis), Adult Onset Diabetes, senile cardiac amyloidosis, endocrine tumors, and others, including macular degeneration.

The polypeptide β-amyloid (Aβ) is likely to play a central role in the pathogenesis of Alzheimer's disease (AD). Vassar et al., *J. Neurosci.* 29:12787-12794 (2009). Aβ polypeptide accumulation in the CNS results in synaptic dysfunction, axon degeneration and neuronal death. The brains of AD patients show a characteristic pathology of prominent neuropathologic lesions, such as neurofibrillary tangles (NFTs), and amyloid-rich senile plaques. The major component of amyloid plaques is A. These lesions are associated with massive loss of populations of central nervous system (CNS) neurons and their progression accompanies the clinical dementia associated with AD.

Aβ is the proteolytic product of the precursor protein, beta amyloid precursor protein (β-APP or APP). APP is a type-I trans-membrane protein which is sequentially cleaved by two proteases, a β- and γ-secretase. The β-secretase, known as β-site amyloid precursor protein cleaving enzyme 1 (BACE1), first cleaves APP to expose the N-terminus of Aβ, thereby producing a membrane bound fragment known as C99. Vassar et al., *J. Neurosci.*, 29:12787-12794 (2009) and UniProtKB/Swiss-Prot Entry P56817 (BACE1 HUMAN). The γ-secretase then is able to cleave C99 to produce the mature Aβ polypeptide. Aβ is produced with heterogenous C termini ranging in length from 38 amino acids to 43 amino acids. The 42 amino acid form of Aβ ($A\beta_{42}$) is the fibrillogenic form of Aβ and is over produced in patients with Down's syndrome and has been suggested to play a role in the early pathogenesis of AD. Vassar et al., *J. Neurosci.* 29:12787-12794 (2009). BACE1 has thus become a therapeutic target as its inhibition would presumably inhibit Aβ production.

Indeed, BACE1 knock-out mice ($BACE1^{-/-}$) do not produce cerebral Aβ, confirming that BACE1 is the major, if not only, enzyme responsible for producing Aβ in the brain. Roberds et al., *Human Mol. Genetics* 10:1317-1324 (2001). Moreover, BACE1 knockout mice in AD models do not form amyloid plaques; cognitive defects and cholinergic dysfunction are rescued as well. McConlogue et al., *J. Biol. Chem.* 282: 26326-26334 (2007); Ohno et al., *Neuron* 41: 27-33 (2004); and Laird et al., *J. Neurosci.* 25:11693-11709 (2005). Additionally, BACE1 heterozygous knock-out mice have reduced plaque formation indicating the complete inhibition of BACE1 activity is not necessary for plaque reduction. McConlogue et al., *J. Biol. Chem.* 282: 26326-26334 (2007).

The discovery of BACE-1 (Hussain, I. et al. (1999) *Mol Cell Neurosci* 14: 419-27; Sinha, S. et al. (1999) *Nature* 402: 537-40; Vassar, R. et al. (1999) *Science* 286: 735-41; Yan, R. et al. (1999) *Nature* 402: 533-7; Lin, X. et al. (2000) *Proc Natl Acad Sci USA* 97: 1456-60), along with its structure in complex with a substrate-like peptidomimetic inhibitor OM99-2 (Hong, L. et al. (2000) *Science* 290: 150-3) initiated the recent era of pharmaceutical development, triggering the development of many types of BACE1 inhibitors. The first waves of inhibitors were small molecule peptidomimetics (Luo, X. et al. *Int J Clin Exp Pathol* 3: 618-28), which have yet to show clinical success, due in part to the challenge of penetrating the blood brain barrier (BBB). Subsequently, many fragment-based and non-peptidic approaches have led to compounds more suitable for delivery across the BBB to the central nervous system (CNS) (Silvestri, R. (2009) *Med Res Rev* 29: 295-338; Luo, X. et al. (2010) *Int J Clin Exp Pathol* 3: 618-28). Most recently, the development of antibodies has emerged (Pul, R. et al. (2011) *Expert Opin Biol Ther* 11: 343-57). The first class targets Aβ and clears it from the circulation, acting as a sink to modulate Aβ levels in the CNS. The newest class of antibodies targets BACE1 itself, by binding to an exosite and acts as a noncompetitive inhibitor (Atwal, J. K. et al. (2011) *Sci Transl Med* 3: 84ra43; Zhou, L. et al. (2010) *J. Biol. Chem.* 286: 8677-8687). In mice and cynomolgus monkeys, anti-BACE1 reduces not only peripheral Aβ levels, but surprisingly those in the cerebrospinal fluid (CSF) as well. Further engineering of this antibody to incorporate receptor mediated transcytosis across the BBB via bispecific anti-BACE1 anti-transferrin antibodies has resulted in even more effective pharmacodynamic reduction of Aβ in the CNS (Yu, Y. J. et al. (2011) *Sci Transl Med* 3: 84ra44).

It would be beneficial to have an effective therapeutic inhibitor of BACE1 to reduce Aβ production in patients with neurological diseases and disorders, such as AD. The invention provided herein relates to such inhibitors, including their use in a variety of methods.

All references cited herein, including patent applications and publications, are incorporated by reference in their entirety.

SUMMARY OF THE INVENTION

The invention provides peptide and polypeptide inhibitors of BACE1 and methods of using the same. Specifically, the peptides or polypeptides inhibit or reduce the activity of BACE1.

As described below, naïve peptide libraries displayed on phage particles were used to first select for binders and then screen for inhibitors. This led to the discovery of a potent class of peptide inhibitors that bind at the active site in a noncanonical fashion. These peptides inhibit BACE1 in both enzyme assays as well as in cell-based assays, resulting in the reduction of Aβ peptides. The structure of the peptides alone and in complex with BACE1 show a novel binding mode not previously seen in the active site of proteolytic enzymes.

In an embodiment, the invention provides an isolated polypeptide that binds specifically to BACE1, wherein the polypeptide comprises the amino acid sequence X1-S-X2-Y-C-R-L-X3-X4-X5-X6-C-(X7)$_n$ (SEQ ID NO: 6), wherein X1 is glutamic acid or aspartic acid; wherein X2 is methionine, leucine, isoleucine or valine; wherein X3 is leucine or methionine; wherein X4 is glycine, serine or alanine; wherein X5 is leucine, isoleucine or valine; wherein X6 is glycine or alanine; wherein X7 is glycine, aspartic acid or glutamic acid, and wherein n is 0 or 1.

In various embodiments n is 0 (SEQ ID NO: 7). In other embodiments, n is 1 (SEQ ID NO: 8).

In one embodiment, X3 is leucine (SEQ ID NO: 9). In another embodiment, X4 is glycine (SEQ ID NO: 10). In another embodiment, X5 is isoleucine (SEQ ID NO: 11). In another embodiment, X6 is glycine (SEQ ID NO: 12). In another embodiment, X7 is glycine (SEQ ID NO: 13).

In an embodiment, the invention provides an isolated polypeptide comprising an amino acid sequence selected from the group consisting of KEESIYCRLMGLGCG (SEQ ID NO: 14) (BACE018), NELSPYCRLMGLGCD (SEQ ID NO: 15) (BACE019), NEESMYCRLLGIGCG (SEQ ID NO: 16) (BACE20) and PEESLYCRLLALGCG (SEQ ID NO: 17) (BACE021). In an embodiment, the polypeptide comprises the amino acid sequence of NEESMYCRLLGIGCG (SEQ ID NO: 16). In another embodiment, the polypeptide comprises the amino acid sequence of KEESIYCRLMGLGCG (SEQ ID NO: 14). In another embodiment, the polypeptide comprises the amino acid sequence of NELSPYCRLMGLGCD (SEQ ID NO: 15). In another embodiment, the polypeptide comprises the amino acid sequence of PEESLYCRLLALGCG (SEQ ID NO: 17).

In an embodiment, the invention provides an isolated polypeptide consisting essentially of or consisting of an amino acid sequence selected from the group consisting of KEESIYCRLMGLGCG (SEQ ID NO: 14), NELSPYCRLMGLGCD (SEQ ID NO: 15), NEESMYCRLLGIGCG (SEQ ID NO: 16) and PEESLYCRLLALGCG (SEQ ID NO: 17). In an embodiment, the polypeptide consists essentially of or consists of the amino acid sequence of NEESMYCRLLGIGCG (SEQ ID NO: 16). In another embodiment, the polypeptide consists essentially of or consists of the amino acid sequence of KEESIYCRLMGLGCG (SEQ ID NO: 14). In another embodiment, the polypeptide consists essentially of or consists of the amino acid sequence of NELSPYCRLMGLGCD (SEQ ID NO: 15). In another embodiment, the polypeptide consists essentially of or consists of the amino acid sequence of PEESLYCRLLALGCG (SEQ ID NO: 17).

In an embodiment, the invention provides an isolated polypeptide that binds specifically to BACE1, wherein the polypeptide comprises the amino acid sequence SMYCRLLGIGCG (SEQ ID NO: 18) (BACE31). In an embodiment, the polypeptide comprises the amino acid sequence ESMYCRLLGIGCG (SEQ ID NO: 19) (BACE030). In another embodiment, the polypeptide consists essentially of or consists of the amino acid sequence ESMYCRLLGIGCG (SEQ ID NO: 19).

In an embodiment, the invention provides an isolated polypeptide that binds specifically to BACE1, wherein the polypeptide comprises a sequence having cysteines at positions −1 and −8 relative to the C terminus, an arginine or arginine analogue at position −7 relative to the C-terminus, and a leucine at position −6 relative to the C-terminus.

In an embodiment, the amino acid at position −7 relative to the C-terminus is arginine. In an embodiment, the polypeptide comprises small amino acids at positions 0, −2 and −4 relative to the C-terminus. In a further embodiment, the amino acids at positions 0, −2 and −4 relative to the C-terminus are glycine.

In an embodiment, the polypeptide comprises a hydrophobic residue at position −3 relative to the C-terminus.

In an embodiment, the polypeptide comprises a leucine at position −5 relative to the C-terminus.

In an embodiment, the polypeptide comprises a tyrosine or a phenylalanine at position −9 relative to the C-terminus. In a further embodiment, the amino acid at position −9 relative to the C-terminus is tyrosine.

In an embodiment, the polypeptide comprises a bulky hydrophobic residue at position −10 relative to the C-terminus.

In an embodiment, the polypeptide comprises a serine at position −11 relative to the C-terminus.

In an embodiment, the polypeptide comprises an acidic residue at position −12 relative to the C-terminus. In a further embodiment, the amino acid at position −12 relative to the C-terminus is glutamic acid.

In one embodiment, the amino acids at positions 0, −2 and −4 are small amino acids; wherein the amino acid at position −3 is a hydrophobic residue; wherein the amino acid at position −5 is leucine or methionine; wherein the amino acid at position −7 is arginine; wherein the amino acid at position −9 is tyrosine or phenylalanine; wherein the amino acid at position −10 is a bulky hydrophobic residue; wherein the amino acid at position −11 is serine; and wherein the amino acid at position −12 is an acidic amino acid.

In a further embodiment, the amino acids at positions 0, −2 and −4 are glycines; wherein the amino acid at position −3 is a hydrophobic residue; wherein the amino acid at position −5 is leucine; wherein the amino acid at position −7 is arginine; wherein the amino acid at position −9 is tyrosine; wherein the amino acid at position −10 is a bulky hydrophobic residue; wherein the amino acid at position −11 is serine; and wherein the amino acid at position −12 is glutamic acid.

In various embodiments, the polypeptide comprises a sequence selected from the sequences of BACE binding peptides set forth in Table 2 and FIG. 2.

In an embodiment, the polypeptide directly interacts with at least one specific BACE1 residue. In one embodiment, the arginine at position −7 forms salt bridges with aspartate 32 and aspartate 228 of BACE1. In another embodiment, the tyrosine at position −9 binds to the Y loop of BACE1. In another embodiment, the glutamic acid at position −12 forms a salt bridge with arginine 235 of BACE1.

In an embodiment, the polypeptide binds to the substrate groove of BACE1 on the P side. In a further embodiment, the polypeptide binds to the substrate groove of BACE1 on the P side with peptide bonds tracing in the opposite direction from that of the substrate.

In one embodiment, the invention provides an isolated polypeptide that binds specifically to BACE1 and comprises a C-terminal, N-terminal, or internal amino acid sequence comprising the amino acid sequence of a peptide selected from the amino acid sequences set forth in Table 2 and FIG. 2. In some embodiments, the C terminal amino acid sequence is selected from KEESIYCRLMGLGCG (SEQ ID NO: 14), NELSPYCRLMGLGCD (SEQ ID NO: 15), ESMYCRLLGIGCG (SEQ ID NO: 19) and PEESLYCRLLALGCG (SEQ ID NO: 17).

In one embodiment, the invention provides any one of the above described polypeptides wherein the polypeptide is conjugated or fused to a cytotoxic agent or an amino acid sequence tag that enhances cell entry. In various embodiments, the cytotoxic agent is a chemotherapeutic agent or drug, a growth inhibitory agent, a toxin (e.g., protein toxins, enzymatically active toxins of bacterial, fungal, plant, or animal origin, or fragments thereof), or a radioactive isotope. In an embodiment, the amino acid sequence tag that enhances cell entry is a cell penetrating peptide. In an embodiment, the fusion protein comprises a fusion of the BACE1 binding peptide with an amino acid sequence of a protein that normally undergoes absorptive mediated transcytosis or receptor mediated transcytosis through the blood-brain-barrier.

In an embodiment, the invention provides an amino acid sequence that competes with any one of the above-described polypeptides for binding to BACE1.

In an embodiment, the invention provides any one of the above described polypeptides, wherein the polypeptide inhibits endogenous BACE1 proteolytic activity.

In an embodiment, the invention provides an antibody that specifically binds to a polypeptide of the invention, or a fragment thereof.

In an embodiment, the invention provides a kit comprising a polypeptide of the invention.

In one embodiment, a pharmaceutical formulation is provided which comprises a polypeptide of the invention and a pharmaceutically acceptable carrier.

In additional embodiments an isolated nucleic acid encoding a polypeptide of the invention is provided, as well as a vector that comprises the nucleic acid encoding a polypeptide of the invention. In another aspect, a host cell comprising the nucleic acid encoding a polypeptide of the invention is provided as well as methods for producing a polypeptide of the invention comprising culturing the host cell comprising the nucleic acid encoding a polypeptide of the invention under conditions suitable for production of the polypeptide.

In another embodiment, a method of treating an individual having a neurological disease or disorder comprising administering to the individual an effective amount of a polypeptide of the invention is provided.

In an additional embodiment, a method of reducing amyloid plaques, or inhibiting amyloid plaque formation, in a patient suffering from, or at risk of contracting, a neurological disease or disorder comprising administering to the individual an effective amount of a polypeptide of the invention is provided.

In one embodiment, a method of reducing Aβ protein in a patient comprising administering to the patient an effective amount of a polypeptide of the invention is provided. In one embodiment, the patient is suffering from, or at risk of contracting, a neurological disease or disorder.

In another embodiment, a method of inhibiting axon degeneration in a patient comprising administering to the patient an effective amount of a polypeptide of the invention is provided.

In one embodiment of the methods of the invention, the patient is mammalian. In another aspect, the patient is human. In another embodiment, the neurological disease or disorder is selected from the group consisting of Alzheimer's disease (AD), traumatic brain injury, stroke, glaucoma, dementia, muscular dystrophy (MD), multiple sclerosis (MS), amyotrophic lateral sclerosis (ALS), cystic fibrosis, Angelman's syndrome, Liddle syndrome, Paget's disease, traumatic brain injury, Lewy body disease, postpoliomyelitis syndrome, Shy-Draeger syndrome, olivopontocerebellar atrophy, Parkinson's disease, multiple system atrophy, striatonigral degeneration, supranuclear palsy, bovine spongiform encephalopathy, scrapie, Creutzfeldt-Jakob syndrome, kuru, Gerstmann-Straussler-Scheinker disease, chronic wasting disease, fatal familial insomnia, bulbar palsy, motor neuron disease, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome, dementia (including, but not limited to, Pick's disease, and spinocerebellar ataxia). In one embodiment, the neurological disease or disorder is Alzheimer's disease.

BRIEF DESCRIPTION OF THE FIGURES

The file of this patent contains at least one drawing executed in color. Copies of this patent or patent publication with color drawing(s) will be provided by the Office upon request and payment of the necessary fee.

FIG. 1A depicts a sequence alignment of peptide ligands (SEQ ID NOS 21, 56-61, 21, 62, 56, 63-68 and 22-24, respectively, in order of appearance) for BACE1 derived from plate sorting of phage-displayed linear and cyclic peptide libraries. BMS1, BMS2 and BMS4 are the same as peptide identifiers 1, 2 and 4, respectively as previously described (Kornacker, M. G. et al. (2005) *Biochemistry* 44: 11567-73). FIG. 1B depicts the results of an HTRF enzyme activity assay for BACE010 and BACE011 (identified in the figure as "BACE10" and "BACE11", respectively) as compared to known BACE1 inhibitors OM99-2 (identified as "OM99") and statin.

FIG. 2 shows the sequences of peptide ligands (SEQ ID NOS 26, 14, 69-73, 15, 74-78, 16, 79-86, 17 and 87-95, respectively, in order of appearance) for BACE1 derived from solution sorting of phage-displayed peptide libraries in the presence of BACE010 as competitor. BACE017 is a BACE1 binding peptide ligand obtained from the solution panning of BACE1 against the naïve peptide library in the presence of 100 μM BACE010. BACE018-BACE021 are peptide sequences for BACE1 binding peptides derived from the affinity maturation of BACE017. The phage spot ELISA data is listed to indicate the relative binding affinity for individual clones. The column labeled with ELISA is the phage-binding signal to BACE1, s/n ratio represents the signal/noise ratio, in which "signal" is the data as shown in column "ELISA" and noise is the phage-binding signal to BSA as background nonspecific binding. The sequence alignment was summarized as a logo representation (Crooks et al., *Genome Research*, 14:1188-1190, (2004); Schneider and Stephens R M. 1990. *Nucleic Acids Res.* 18:6097-6100 (1990)). The peptides denoted with pepID were selected for peptide synthesis.

FIG. 6A shows the electron density map contoured of the BACE030 peptide, at 1 G (brown mesh), bound to the active site of BACE. FIG. 6B depicts the crystal structure of free BACE1 (grey), BACE030 (green) bound to BACE1 (blue) and OM99-2 (wheat) bound to BACE1 (pink). The active site aspartic acid residues are shown in sticks and colored red. FIG. 6C depicts the superposition of BACE1 complexes with BACE030 (green) and OM99-2 (magenta). The aspartic acid residues at the catalytic site are shown in red. FIG. 6D depicts binding interactions of BACE030 (green) with residues of BACE1 (orange). Water molecules are shown in red spheres. Hydrogen bonds are indicated as dotted red lines. FIG. 6E depicts the superposition of BACE1 complexes with OM99-2 (magenta) and OM03-4 (cyan) in sticks. The surface of BACE1 where BACE1 mutants no longer bind to BACE020 have a red surface and BACE1 mutants that have no effect on BACE030 binding have a green surface.

FIG. 7C discloses "Leu8 Gly9 Leu10 Gly11" as SEQ ID NO: 96.

DETAILED DESCRIPTION OF EMBODIMENTS OF THE INVENTION

Definitions

Figure 1C:
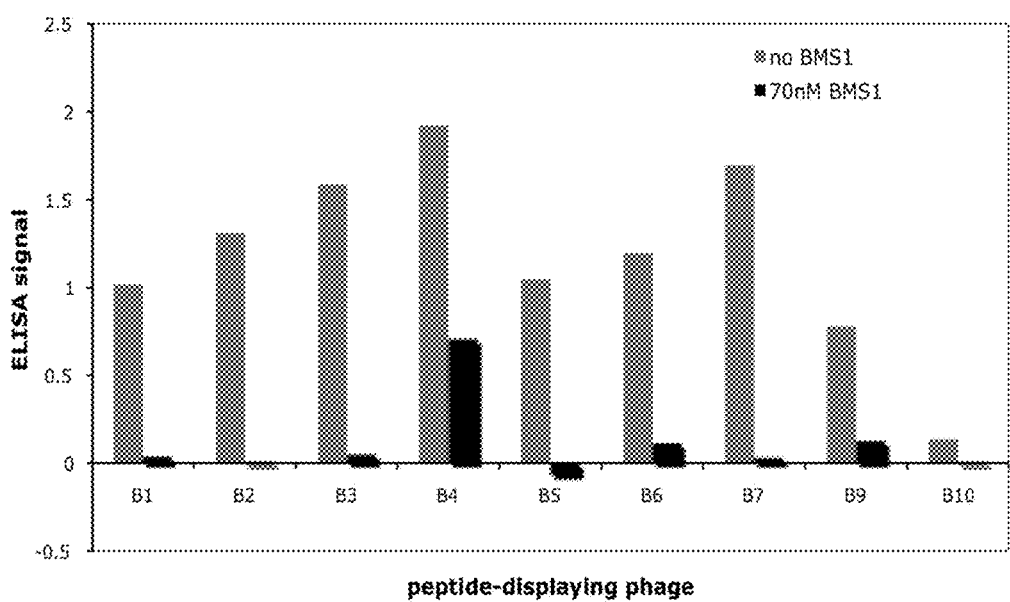
FIG. 1C depicts the competition of peptide-displaying phage bound to BACE1 with synthesized peptide BMS1. The bars represent phage ELISA signal in the absence (gray) or presence (black) of 70 nM BMS1 peptide. The phage peptide ID is as denoted in FIG. 1A.

"Isolated," when referred to a molecule, refers to a molecule that has been identified and separated and/or recovered from a component of its natural environment. Contaminant components of its natural environment are materials that interfere with diagnostic or therapeutic use.

An "active" polypeptide, or fragments thereof, retains a biological activity of the native or naturally-occurring counterpart of the active polypeptide. Biological activity refers to a function mediated by the native or naturally-occurring counterpart of the active polypeptide. For example, binding or protein-protein interaction constitutes a biological activity.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

"Antibody fragments" comprise only a portion of an intact antibody, wherein the portion preferably retains at least one, preferably most or all, of the functions normally associated with that portion when present in an intact antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci.* USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, Ann. Allergy, Asthma & Immunol. 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more complementarity determining regions (CDRs) thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. *Proc Nat. Acad. Sci USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

An "epitope tagged" polypeptide refers to a chimeric polypeptide fused to a "tag polypeptide". Such tags provide epitopes against which antibodies can be made or are available, but do not substantially interfere with polypeptide activity. To reduce anti-tag antibody reactivity with endogenous epitopes, the tag polypeptide is usually unique. Suitable tag polypeptides generally have at least six amino acid residues, usually between about 8 and 50 amino acid residues, preferably between 8 and 20 amino acid residues. Examples of epitope tag sequences include HA from Influenza A virus, GD, and c-myc, poly-His and FLAG.

"Polynucleotide," or "nucleic acid," as used interchangeably herein, refer to polymers of nucleotides of any length, and include, but are not limited to, DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Control sequences", as used herein, are DNA sequences that enable the expression of an operably-linked coding sequence in a particular host organism. Prokaryotic control sequences include promoters, operator sequences, and ribosome binding sites. Eukaryotic control sequences include promoters, polyadenylation signals, and enhancers.

Nucleic acid is "operably-linked" when it is placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous, and, in the case of a secretory leader, contiguous and in reading phase. However, enhancers do not have to be contiguous.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "BACE1," as used herein, refers to any native beta-secretase 1 (also called β-site amyloid precursor protein cleaving enzyme 1, membrane-associated aspartic protease 2, memapsin 2, aspartyl protease 2 or Asp2) from any vertebrate source, including mammals such as primates (e.g. humans) and rodents (e.g., mice and rats), unless otherwise indicated. The term encompasses "full-length," unprocessed BACE1 as well as any form of BACE1 that results from processing in the cell. The term also encompasses naturally occurring variants of BACE1, e.g., splice variants or allelic variants. The amino acid sequence of an exemplary BACE1 polypeptide is shown in SEQ ID NO:1 below, and is the sequence for human BACE1, isoform A as reported in Vassar et al., *Science* 286:735-741 (1999), which is incorporated herein by reference in its entirety.

(SEQ ID NO: 1)
MAQALPWLLLWMGAGVLPAHGTQHGIRLPLRSGLGGAPLGLRLPRETDEE

PEEPGRRGSFVEMVDNLRGKSGQGYYVEMTVGSPPQTLNILVDTGSSNFA

VGAAPHPFLHRYYQRQLSSTYRDLRKGVYVPYTQGKWEGELGTDLVSIPH

GPNVTVRANIAAITESDKFFINGSNWEGILGLAYAEIARPDDSLEPFFDS

LVKQTHVPNLFSLQLCGAGFPLNQSEVLASVGGSMIIGGIDHSLYTGSLW

YTPIRREWYYEVIIVRVEINGQDLKMDCKEYNYDKSIVDSGTTNLRLPKK

VFEAAVKSIKAASSTEKFPDGFWLGEQLVCWQAGTTPWNIFPVISLYLMG

EVTNQSFRITILPQQYLRPVEDVATSQDDCYKFAISQSSTGTVMGAVIME

GFYVVFDRARKRIGFAVSACHVHDEFRTAAVEGPFVTLDMEDCGYNIPQT

DESTLMTIAYVMAAICALFMLPLCLMVCQWCCLRCLRQQHDDFADDISLL

K

Several other isoforms of human BACE1 exist including isoforms B, C and D, shown as SEQ ID NO:2, SEQ ID NO:3 and SEQ ID NO:4, respectively, below. See UniProtKB/Swiss-Prot Entry P56817, which is incorporated herein by reference in its entirety.

(SEQ ID NO: 2)
MAQALPWLLLWMGAGVLPAHGTQHGIRLPLRSGLGGAPLGLRLPRETDEE

PEEPGRRGSFVEMVDNLRGKSGQGYYVEMTVGSPPQTLNILVDTGSSNFA

VGAAPHPFLHRYYQRQLSSTYRDLRKGVYVPYTQGKWEGELGTDLVSIPH

GPNVTVRANIAAITESDKFFINGSNWEGILGLAYAEIARLCGAGFPLNQS

EVLASVGGSMIIGGIDHSLYTGSLWYTPIRREWYYEVIIVRVEINGQDLK

MDCKEYNYDKSIVDSGTTNLRLPKKVFEAAVKSIKAASSTEKFPDGFWLG

EQLVCWQAGTTPWNIFPVISLYLMGEVTNQSFRITILPQQYLRPVEDVAT

SQDDCYKFAISQSSTGTVMGAVIMEGFYVVFDRARKRIGFAVSACHVHDE

FRTAAVEGPFVTLDMEDCGYNIPQTDESTLMTIAYVMAAICALFMLPLCL

MVCQWCCLRCLRQQHDDFADDISLLK (SEQ ID NO: 3)
MAQALPWLLLWMGAGVLPAHGTQHGIRLPLRSGLGGAPLGLRLPRETDEE

PEEPGRRGSFVEMVDNLRGKSGQGYYVEMTVGSPPQTLNILVDTGSSNFA

VGAAPHPFLHRYYQRQLSSTYRDLRKGVYVPYTQGKWEGELGTDLPDDSL

EPFFDSLVKQTHVPNLFSLQLCGAGFPLNQSEVLASVGGSMIIGGIDHSL

YTGSLWYTPIRREWYYEVIIVRVEINGQDLKMDCKEYNYDKSIVDSGTTN

LRLPKKVFEAAVKSIKAASSTEKFPDGFWLGEQLVCWQAGTTPWNIFPVI

SLYLMGEVTNQSFRITILPQQYLRPVEDVATSQDDCYKFAISQSSTGTVM

GAVIMEGFYVVFDRARKRIGFAVSACHVHDEFRTAAVEGPFVTLDMEDCG

YNIPQTDESTLMTIAYVMAAICALFMLPLCLMVCQWCCLRCLRQQHDDFA

DDISLLK (SEQ ID NO: 4)
MAQALPWLLLWMGAGVLPAHGTQHGIRLPLRSGLGGAPLGLRLPRETDEE

PEEPGRRGSFVEMVDNLRGKSGQGYYVEMTVGSPPQTLNILVDTGSSNFA

VGAAPHPFLHRYYQRQLSSTYRDLRKGVYVPYTQGKWEGELGTDLLCGAG

FPLNQSEVLASVGGSMIIGGIDHSLYTGSLWYTPIRREWYYEVIIVRVEI

NGQDLKMDCKEYNYDKSIVDSGTTNLRLPKKVFEAAVKSIKAASSTEKFP

DGFWLGEQLVCWQAGTTPWNIFPVISLYLMGEVTNQSFRITILPQQYLRP

VEDVATSQDDCYKFAISQSSTGTVMGAVIMEGFYVVFDRARKRIGFAVSA

CHVHDEFRTAAVEGPFVTLDMEDCGYNIPQTDESTLMTIAYVMAAICALF

MLPLCLMVCQWCCLRCLRQQHDDFADDISLLK

Isoform B is shown in SEQ ID NO:2 and differs from isoform A (SEQ ID NO:1) in that it is missing amino acids 190-214 (i.e. deletion of amino acids 190-214 of SEQ ID NO:1). Isoform C is shown in SEQ ID NO:3 and differs from isoform A (SEQ ID NO:1) in that it is missing amino acids 146-189 (i.e. deletion of amino acids 146-189 of (SEQ ID NO:1). Isoform D is shown in SEQ ID NO:4 and differs from isoform A (SEQ ID NO:1) in that it is missing amino acids 146-189 and 190-214 (i.e. deletion of amino acids 146-189 and 190-214 of SEQ ID NO:1).

The term "peptide" generally refers to a contiguous and relatively short sequence of amino acids linked by peptidyl bonds. Typically, but not necessarily, a peptide has a length of about 2 to 50 amino acids, 4-40 amino acids or 10-30 amino acids. Although the term "polypeptide" generally refers to longer forms of a peptide, the two terms can be and are used interchangeably in some contexts herein.

The terms "amino acid" and "residue" are used interchangeably herein. A "region" of a polypeptide is a contiguous sequence of 2 or more amino acids. In other embodiments, a region is at least about any of 3, 5, 10, 15 contiguous amino acids.

"C-terminal region", "C-terminal sequence", and variations thereof, as used herein, refer to an amino acid sequence that is located at or in close proximity to the C-terminal end of a polypeptide. Generally, the sequence includes an amino acid that has a free carboxyl group. In one embodiment, a C-terminal region or sequence refers to a region of a polypeptide that includes the about 1-15 residues located closest to the C terminus of the polypeptide.

"N-terminal region", "N-terminal sequence", and variations thereof, as used herein, refer to an amino acid sequence that is located at or in close proximity to the N-terminal end of a polypeptide. Generally, the sequence includes an amino acid that has a free amino group. In one embodiment, a N-terminal region or sequence refers to a region of a polypeptide that includes the about 1-15 residues located closest to the N terminus of the polypeptide.

"Internal region", "internal sequence", and variations thereof, as used herein, refer to an amino acid sequence that is located within a polypeptide and is flanked on both its N- and C-termini by one or more amino acids that are not part of the sequence. Generally, the sequence does not include an amino acid with either a free carboxyl or amino group. In one embodiment, an internal region or sequence refers to a region of a polypeptide that includes the about 1-15 residues located within a polypeptide, wherein the region does not include either the C-terminal or N-terminal amino acid.

"Affinity" refers to the strength of the sum total of noncovalent interactions between a single binding site of a molecule and its binding partner. Unless indicated otherwise, as used herein, "binding affinity" refers to intrinsic binding affinity which reflects a 1:1 interaction between members of a binding pair. The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

A "fusion protein" refers to a polypeptide having two portions covalently linked together, where each of the portions is derived from different proteins. The two portions may be linked directly by a single peptide bond or through a peptide linker containing one or more amino acid residues. Generally, the two portions and the linker will be in reading frame with each other and are produced using recombinant techniques.

A "disorder" or "pathological condition" is any condition that would benefit from treatment with a substance/molecule or method of the invention. This includes chronic and acute disorders or diseases including those pathological conditions which predispose the mammal to the disorder in question. Non-limiting examples of disorders to be treated herein include neurological disorders.

The terms "neurological disorder" or "neurological disease" refer to or describe a disease or disorder of the central and/or peripheral nervous system in mammals. Examples of neurological disorders include, but are not limited to the following list of disease and disorders. Neuropathy disorders are diseases or abnormalities of the nervous system characterized by inappropriate or uncontrolled nerve signaling or lack thereof, and include, but are not limited to, chronic pain (including nociceptive pain (pain caused by an injury to body tissues, including cancer-related pain), neuropathic pain (pain caused by abnormalities in the nerves, spinal cord, or brain), and psychogenic pain (entirely or mostly related to a psychological disorder), headache, migraine, neuropathy, and symptoms and syndromes often accompanying such neuropathy disorders such as vertigo or nausea. Amyloidoses are a group of diseases and disorders associated with extracellular proteinaceous deposits in the CNS, including, but not limited to, secondary amyloidosis, age-related amyloidosis, Alzheimer's Disease (AD), mild cognitive impairment (MCI), Lewy body dementia, Down's syndrome, hereditary cerebral hemorrhage with amyloidosis (Dutch type); the Guam Parkinson-Dementia complex, cerebral amyloid angiopathy, Huntington's disease, progressive supranuclear palsy, multiple sclerosis; Creutzfeld Jacob disease, Parkinson's disease, transmissible spongiform encephalopathy, HIV-related dementia, amyotropic lateral sclerosis (ALS), inclusion-body myositis (IBM), and ocular diseases relating to beta-amyloid deposition (i.e., macular degeneration, drusen-related optic neuropathy, and cataract). Cancers of the CNS are characterized by aberrant proliferation of one or more CNS cell (i.e., a neural cell) and include, but are not limited to, glioma, glioblastoma multiforme, meningioma, astrocytoma, acoustic neuroma, chondroma, oligodendroglioma, medulloblastomas, ganglioglioma, Schwannoma, neurofibroma, neuroblastoma, and extradural, intramedullary or intradural tumors. Ocular diseases or disorders are diseases or disorders of the eye, which for the purposes herein is considered a CNS organ subject to the BBB. Ocular diseases or disorders include, but are not limited to, disorders of sclera, cornea, iris and ciliary body (i.e., scleritis, keratitis, corneal ulcer, corneal abrasion, snow blindness, arc eye, Thygeson's superficial punctate keratopathy, corneal neovascularisation, Fuchs' dystrophy, keratoconus, keratoconjunctivitis sicca, iritis and uveitis), disorders of the lens (i.e., cataract), disorders of choroid and retina (i.e., retinal detachment, retinoschisis, hypertensive retinopathy, diabetic retinopathy, retinopathy, retinopathy of prematurity, age-related macular degeneration, macular degeneration (wet or dry), epiretinal membrane, retinitis pigmentosa and macular edema), glaucoma, floaters, disorders of optic nerve and visual pathways (i.e., Leber's hereditary optic neuropathy and optic disc drusen), disorders of ocular muscles/binocular movement accommodation/refraction (i.e., strabismus, ophthalmoparesis, progressive external opthalmoplegia, esotropia, exotropia, hypermetropia, myopia, astigmatism, anisometropia, presbyopia and ophthalmoplegia), visual disturbances and blindness (i.e., amblyopia, Lever's congenital amaurosis, scotoma, color blindness, achromatopsia, nyctalopia, blindness, river blindness and micro-opthalmia/coloboma), red eye, Argyll Robertson pupil, keratomycosis, xerophthalmia and andaniridia. Viral or microbial infections of the CNS include, but are not limited to, infections by viruses (i.e., influenza, HIV, poliovirus, rubella), bacteria (i.e., *Neisseria* sp., *Streptococcus* sp., *Pseudomonas* sp., *Proteus* sp., *E. coli, S. aureus, Pneumococcus* sp., *Meningococcus* sp., *Haemophilus* sp., and *Mycobacterium tuberculosis*) and other microorganisms such as fungi (i.e., yeast, *Cryptococcus neoformans*), parasites (i.e., *toxoplasma gondii*) or amoebas resulting in CNS pathophysiologies including, but not limited to, meningitis, encephalitis, myelitis, vasculitis and abscess, which can be acute or chronic. Inflammation of the CNS is inflammation that is caused by an injury to the CNS, which can be a physical injury (i.e., due to accident, surgery, brain trauma, spinal cord injury, concussion) or an injury due to or related to one or more other diseases or disorders of the CNS (i.e., abscess, cancer, viral or microbial infection). Ischemia of the CNS, as used herein, refers to a group of disorders relating to aberrant blood flow or vascular behavior in the brain or the causes therefor, and includes, but is not limited to, focal brain ischemia, global brain ischemia, stroke (i.e., subarachnoid hemorrhage and intracerebral hemorrhage), and aneurysm. Neurodegenerative diseases are a group of diseases and disorders associated with neural cell loss of function or death in the CNS, and include, but are not limited to, adrenoleukodystrophy, Alexander's disease, Alper's disease, amyotrophic lateral sclerosis, ataxia telangiectasia, Batten disease, cockayne syndrome, corticobasal degeneration, degeneration caused by or associated with an amyloidosis, Friedreich's ataxia, frontotemporal lobar degeneration, Kennedy's disease, multiple system atrophy, multiple sclerosis, primary lateral sclerosis, progressive supranuclear palsy, spinal muscular atrophy, transverse myelitis, Refsum's disease, and spinocerebellar ataxia. Seizure diseases and disorders of the CNS involve inappropriate and/or abnormal electrical conduction in the CNS, and include, but are not limited to, epilepsy (i.e., absence seizures, atonic seizures, benign Rolandic epilepsy, childhood absence, clonic seizures, complex partial seizures, frontal lobe epilepsy, febrile seizures, infantile spasms, juvenile myoclonic epilepsy, juvenile absence epilepsy, Lennox-Gastaut syndrome, Landau-Kleffner Syndrome, Dravet's syndrome, Otahara syndrome, West syndrome, myoclonic seizures, mitochondrial disorders, progressive myoclonic epilepsies, psychogenic seizures, reflex epilepsy, Rasmussen's Syndrome, simple partial seizures, secondarily generalized seizures, temporal lobe epilepsy, toniclonic seizures, tonic seizures, psychomotor seizures, limbic epilepsy, partial-onset seizures, generalized-onset seizures, status epilepticus, abdominal epilepsy, akinetic seizures, autonomic seizures, massive bilateral myoclonus, catamenial epilepsy, drop seizures, emotional seizures, focal seizures, gelastic seizures, Jacksonian March, Lafora Disease, motor seizures, multifocal seizures, nocturnal seizures, photosensitive seizure, pseudo seizures, sensory seizures, subtle seizures, sylvan seizures, withdrawal seizures, and visual reflex seizures) Behavioral disorders are disorders of the CNS characterized by aberrant behavior on the part of the afflicted subject and include, but are not limited to, sleep disorders (i.e., insomnia, parasomnias, night terrors, circadian rhythm sleep disorders, and narcolepsy), mood disorders (i.e., depression, suicidal depression, anxiety, chronic affective disorders, phobias, panic attacks, obsessive-compulsive disorder, attention deficit hyperactivity disorder (ADHD), attention deficit disorder (ADD), chronic fatigue syndrome, agoraphobia, post-traumatic stress disorder, bipolar disorder), eating disorders (i.e., anorexia or bulimia), psychoses, developmental behavioral disorders (i.e., autism, Rett's syndrome, Aspberger's syndrome), personality disorders and psychotic disorders (i.e., schizophrenia, delusional disorder, and the like). Lysosomal storage disorders are metabolic disorders which are in some cases associated with the CNS or have CNS-specific symptoms; such disorders include, but are not limited to Tay-Sachs disease, Gaucher's disease, Fabry disease, mucopolysaccharidosis (types I, II, III, IV, V, VI and VII), glycogen storage disease, GM1-gangliosidosis, metachromatic leukodystrophy, Farber's disease, Canavan's leukodystrophy, and neuronal ceroid lipofuscinoses types 1 and 2, Niemann-Pick disease, Pompe disease, and Krabbe's disease.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, modulatory compounds of the invention are used to delay development of a disease or disorder.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "effective amount" refers to an amount effective, at dosages and for periods of time necessary, to achieve the desired therapeutic or prophylactic result. A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "package insert" is used to refer to instructions customarily included in commercial packages of therapeutic products, that contain information about the indications, usage, dosage, administration, combination therapy, contraindications and/or warnings concerning the use of such therapeutic products.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

Compositions and Methods of the Invention

A. Peptides and Polypeptides of the Invention

In one aspect, the invention is based, in part, on peptides/polypeptides which bind BACE1 and reduce and/or inhibit BACE1 activity. In certain embodiments, peptides that bind to the active site or an exosite of BACE1 are provided.

BACE1 binder peptides of the invention include those described in Table 2 and in FIG. 2. The invention also provides a mutant or variant peptide any of which residues may be changed from the corresponding residues of these peptides, while still encoding a peptide that maintains inhibitory activity. In one embodiment, a variant of a binder peptide/polypeptide has at least 50%, 60%, 70%, 80%, 90%, 95%, 98%, 99% amino acid sequence identity with the sequence of a reference binder peptide/polypeptide. In general, the variant exhibits substantially the same or greater binding affinity than the reference binder peptide/polypeptide, e.g., at least 0.75×, 0.8×, 0.9×, 1.0×, 1.25× or 1.5× the binding affinity of the reference binder peptide/polypeptide, based on an art-accepted binding assay quantitation unit/metric. In general, variants of the invention include variants in which residues at a particular position in the sequence have been substituted by other amino acids, and further includes the possibility of inserting an additional residue or residues between two residues of the parent peptide/polypeptide as well as the possibility of deleting one or more residues from the parent sequence or adding one or more residues to the parent sequence. Any amino acid substitution, insertion, or deletion is encompassed by the invention. In certain circumstances, the substitution is a conservative substitution as described herein.

"Percent (%) amino acid sequence identity" is defined as the percentage of amino acid residues that are identical with amino acid residues in a reference (parent) polypeptide sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. Those skilled in the art can determine appropriate parameters for measuring alignment, including any algorithms needed to achieve maximal alignment over the full length of the sequences being compared.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=$X/Y$100 where

X is the number of amino acid residues scored as identical matches by the sequence alignment program's or algorithm's alignment of A and B and Y is the total number of amino acid residues in B. If the length of amino acid sequence A is not equal to the length of amino acid sequence B, the % amino acid sequence identity of A to B will not equal the % amino acid sequence identity of B to A.

An "isolated" or "purified" peptide, polypeptide, protein or biologically active fragment is separated and/or recovered from a component of its natural environment. Contaminant components include materials that would typically interfere with diagnostic or therapeutic uses for the polypeptide, and may include enzymes, hormones, and other proteinaceous or non-proteinaceous materials. Preparations having preferably less than 30% by dry weight of non-desired contaminating material (contaminants), preferably less than 20%, 10%, and preferably less than 5% contaminants are considered to be substantially isolated. An isolated, recombinantly-produced peptide/polypeptide or biologically active portion thereof is preferably substantially free of culture medium, i.e., culture medium represents preferably less than 20%, preferably less than about 10%, and preferably less than about 5% of the volume of a peptide/polypeptide preparation. Examples of contaminants include cell debris, culture media, and substances used and produced during in vitro synthesis of the peptide/polypeptide.

Conservative substitutions of peptides/polypeptides are shown in Table A under the heading of "preferred substitutions". If such substitutions result in a change in biological activity, then more substantial changes, denominated "exemplary substitutions" in Table A, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; His | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Amino acids may also be grouped according to common side-chain size, for example, small amino acids (Gly, Ala, Ser, Pro, Thr, Asp, Asn), or bulky hydrophobic amino acids (Met, Ile, Leu).

Substantial modifications in the biological properties of the peptide/polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Non-conservative substitutions will entail exchanging a member of one of these classes for another class.

In further embodiments, peptides or polypeptides of the invention may comprise one or more non-naturally occurring or modified amino acids. A "non-naturally occurring amino acid residue" refers to a residue, other than those naturally occurring amino acid residues listed above, which is able to covalently bind adjacent amino acid residues(s) in a polypeptide chain. Non-natural amino acids include, but are not limited to, homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide and a modified amino acid of alanine. Additional non-natural and modified amino acids, and methods of incorporating them into proteins and peptides, are known in the art (see, e.g., Sandberg et al., (1998) J. Med. Chem. 41: 2481-91; Xie and Schultz (2005) Curr. Opin. Chem. Biol. 9: 548-554; Hodgson and Sanderson (2004) Chem. Soc. Rev. 33: 422-430.

B. Vector Construction

Polynucleotide sequences encoding the peptide and polypeptides described herein can be obtained using standard synthetic and/or recombinant techniques. Desired polynucleotide sequences may be isolated and sequenced from appropriate source cells. Source cells for antibodies would include antibody producing cells such as hybridoma cells. Alternatively, polynucleotides can be synthesized using nucleotide synthesizer or PCR techniques. Once obtained, sequences encoding the peptide or polypeptide are inserted into a recombinant vector capable of replicating and expressing heterologous polynucleotides in a host cell. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication (in particular when the vector is inserted into a prokaryotic cell), a selection marker gene, a promoter, a ribosome binding site (RBS), a signal sequence, the heterologous nucleic acid insert and a transcription termination sequence.

In general, plasmid vectors containing replicon and control sequences which are derived from a species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as Jamda.GEM™-11 may be utilized in making a recombinant vector which can be used to transform susceptible host cells such as E. coli LE392.

Either constitutive or inducible promoters can be used in the present invention, in accordance with the needs of a particular situation, which can be ascertained by one skilled in the art. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the .beta.-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In some embodiments, each cistron within a recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

Prokaryotic host cells suitable for expressing polypeptides include Archaebacteria and Eubacteria, such as Gram-negative or Gram-positive organisms. Examples of useful bacteria include Escherichia (e.g., E. coli), Bacilli (e.g., B. subtilis), Enterobacteria, Pseudomonas species (e.g., P.

*aeruginosa*), *Salmonella typhimurium, Serratia marcescans, Klebsiella, Proteus, Shigella, Rhizobia, Vitreoscilla,* or *Paracoccus*. Preferably, gram-negative cells are used. Preferably the host cell should secrete minimal amounts of proteolytic enzymes, and additional protease inhibitors may desirably be incorporated in the cell culture.

C. Peptide or Polypeptide Production

Host cells are transformed or transfected with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector, protein expression is induced under conditions suitable for the activation of the promoter. For example, if a PhoA promoter is used for controlling transcription, the transformed host cells may be cultured in a phosphate-limiting medium for induction. A variety of other inducers may be used, according to the vector construct employed, as is known in the art.

Polypeptides described herein expressed in a microorganism may be secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therefrom. Cells may be removed from the culture and the culture supernatant being filtered and concentrated for further purification of the proteins produced. The expressed polypeptides can be further isolated and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable antigen immobilized on a matrix and Western blot assay.

Besides prokaryotic host cells, eukaryotic host cell systems are also well established in the art. Suitable hosts include mammalian cell lines such as CHO, and insect cells such as those described below.

D. Polypeptide/Peptide Purification

Polypeptides/peptides that are produced may be purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

E. Identification and Characterization of BACE1 Modulators—General Approach

Candidate BACE1 modulators, e.g. binding peptides, can be identified by any number of methods known in the art. The modulatory characteristics of modulators can be assessed by determining the ability of the modulators to modulate the interaction between BACE1 and its binding partners (such as the substrate APP, or binding polypeptides of the invention). One of the important characteristics is binding affinity. The binding characteristics of candidate modulators (e.g. peptides) of interest can be assessed in any of a number of ways known in the art. The inhibitory characteristics of the modulators can be assessed by determining the ability of the modulators to inhibit a biological activity of BACE1 (e.g, proteolytic activity).

An initial step in the process can include generating one or more candidate peptides comprising sequences of interest, which are then displayed under conditions suitable to determine their BACE1 binding characteristics. For example, candidate peptides can be displayed as carboxyl-terminal (C-terminal) display libraries of peptides on the surface of a phage or phagemid, for example a filamentous phage(mid) using protein fusions with a coat protein such as p3 or p8. C-terminal display is known in the art. See, e.g., Jespers et al., Biotechnology (NY). 13:378-82 and WO 00/06717. These methods may be used to prepare the fusion genes, fusion proteins, vectors, recombinant phage particles, host cells and libraries thereof of the invention. As described herein, in some embodiments, it may be useful to display candidate peptides as amino-terminal (N-terminal) display libraries of peptides on the surface of a phage or phagemid. Methods of N-terminal phage(mid) display include those described herein, and those that are well known in the art, e.g., as described in U.S. Pat. No. 5,750,373 (and references cited therein). Libraries of peptides are well known in the art, and can also be prepared according to art methods. See, e.g., Clark et al., U.S. Pat. No. 6,121,416. Libraries of peptides fused to a heterologous protein component, such as a phage coat protein, are well known in the art, e.g., as described in Clark et al., supra.

Methods of characterizing binder molecules obtained by these methods are also known in the art, including those disclosed in the references cited above (Jespers et al., WO 00/06717 & U.S. Pat. No. 5,750,373) and as described herein. Variants of a first peptide binder can be generated by screening mutants of the peptide to obtain the characteristics of interest (e.g., enhancing target binding affinity, enhanced pharmacokinetics, reduced toxicity, improved therapeutic index, etc.). Mutagenesis techniques are well known in the art. Furthermore, scanning mutagenesis techniques (such as those based on alanine scanning) can be especially helpful to assess structural and/or functional importance of individual amino acid residues within a peptide.

1. Isolation of Binding Phage to BACE1

A phage display library with the displayed candidate BACE1 binding peptides is contacted with BACE1 proteins or fusion proteins in vitro to determine those members of the library that bind to a BACE1 target. Any method known to the skilled artisan may be used to assay for in vitro protein binding. For example, 1, 2, 3 or 4 rounds or more of binding selection may be performed, after which individual phage are isolated and, optionally, analyzed in a phage ELISA. Binding affinities of peptide-displaying phage particles to immobilized BACE1 target proteins may be determined using a phage ELISA (Barrett et al., (1992) Anal Biochem. 204:357-64).

In a situation wherein the candidate is being assessed for the ability to compete with a known BACE1 binder for binding to BACE1, the appropriate binding competition conditions are provided. For example, in one embodiment, screening/selection/biopanning can be performed in the presence of one or more concentrations of the known BACE1 binder. In another embodiment, candidate binders isolated from the library can be subsequently assessed in a competitive ELISA assay in the presence of the known BACE1 binder.

2. Preparation of BACE1

BACE1 may be produced conveniently as a purified protein or protein fragment (e.g, the extracellular domain, residues 22-457, residues 43-453 or residues 57-453 of BACE1) or as a fusion polypeptide using conventional synthetic or recombinant techniques. Fusion polypeptides are useful in phage(mid) display wherein BACE1 is the target for binding, in expression studies, cell-localization, bioassays, ELISAs (including binding competition assays), etc. A BACE1 "chimeric protein" or "fusion protein" comprises BACE1 fused to an unrelated polypeptide. A BACE1 fusion protein may include any portion up to the entire sequence of BACE1, including any number of the biologically active portions. The fusion protein can then be purified according to known methods using affinity chromatography and a capture reagent that binds to the non-BACE1 polypeptide. BACE1 may be fused to an affinity sequence, e.g. the C-terminus of the GST (glutathione S-transferase) sequences. Such fusion proteins facilitate the purification of the recombinant BACE1 using, e.g., glutathione bound to a solid support and/or attachment to solid support (e.g., a matrix for peptide screening/selection/biopanning).

Fusion proteins can be easily created using recombinant methods. A nucleic acid encoding BACE1 (or portion thereof) can be fused in-frame with a non-BACE1 encoding nucleic acid, at the BACE1 N-terminus, C-terminus or internally. Fusion genes may also be synthesized by conventional techniques, including automated DNA synthesizers. PCR amplification using anchor primers that give rise to complementary overhangs between two consecutive gene fragments that can subsequently be annealed and reamplified to generate a chimeric gene sequence (Ausubel et al., Current protocols in molecular biology. John Wiley & Sons, New York 1987) is also useful. Many vectors are commercially available that facilitate sub-cloning BACE1 or a portion thereof in-frame to a fusion protein.

It will be apparent to one of skill in the art that many variations will achieve the goal of isolated BACE1 protein and may be used in this invention. For example, fusions of BACE1 and an epitope tag may be constructed as described above and the tags used to affinity purify BACE1. BACE1 proteins or portions thereof may also be prepared without any fusions; in addition, instead of using the microbial vectors to produce the protein, in vitro chemical synthesis may instead be used. Other cells may be used to produce BACE1 proteins or portions thereof, such as other bacteria, mammalian cells (such as COS), or baculoviral systems. A wide variety of polynucleotide vectors to produce a variety of fusions are also available. The final purification of a BACE1 fusion protein will generally depend on the fusion partner; for example, a poly-histidine tag fusion can be purified on nickel columns.

3. Determining the Sequence of the Displayed Peptide

Phage(mid) that bind to BACE1 with the desired characteristics (and optionally, do not bind to unrelated sequences), can be subjected to sequence analysis. The phage(mid) particles displaying the candidate binding peptides are amplified in host cells, the DNA isolated, and the appropriate portion of the genome (encoding the candidate peptide) sequenced using any appropriate known sequencing technique.

4. Determining Critical Residues in an BACE1 Binding Polypeptide

Alanine Scanning

Alanine scanning of a BACE1 binding peptide sequence can be used to determine the relative contribution of each residue in the peptide to BACE1 binding and/or inhibition. To determine the critical residues in a BACE1 ligand, residues are substituted with a single amino acid, typically an alanine residue, and the effect on BACE1 binding and activity is assessed. See U.S. Pat. No. 5,580,723; U.S. Pat. No. 5,834,250; and the Examples.

Truncations (Deletion Series)

Truncation of a BACE1 binding peptide can elucidate not only binding critical residues, but also determine the minimal length of peptide to achieve binding. In some cases, truncation will reveal a ligand that binds more tightly than the native ligand; such a peptide is useful to modulate BACE1: ligand interactions.

Preferably, a series of BACE1 binding peptide truncations are prepared. One series will truncate the amino terminal amino acids sequentially; in another series, the truncations will begin at the carboxy terminus. As in the case for alanine scanning, the peptides may be synthesized in vitro or prepared by recombinant methods.

Rational Modulator Design

Based on the information obtained from alanine scanning and truncation analysis, the skilled artisan can design and synthesize small molecules, or select small molecule libraries that are enriched in compounds that are likely to modulate binding. For example, based on the information as described in the Examples, a modulator peptide can be designed to include 2 appropriate-spaced cysteine residues and an "arginine finger".

5. Binding Assays

Forming a complex of a BACE1 binding peptide and BACE1 facilitates separation of the complexed from the uncomplexed forms thereof and from impurities. BACE1: binding ligand complexes can be formed in solution or where one of the binding partners is bound to an insoluble support. The complex can be separated from a solution, for example using column chromatography, and can be separated while bound to a solid support by filtration, centrifugation, etc. using well-known techniques. Binding the BACE1 polypeptide or the ligand therefor to a solid support facilitates high throughput assays.

Test compounds can be screened for the ability to modulate (e.g., inhibit) the interaction of a binder polypeptide with BACE1 in the presence and absence of a candidate binding compound, and screening can be accomplished in any suitable vessel, such as microtiter plates, test tubes, and microcentrifuge tubes. Fusion proteins can also be prepared to facilitate testing or separation, where the fusion protein contains an additional domain that allows one or both of the proteins to be bound to a matrix. For example, GST-BACE1-binding peptide fusion proteins or GST-BACE1 proteins can be adsorbed onto glutathione sepharose beads (SIGMA Chemical, St. Louis, Mo.) or glutathione derivatized microtiter plates that are then combined with the test compound, and the mixture is incubated under conditions allowing complex formation (e.g., at physiological conditions of salt and pH). Following incubation, the beads or microtiter plate wells are washed to remove any unbound components, the matrix immobilized in the case of beads, and the complex determined either directly or indirectly. Alternatively, the complexes can be dissociated from the matrix, and the level of binding or activity determined using standard techniques.

Other fusion polypeptide techniques for immobilizing proteins on matrices can also be used in screening assays. Either a BACE1 binding peptide or BACE1 can be immobilized using biotin-avidin or biotin-streptavidin systems. Biotinylation can be accomplished using many reagents, such as biotin-N-hydroxy-succinimide (NHS; PIERCE Chemicals, Rockford, Ill.), and immobilized in wells of streptavidin coated 96 well plates (PIERCE Chemical). Alternatively, antibodies reactive with BACE1 binding peptides or BACE1 but which do not interfere with binding of a binding peptide to its target molecule can be derivatized to the wells of the plate, and unbound BACE1 or binder peptide trapped in the wells by antibody conjugation. Methods for detecting such complexes, in addition to those described for the GST-immobilized complexes, include immunodetection of complexes using antibodies reactive with the binder peptides or BACE1.

Assay for Binding: Competition ELISA

To assess the binding affinities of a peptide, protein or other BACE1 ligand, competition binding assays may be used, where the ability of the ligand to bind BACE1 (and the binding affinity, if desired) is assessed and compared to that of a compound known to bind BACE1, for example, a peptidomimetic inhibitor of BACE1 such as OM99-2, a BACE1 antibody, or a high-affinity binder peptide determined by phage display as described herein.

Many methods are known and can be used to identify the binding affinities of binding molecules (e.g. peptides, proteins, small molecules, etc.); for example, binding affinities can be determined as $IC_{50}$ values using competition ELISAs. The $IC_{50}$ value is defined as the concentration of binder that blocks 50% of BACE1 binding to a ligand. For example, in solid phase assays, assay plates may be prepared by coating microwell plates (preferably treated to efficiently adsorb protein) with neutravidin, avidin or streptavidin. Non-specific binding sites are then blocked through addition of a solution of bovine serum albumin (BSA) or other proteins (for example, nonfat milk) and then washed, preferably with a buffer containing a detergent, such as Tween-20. A biotinylated known BACE1 binder (for example, the phage peptides as fusions with GST or other such molecule to facilitate purification and detection) is prepared and bound to the plate. Serial dilutions of the molecule to be tested with BACE1 are prepared and contacted with the bound binder. The plate coated with the immobilized binder is washed before adding each binding reaction to the wells and briefly incubated. After further washing, the binding reactions are detected, often with an antibody recognizing the non-BACE1 fusion partner and a labeled (such as horseradish peroxidase (HRP), alkaline phosphatase (AP), or a fluorescent tag such as fluorescein) secondary antibody recognizing the primary antibody. The plates are then developed with the appropriate substrate (depending on the label) and the signal quantified, such as using a spectrophotometric plate reader. The absorption signal may be fit to a binding curve using a least squares fit. Thus the ability of the various molecules to inhibit BACE1 from binding a known BACE1 binder can be measured.

Apparent to one of skill are the many variations of the above assay. For example, instead of avidin-biotin based systems, BACE1 binders may be chemically-linked to a substrate, or simply adsorbed.

F. Activity Assays

Determination of the ability of a candidate peptide or polypeptide of the invention (such as a peptide comprising the amino acid sequence of a binder peptide disclosed herein) to modulate BACE1 activity can be performed by testing the modulatory capability of the substance/molecule in in vitro or in vivo assays. Modulatory capability may include, e.g., inhibition or reduction of BACE1 aspartyl protease activity; or inhibition or reduction in APP cleavage by BACE1; or inhibition or reduction in Aβ production.

In certain embodiments, a peptide/polypeptide of the invention, such as a peptide comprising the amino acid sequence of a binder peptide disclosed herein, is tested for such biological activity. For example, BACE1 protease activity can be tested in an homogeneous time-resolved fluorescence HTRF assay or a microfluidic capillary electrophoretic (MCE) assay, as described in detail in Example 1, using synthetic substrate peptides.

Briefly, a homogeneous time-resolved fluorescence (HTRF) assay can be used to measure BACE1 aspartyl protease activity with the use of an amyloid precursor protein BACE1 cleavage site peptide. For example, the Bi27 peptide (Biotin-KTEEISEVNLDAEFRHDSGYEVHHQKL (SEQ ID NO:5), American Peptide Company)), is combined with BACE1 pre-incubated with an anti-BACE antibody in BACE reaction buffer (50 mM sodium acetate pH 4.4 and 0.1% CHAPS) in a 384-well plate (Proxiplate™, Perkin-Elmer). The proteolytic reaction mixture is incubated at ambient temperature for 75 minutes and is quenched by the addition of 5 μL HTRF detection mixture containing 2 nM Streptavidin-D2 and 150 nM of an anti-amyloid beta antibody labeled with Europium cryptate in detection buffer (200 mM Tris pH 8.0, 20 mM EDTA, 0.1% BSA, and 0.8M KF). The final reaction mixture is incubated at ambient temperature for 60 minutes and the TR-FRET signal is measured using an EnVision Multilabel Plate Reader™

(Perkin-Elmer) at an excitation wavelength of 320 nm and emission wavelengths of 615 and 665 nm.

An MCE assay reactions can be carried out in a standard enzymatic reaction, initiated by the addition of substrate to enzyme and 4× compound, containing human BACE1 (extracellular domain), amyloid precursor protein beta secretase active site peptide (FAM-KTEEISEVNLDAEFRWKK-CONH$_2$ (SEQ ID NO: 20)), 50 mM NaOAc pH 4.4 and 0.1% CHAPS. After incubation for 60 minutes at ambient temperature, the product and substrate in each reaction is separated using a 12-sipper microfluidic chip analyzed on an LC3000® (both, Caliper Life Sciences). The separation of product and substrate is optimized by choosing voltages and pressure using the manufacturer's optimization software. Substrate conversion is calculated from the electrophoregram using HTS Well Analyzer software (Caliper Life Sciences).

In addition, BACE1 protease activity can be tested in vivo in cell lines which express BACE1 substrates such as APP, or in transgenic mice which express BACE1 substrates, such as human APP.

Additionally, BACE1 protease activity can be tested in animal models. For example, animal models of various neurological diseases and disorders, and associated techniques for examining the pathological processes associated with these models, are readily available in the art. Animal models of various neurological disorders include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, and implantation under the renal capsule. In vivo models include models of stroke/cerebral ischemia, in vivo models of neurodegenerative diseases, such as mouse models of Parkinson's disease; mouse models of Alzheimer's disease; mouse models of amyotrophic lateral sclerosis; mouse models of spinal muscular atrophy; mouse/rat models of focal and global cerebral ischemia, for instance, common carotid artery occlusion or middle cerebral artery occlusion models; or in ex vivo whole embryo cultures. As one nonlimiting example, there are a number of art-known mouse models for Alzheimer's disease ((see, e.g. Rakover et al., *Neurodegener. Dis.* (2007); 4(5): 392-402; Mouri et al., *FASEB J.* (2007) July; 21 (9): 2135-48; Minkeviciene et al., *J. Pharmacol. Exp. Ther.* (2004) November; 311 (2):677-82 and Yuede et al., *Behav Pharmacol.* (2007) September; 18 (5-6): 347-63). The various assays may be conducted in known in vitro or in vivo assay formats, as known in the art and described in the literature. Various such animal models are also available from commercial vendors such as the Jackson Laboratory.

G. Examples of Uses for BACE1 Binders

The identification and characterization of the BACE1 peptide binders as described herein provides compositions and methods for modulating the in vivo interactions between BACE1 and its substrates, e.g., APP. The BACE1 peptide binders as described herein may be used in the treatment of diseases and disorders such as neurological disorders, as discussed below.

Well-characterized moderate to high affinity peptide binders of BACE1 as described herein can be further used to elucidate important structural characteristics of BACE1 itself. Knowledge of such provides for development of modulatory agents based on modification of the BACE1 sequence itself.

Other uses of modulators of BACE1 include diagnostic assays for diseases related to BACE1 and its associating partners, and the use of BACE1 and ligands in fusion proteins as purification handles and anchors to substrates.

The BACE1 binding peptides as described herein may also be used for screening additional compounds to identify those that modulate BACE1-ligand interaction. Screening assays are designed to identify compounds that bind or complex with BACE1, or otherwise interfere with the interaction of BACE1 and cellular factors. One approach to determining the ability of a candidate compound to be a modulator is to assess the activity of the candidate compound in a competitive inhibition assay in the presence of a known BACE1 binder, such as any of the binder peptides (e.g., the high affinity binders described in the Examples) disclosed herein. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for modulators are common in that they call for contacting the candidate modulator with BACE1 (or equivalent thereof) and/or binding ligand that is involved in the binding interaction of BACE1 and the binding ligand, under conditions and for a time sufficient to allow these two components to interact.

In binding assays, the interaction is binding and the complex formed can be isolated or detected in the reaction mixture. In a particular embodiment, a candidate substance or molecule is immobilized on a solid phase, e.g., on a microtiter plate, by covalent or non-covalent attachments. Non-covalent attachment generally is accomplished by coating the solid surface with a solution of the substance/molecule and drying. Alternatively, an immobilized affinity molecule, such as an antibody, e.g., a monoclonal antibody, specific for the substance/molecule to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

Candidate compounds can be generated by combinatorial libraries and/or mutations of known binders based on information described herein, in particular information relating to contributions and importance to BACE1-ligand binding interactions of individual residues and moieties within a ligand or BACE1 sequence itself.

Compounds that interfere with the interaction of BACE1 and binding ligand can be tested as follows: usually a reaction mixture is prepared containing BACE1 and a ligand under conditions and for a time allowing for the interaction and binding of the two molecules. To test the ability of a candidate compound to inhibit the binding interaction, the reaction is run in the absence and in the presence of the test compound. In addition, a control compound may be added to a third reaction mixture, to serve as positive control. The binding (complex formation) between the test compound and BACE1 and/or binding ligand present in the mixture is monitored, as described hereinabove. The formation of a complex in the control reaction(s) but not in the reaction mixture containing the test compound indicates that the test compound interferes with the interaction of BACE1 and binding ligand.

H. Peptide Conjugates

The invention also provides peptide conjugates comprising a BACE1 binding peptide as disclosed herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, a peptide conjugate comprises a BACE1 binding peptide as described herein conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, a peptide conjugate comprises a BACE1 binding peptide as described herein conjugated to an enzymatically active toxin or fragment thereof, including but not limited to diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

In another embodiment, a peptide conjugate comprises a BACE1 binding peptide as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of a peptide and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The peptide conjugates herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

In further embodiments, peptide conjugates include fusion proteins comprising a BACE1 binding peptide as disclosed herein fused to another, heterologous polypeptide or amino acid sequence. In one embodiment, such a fusion protein comprises a fusion of the BACE1 binding peptide with an enzymatically active toxin, such as any of those disclosed above.

In an alternative embodiment, the fusion protein comprises a fusion of the BACE1 binding peptide with an amino acid sequence that enhances polypeptide cell entry. In one embodiment, the amino acid sequence is a cell penetrating peptide (CCP), e.g., tat peptide, penetratin, herpesvirus tegument protein VP22, transportan, model amphipathic peptide (MAP), an arginine oligomer, or other CCP known in the art. See, e.g., Sebbage, (2009) Bioscience Horizons 2: 64-72; and Delcroix and Riley, (2010) Pharmaceuticals 3: 448-470.

In an embodiment, the fusion protein comprises a fusion of the BACE1 binding peptide with an amino acid sequence of a protein that normally undergoes absorptive mediated transcytosis or receptor mediated transcytosis through the blood-brain-barrier. These proteins include but are not limited to ligands for brain capillary endothelial receptors such as a monoclonal antibody to the transferrin receptor or to the insulin receptor, histones, biotin, folate, niacin, panthothenic acid, or glycopeptides. In another embodiment, the BACE1 binding peptide is linked to a highly positively charged compound such as lysine, polylysine, arginine, polyarginine, lysine-arginine peptide, putrescine, spermidine, spermine, etc, all of which are known to facilitate crossing through the blood-brain-barrier, presumably by binding to a receptor.

In an alternative embodiment, the fusion protein can comprise a fusion of a BACE1 binding peptide with an immunoglobulin or a particular region of an immunoglobulin, for example, the Fc region of an IgG molecule. For the production of immunoglobulin fusions see, e.g., U.S. Pat. No. 5,428,130 issued Jun. 27, 1995. In alternative embodiments, the BACE1 binding peptide is fused to an agent that results in improved PK and/or pharmacodynamics of the peptide. In some embodiments, the peptide is an albumin fusion protein. In some embodiments, the fusion protein is a pegylated fusion protein.

I. Pharmaceutical Compositions

A BACE1 binding peptide or polypeptide of the invention can be incorporated into compositions, which in some embodiments are suitable for pharmaceutical use. Such compositions typically comprise the peptide or polypeptide, and an acceptable carrier, for example one that is pharmaceutically acceptable. A "pharmaceutically acceptable carrier" includes any and all solvents, dispersion media, coatings, antibacterial and antifungal agents, isotonic and absorption delaying agents, and the like, compatible with pharmaceutical administration (Gennaro, Remington: The science and practice of pharmacy. Lippincott, Williams & Wilkins, Philadelphia, Pa. (2000)). Examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

1. General Considerations

A pharmaceutical composition is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

2. Injectable Formulations

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents; for example, parabens, chlorobutanol, phenol, ascorbic acid, and thimerosal, can contain microorganism contamination. Isotonic agents; for example, sugars, polyalcohols such as manitol, sorbitol, and sodium chloride can be included in the composition. Compositions that can delay absorption include agents such as aluminum monostearate and gelatin.

Sterile injectable solutions can be prepared by incorporating the active compound (e.g., any modulator substance/molecule of the invention) in the required amount in an appropriate solvent with one or a combination of ingredients as required, followed by sterilization. Generally, dispersions are prepared by incorporating the active compound into a sterile vehicle that contains a basic dispersion medium, and the other required ingredients. Sterile powders for the preparation of sterile injectable solutions, methods of preparation include vacuum drying and freeze-drying that yield a powder containing the active ingredient and any desired ingredient from a sterile solutions.

3. Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

4. Compositions for Inhalation

For administration by inhalation, the compounds are delivered as an aerosol spray from a nebulizer or a pressurized container that contains a suitable propellant, e.g., a gas such as carbon dioxide.

5. Systemic Administration

Systemic administration can also be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

6. Carriers

In one embodiment, the active compounds are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art. Liposomal suspensions can also be used as pharmaceutically acceptable carriers. These can be prepared according to methods known to those skilled in the art, such as in (Eppstein et al., U.S. Pat. No. 4,522,811, 1985).

7. Unit Dosage

Oral formulations or parenteral compositions in unit dosage form can be created to facilitate administration and dosage uniformity. Unit dosage form refers to physically discrete units suited as single dosages for the subject to be treated, containing a therapeutically effective quantity of active compound in association with the required pharmaceutical carrier. The specification for the unit dosage forms are dictated by, and directly dependent on, the unique characteristics of the active compound and the particular desired therapeutic effect, and the inherent limitations of compounding the active compound.

8. Gene Therapy Compositions

Nucleic acid molecules encoding peptides or polypeptides of the invention can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al., *Proc Natl Acad Sci USA.* 91; 3054-7 (1994)). The pharmaceutical preparation of a gene therapy vector can include an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

J. Therapeutic Methods

Any of the BACE1 binding peptides or polypeptides provided herein may be used in therapeutic methods.

In one aspect, a BACE1 binding peptide or polypeptide for use as a medicament is provided. In further aspects, an anti-BACE1 antibody for use in treating a neurological disease or disorder is provided (e.g., AD). In certain embodiments, a BACE1 binding peptide or polypeptide for use in a method of treatment is provided. In certain embodiments, the invention provides a BACE1 binding peptide or polypeptide for use in a method of treating an individual having a neurological disease or disorder comprising administering to the individual an effective amount of the BACE1 binding peptide or polypeptide. In one such embodiment, the method further comprises administering to the individual an effective amount of at least one additional therapeutic agent. In further embodiments, the invention provides a BACE1 binding peptide or polypeptide for use in reducing or inhibiting amlyoid plaque formation in a patient at risk or suffering from a neurological disease or disorder (e.g., AD). In certain embodiments, the invention provides a BACE1 binding peptide or polypeptide for use in a method of reducing or inhibiting Aβ production in an individual comprising administering to the individual an effective amount of the BACE1 binding peptide or polypeptide. An "individual" according to any of the above embodiments is preferably a human. In certain aspects, the BACE1 binding peptide or polypeptide for use in the methods of the invention reduces or inhibits BACE1 activity. For example, the BACE1 binding peptide or polypeptide reduces or inhibits the ability of BACE1 to cleave APP.

In a further aspect, the invention provides for the use of a BACE1 binding peptide or polypeptide in the manufacture or preparation of a medicament. In one embodiment, the medicament is for treatment of neurological disease or disorder. In a further embodiment, the medicament is for use in a method of treating neurological disease or disorder comprising administering to an individual having neurological disease or disorder an effective amount of the medicament. In one such embodiment, the method further comprises administering to the individual an effective amount of at least one additional therapeutic agent, e.g., as described below. In a further embodiment, the medicament is for inhibiting BACE1 activity. In a further embodiment, the medicament is for use in a method of inhibiting Aβ production or plaque formation in an individual comprising administering to the individual an amount effective of the medicament to inhibit Aβ production or plaque formation. An "individual" according to any of the above embodiments may be a human.

In a further aspect, the invention provides a method for treating Alzheimer's disease. In one embodiment, the method comprises administering to an individual having AD an effective amount of a BACE1 binding peptide or polypeptide. In one such embodiment, the method further comprises administering to the individual an effective amount of at least one additional therapeutic agent. An "individual" according to any of the above embodiments may be a human.

In a further aspect, the invention provides pharmaceutical formulations comprising any of the BACE1 binding peptides or polypeptides provided herein, e.g., for use in any of the above therapeutic methods. In one embodiment, a pharmaceutical formulation comprises any of the BACE1 binding peptides or polypeptides provided herein and a pharmaceutically acceptable carrier. In another embodiment, a pharmaceutical formulation comprises any of the BACE1 binding peptides or polypeptides provided herein and at least one additional therapeutic agent, e.g., as described below.

Peptides or polypeptides of the invention can be used either alone or in combination with other agents in a therapy. For instance, a peptide or polypeptide of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Peptides or polypeptides of the invention can also be used in combination with radiation therapy.

A peptide or polypeptide of the invention (and any additional therapeutic agent) can be administered by any suitable means, including parenteral, intrapulmonary, intrathecal and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Certain embodiments of the invention provide for the peptide or polypeptide to traverse the blood-brain barrier. Certain neurodegenerative diseases are associated with an increase in permeability of the blood-brain barrier, such that the peptide or polypeptide can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the peptide or polypeptide across the blood-brain barrier include, but are not limited to, circumventing the blood-brain barrier entirely, or by creating openings in the blood-brain barrier. Circumvention methods include, but are not limited to, direct injection into the brain (see e.g., Papanastassiou et al., *Gene Therapy* 9: 398-406 (2002)) and implanting a delivery device in the brain (see e.g., Gill et al., *Nature Med*. 9: 589-595 (2003); and Gliadel Wafers™, Guildford Pharmaceutical). Methods of creating openings in the barrier include, but are not limited to, ultrasound (see e.g., U.S. Patent Publication No. 2002/0038086), osmotic pressure (e.g., by administration of hypertonic mannitol (Neuwelt, E. A., *Implication of the Blood-Brain Barrier and its Manipulation*, Vols 1 & 2, Plenum Press, N.Y. (1989))), permeabilization by, e.g., bradykinin or permeabilizer A-7 (see e.g., U.S. Pat. Nos. 5,112,596, 5,268,164, 5,506,206, and 5,686,416), and transfection of neurons that straddle the blood-brain barrier with vectors containing genes encoding the antibody or fragment thereof (see e.g., U.S. Patent Publication No. 2003/0083299).

Lipid-based methods of transporting the peptide or polypeptide across the blood-brain barrier include, but are not limited to, encapsulating the peptide or polypeptide in liposomes that are coupled to antibody binding fragments that bind to receptors on the vascular endothelium of the blood-brain barrier (see e.g., U.S. Patent Application Publication No. 20020025313), and coating the peptide or polypeptide in low-density lipoprotein particles (see e.g., U.S. Patent Application Publication No. 20040204354) or apolipoprotein E (see e.g., U.S. Patent Application Publication No. 20040131692).

Receptor-based methods of transporting the peptide or polypeptide across the blood-brain barrier include, but are not limited to, conjugation of the peptide or polypeptide to ligands that recognize receptors expressed at the blood-brain barrier, resulting in their being carried across the blood-brain barrier after receptor-mediated transcytosis (Gabathuler (2010) Neurobiology of Disease 37; 48-57). These ligands include but are not limited to ligands for brain capillary endothelial receptors such as a monoclonal antibody to the transferrin receptor or to the insulin receptor, histones, biotin, folate, niacin, panthothenic acid, or glycopeptides.

Peptides or polypeptides of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The peptide or polypeptide need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a peptide or polypeptide of the invention (when used alone or in combination with one or more other additional therapeutic agents) will depend on the type of disease to be treated, the severity and course of the disease, whether the peptide or polypeptide is administered for preventive or therapeutic purposes, previous therapy, the patient's clinical history and response to the peptide or polypeptide, and the discretion of the attending physician. The peptide or polypeptide is suitably administered to the patient at one time or over a series of treatments. Depending on the type and severity of the disease, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

However, the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. The progress of this therapy is easily monitored by conventional techniques and assays.

K. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a peptide or polypeptide of the invention. The label or package insert indicates that the composition is used for treating the condition of choice. Moreover, the article of manufacture may comprise (a) a first container with a composition contained therein, wherein the composition comprises a peptide or polypeptide of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples are included to demonstrate preferred embodiments of the present invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing form the spirit and scope of the invention.

EXAMPLES

Example 1

Selection and Characterization of Peptide Inhibitors of BACE1

Materials and Methods

Materials.

Enzymes and M13-KO7 helper phage were obtained from New England Biolabs. Maxisorp immunoplates plates were obtained from Nalgene NUNC International (Naperville, Ill.). Dynabeads® MyOne Streptavidin was obtained from Invitrogen (Carlsbad, Calif.). 3,3',5,5'-Tetramethyl-benzidine/$H_2O_2$ (TMB) peroxidase substrate was obtained from Kirkegaard and Perry Laboratories, Inc (Gaithersburg, Md.). NeutrAvidin and Streptavidin were obtained from Thermo Scientific (Rockford, Ill.). OM99-2 (Cat. No. 496000) was obtained from EMD Biosciences (San Diego, Calif.).

Library Construction.

The phage displayed peptide library was constructed using standard Kunkel mutagenesis (Kunkel, T. A. et al. (1987) *Methods Enzymol* 154: 367-82). Two groups of phage-displayed peptide libraries, Linear-lib and Cyclic-lib (cysteine disulfide-containing), were constructed by fusing randomized peptides to the N-terminus of M13 major coat protein following the standard protocol for making phage displayed libraries (Sidhu, S. S. et al. (2000) *Methods Enzymol* 328: 333-63). The Linear-lib consisted of random peptides with 8, 10, 12, 14, 16 amino acids in length encoded by consecutive degenerate codons (NNK, where N=A/C/G/T and K=G/T). Libraries with different lengths were constructed individually and pooled together, each having the same concentration. The Cyclic-lib consisted of 14-mer random peptides with varied lengths between two fixed cysteines. They are designated as $X_6CX_3CX_5$, $X_5CX_4CX_5$, $X_5CX_5CX_4$, $X_4CX_6CX_4$, $X_4CX_7CX_3$, $X_3CX_8CX_3$, $X_3CX_9CX_2$, $X_2CX_{10}CX_2$, where X represents a residue encoded by the NNK codon, the number represents the number of residues and C represents a fixed cysteine. These libraries were constructed individually and pooled together with the same concentration for each. Final diversities for the Linear-lib and Cyclic-Lib were $1.8 \times 10^{11}$ and $7.8 \times 10^{11}$, respectively.

A soft randomized library was constructed using degenerate oligonucleotides synthesized with 70-10-10-10 mixtures of nucleotide bases, in which the wild type base is in excess. This results in wild type amino acids occurring at approximately 50% in frequency at the targeted position.

Selection of Peptide Ligands for Human BACE1 (BACE1).

Phage pools of the Linear-lib and the Cyclic-lib were cycled through rounds of binding selections either with plate-coated BACE1 using a standard phage panning protocol (Sidhu, S. S. et al. (2000) *Methods Enzymol* 328: 333-63) or with biotinylated BACE1 in solution. BACE1 was biotinylated in vitro with the EZ-Link Sulfo-NHS-LC-Biotinylation Kit (Cat. No. 21435) from Thermo Scientific (Rockford, Ill.) following the manufacturer's instructions. For round 1, 20 µg of biotinylated BACE1 was incubated with 1 ml of phage library (~$1 \times 10^{13}$ pfu/ml) at 4° C. for 2 h, captured for 15 min at room temperature by 200 µl of DYNABEADS® MyOne Streptavidin that was previously blocked with Block buffer (PBS, 1% BSA and 0.1% Tween20). The supernatant was discarded and the bead was washed for three times with Wash buffer (PBS with 0.1% Tween20). The bound phage was eluted with 400 µl 0.1 M HCl for 7 minutes and immediately neutralized with 60 µl 1 M Tris, pH 13. The eluted phage was amplified as previously described (Sidhu, S. S. et al. (2000) *Methods Enzymol* 328: 333-63). For round 2, the protocol was the same as round one except using 10 µg biotinylated BACE1 and 100 µl of DYNABEADS®. For round 3, 2 µg biotinylated BACE1 was incubated with the amplified phage from the previous round and the phage-BACE1 complex was captured by NeutrAvidin-coated plates previously coated with Block buffer. Round 4 was the same as round 3 except using Streptavidin-coated plates to capture the biotin-BACE1-phage complex.

After 4 rounds of binding selection, individual phage clones were analyzed in a high-throughput spot phage ELISA (Sidhu, S. S. et al. (2000) *Methods Enzymol* 328: 333-63) using plate-immobilized BACE1 as the target. The binding signal of the same phage particle to BSA was detected as non-specific binding noise. Clones with phage binding signal to target over 0.5 and signal/noise ratio>3 were considered to be positive clones and were subjected to DNA sequence analysis.

Peptides were synthesized by either manual or automated (Protein Technologies, Inc. Symphony Peptide synthesizer) Fmoc-based solid phase synthesis on a 0.25 mmol scale using a polystyrene resin (see Bodanszky, M., and Bodanszky, A. (1984) in *The Practice of Peptide Synthesis*, Springer-Verlag, New York). Upon completion of synthesis, side chain protection groups were removed and the peptide was cleaved from the resin with 95% trifluoroacetic acid (TFA), 2.5% triisopropylsilane, and 2.5% water. Oxidation of the cysteines to disulfide bonds was carried out by adding a saturated iodine solution in acetic acid. Purification of peptides was performed by reversed phase HPLC with a water/acetonitrile gradient containing 0.1% TFA. The purity of each peptide was determined by analytical HPLC to be greater than 95% homogeneous, and its identity was verified by mass spectrometry. Peptides BMS1, BMS2 and BMS4 are the same as Peptide 1, Peptide 2 and Peptide 4, respectively, described in Kornacker et al. *Biochemistry* 44:11567-11573 (2005).

BACE1 HTRF Activity Assay.

The BACE1 HTRF reaction was initiated by the addition of 2 µl of 600 nM Bi27 (Biotin-KTEEISEVNLDAEFRH-DSGYEVHHQKL (SEQ ID NO: 5), American Peptide Company) to 6 µl of 2.7 nM rhBACE1 pre-incubated with peptides or small molecule inhibitors in BACE1 reaction buffer (50 mM NaOAc pH 4.4 and 0.1% CHAPS) in a 384-well Proxiplate (Perkin Elmer). The 8 µl proteolytic reaction mixture was incubated at ambient temperature for 24 h and was quenched by the addition of 8 µl HTRF detection mixture containing 150 nM Streptavidin-D2 and 5 nM 6E10 labeled with Europium cryptate in detection buffer (200 mM Tris pH 8.0, 20 mM EDTA, 0.1% BSA, and 0.8 M KF). The final reaction mixture was incubated at room temperature for 60 min and the TR-FRET signal was measured on the EnVision Multilabel Plate Reader (Perkin Elmer) (excitation at 320 nm, emission at 615 and 665 nm). The data was analyzed using GraphPad Prism 5 (La Jolla, Calif.).

BACE1, BACE2 and Cathepsin D Activity Assay Using Microfluidic Capillary Electrophoresis (MCE).

BACE1, BACE2, and Cathepsin D reactions were carried out in a final volume of 20 µl per well in a 384-well microplate using a Caliper LabChip 3000 (Hopkinton, Mass.). A standard enzymatic reaction, initiated by the addition of 10 µl 2× substrate to 5 µl of 4× enzyme and 5 µl of 4× peptide or small molecule inhibitor, contained 12 nM rhBACE1, 1 µM FAM-KTEEISEVNLDAEFRWKK-amide (SEQ ID NO: 20), 50 mM NaOAc, pH 4.4, 0.1% CHAPS. The same reaction conditions were used for rhBACE2 (5 nM) and Cathepsin D (6 nM) (Cat. No. 219394; EMD Biosciences, San Diego, Calif.). After incubation for 60 min at room temperature, the product and substrate in each reaction were separated using a 12-sipper microfluidic chip. Separation of product and substrate was optimized by choosing voltages and pressure using the Caliper Optimizer software. The separation buffer contained 100 mM HEPES, pH 7.2, 0.015% Brij-35, 0.1% Coating Reagent #3, 10 mM EDTA and 5% DMSO. The separation conditions used a downstream voltage of −500 V, an upstream voltage of −2250 V, and a screening pressure of −1.2 psi. The product and substrate fluorescence was excited at 488 nm and detected at 530 nm. Substrate conversion was calculated from the electrophoregram using the Caliper HTS Well Analyzer software.

BACE1 Fluorescence Polarization Competition Binding Assay.

BACE1 binding assays were carried out in a final volume of 10 µL per well in black 384-well microplates (Proxiplate-Plus; Perkin Elmer, Waltham, Mass.). A standard binding reaction, initiated by the addition of 5 µL 2× enzyme to 2.5 µL of 4× binding probe and 2.5 ml of 4× inhibitor, contained 12 nM rhBACE1, 3 nM 5-TAMRA-NEESMYCRLL-GIGCG (SEQ ID NO: 16) (5-TAMRA-BACE020), 50 mM NaOAc, pH 4.4 with 0.1% CHAPS. The reaction was permitted to proceed towards equilibrium for 2 h at ambient temperature prior to fluorescence polarization measurement using Envision (Perkin Elmer). The parallel and perpendicular fluorescent emissions measured in each well at 595 nm (excitation 531 nm polarized light) were used to determine the milli-polarization level (mP) using the following formula: $mP=1000*(S-G*P)/(S+G*P)$ where S=parallel emission, P=perpendicular emission and G=0.65. The mP value in each well was plotted as a function of inhibitor concentration and the 50% inhibition ($IC_{50}$) values were determined using a nonlinear least squares fit of the data to a four parameter equation using Prism 5.0 software (GraphPad Software, San Diego, Calif.). 5-TAMRA-labeled BACE020 was purchased from American Peptide Company, Inc (Sunnyvale, Calif.) and solubilized in DMSO to 100 mM for storage.

$A\beta_{1-40}$ Assay in 293-hAPP Cells.

$A\beta_{1-40}$ production was measured in 293-HEK cells stably expressing wild-type human APP(695) complementary DNA (cDNA) (293-hAPP). Cells were seeded overnight at $3\times10^4$ cells per well in a 96-well plate. Fresh media [Dulbecco's modified Eagle's medium (DMEM)+10% fetal bovine serum (FBS)] containing various inhibitors were incubated with the 293-hAPP cells for 24 h. The cellular medium was harvested and assayed for the presence of $A\beta_{1-40}$ with an $A\beta_{1-40}$ HTRF assay (CisBio) according to the manufacturer's instructions. $A\beta_{1-40}$ values were normalized for cell viability, as determined with the CellTiter-Glo Luminescent Cell Viability Assay (Promega). Experiments were performed at least 3 times, and each point in each experiment was repeated in duplicate. Data was plotted with a 4-parameter nonlinear regression curve-fitting program (KaleidaGraph, Synergy Software).

Results

Selection of Peptides that Bind to BACE1 at an Exosite

Two types of phage-displayed naïve peptide libraries, Linear-lib and Cyclic-lib, were used to select the BACE1 ligands, initially using a plate sorting format. The initial panning identified a group of peptides with a conserved ΦPYFΦ motif that is similar to peptides derived from phage display as reported previously (FIG. 1A) (Kornacker, M. G. et al. (2005) *Biochemistry* 44: 11567-73). Selected peptides, BACE010 and BACE011, were synthesized and tested in a BACE1 HTRF activity assay. BACE010 is a very weak inhibitor of BACE1, whereas BACE011 is an activator of BACE1 (FIG. 1B). The binding of phage-displayed peptides BACE010 and BACE011 to BACE1 was competitive with peptide BMS1 (FIG. 1C), which was previously described as an exosite-binding peptide (Kornacker, M. G. et al. (2005) *Biochemistry* 44: 11567-73). The competitive binding as well as the similar sequence motif suggests that these peptides bind to the same exosite on BACE1.

Selection of Peptides that do not Bind to the BACE1 Exosite

In order to obtain peptides that did not bind to the exosite of BACE1, we carried out solution sorting of BACE1 with naïve libraries in presence of 100 µM of the exosite-binding peptide BACE010 (Ac-SGPYFIEYMSAV-NH$_2$) (SEQ ID NO: 21). After four rounds of solution panning using this competitive selection strategy, one peptide out of the cyclic peptide library, designated as BACE017, was identified as a peptide with a distinct sequence that also bound to BACE1 (FIG. 2).

To improve the affinity of BACE017, a soft randomized library was constructed using the BACE017 sequence as the parent. After four rounds of panning at increasing stringency, 31 peptides were identified that bind to BACE1 with a stronger spot phage ELISA signal than the parent, manifested by significant improvement of the signal/noise ratio by over 5-fold. The sequence alignment and the sequence logo of these peptides indicated that the major sequence difference from the parent is His 4 to Ser 4, which likely accounts for the affinity improvement (FIG. 2).

Figure 3A:
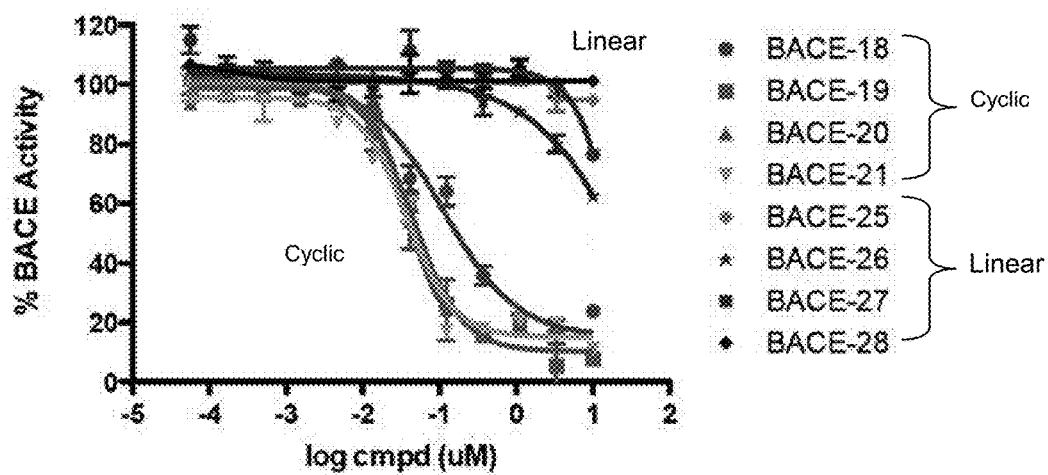
FIG. 3A shows the inhibitory activity of synthetic peptide ligands of BACE1 in an HTRF enzymatic assay. BACE1 binding peptides BACE018-BACE021 show a concentration-dependent inhibition in the cleavage of the 27-mer HTRF substrate for BACE1. Peptides corresponding to BACE018-BACE021 where the cysteine residues were substituted by serines (BACE025-BACE028) were much less effective in their ability to inhibit BACE1 enzymatic activity. BACE018-BAC021 and BACE025-BACE028 are identified in the figure as BACE-18-BACE-21 and BACE25-BACE-28, respectively.

Peptides Selectively Inhibit BACE1 Enzyme Activity and Compete with Active Site Binding Ligands Four cyclic peptides with a signal/noise ratio over 20 were selected for peptide synthesis, designated as BACE018-021, and subjected to two types of enzyme activity assays. BACE025-028 are peptides derived from BACE018-021, respectively, with Cys to Ser substitutions to explore the importance of the disulfide bond for their inhibitory activity. In HTRF enzyme activity assays (FIG. 3A), BACE018-021 peptides inhibited enzyme activity with $IC_{50}$ values of 10-70 nM, having up to 100-fold improvement in potency compared to BACE017. Linear versions of these peptides, BACE025-028, no longer inhibited BACE1 activity, indicating that the disulfide bond is essential for inhibition (Table 2). BACE020 is the peptide with the best inhibitory activity as indicated by HTRF enzyme activity assay and was selected for further studies.

Competition binding ELISA experiments were carried out using biotinylated BACE020 and a concentration dependent addition of BACE020, 0M99-2 or BMS1 peptides. As expected, there was no competition of biotinylated BACE020 with an exosite-binding peptide ligand BMS1

Figure 3B:
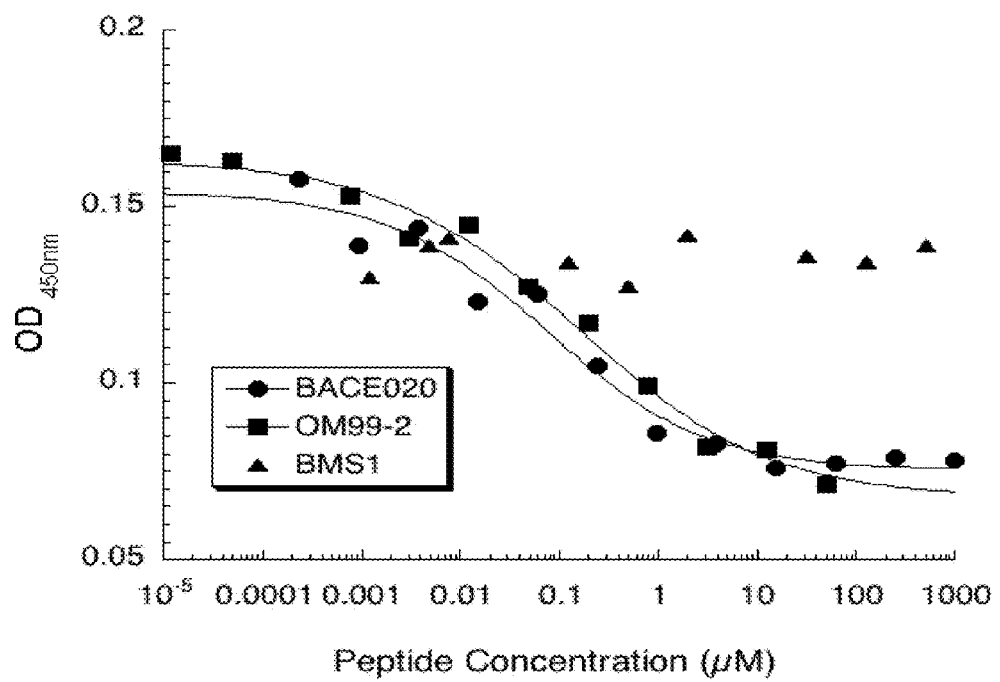
FIG. 3B is a graph showing the results of a biotinylated BACE020 competition binding ELISA with BACE020, and small molecule and peptide inhibitors OM99-2 or BMS1, respectively.

(FIG. 3B). However, the peptidic inhibitor OM99-2 that binds at the active site did compete for binding of biotinylated BACE020, suggesting that BACE020 also binds at the active site.

The affinities of BACE1 peptide ligands were measured using the abovementioned competition binding FP assay for determining $IC_{50}$ values with serially diluted peptides. A Caliper assay was used to measure the inhibition of BACE1 enzymatic activity by peptide ligands. As shown in Table 2, the affinities measured by the FP assay correlated with the inhibitory activity measured by the Caliper assay. Furthermore, the $IC_{50}$ values measured by the Caliper assay for peptides BACE017-021 and BACE025-028 are consistent with those measured by the HTRF assay.

To investigate the structure-activity relationship, we synthesized a panel of peptides with an alanine substitution at each position, as well as truncated peptides from the N-terminus of BACE020. Both the FP binding and Caliper activity assays were used to evaluate the affinity and inhibitory activity for these peptides (Table 2). Replacement of Asp1, Glu2, Gly11, Ile12, Gly13 and Gly15 with Ala, as well as truncation of Asp1 and Gly2, did not perturb the affinity or inhibitory activity of BACE020, indicating that these residues do not contribute much if any interaction energy. The Glu3 to Ala mutation, as well as the truncation up to position 4 (BACE031) weakened the affinity and inhibitory activity by 3-4 fold, and replacements of Tyr6 and Leu10 with Ala had similar losses in affinity, indicating that these residues moderately contribute to binding energy. The most dramatic reductions in peptide activity were observed when Arg8, Leu9, Ser4 and Met5 were replaced by alanine. In particular, the Arg8 to Ala mutant was completely inactive in competition binding and enzymatic assays. Replacing Arg8 with arginine analogues lysine, ornithine and citrulline (BACE058-060, respectively) rescued the peptide activity to some extent but could not restore full activity. BACE030 is the minimal version of the inhibitory peptide ligand with full activity and was used to obtain the crystal structure of the peptide-BACE1 complex (see Example 4). Inhibition of BACE1 by BACE030 was specific as there was no inhibition of the closely related aspartic acid proteolytic enzymes BACE2 or Cathepsin D.

TABLE 2

Inhibition activity and binding affinity of peptide ligands (SEQ ID NOS 22-24, 21, 25-26, 14-17, 27-31, 19, 18 and 32-53, respectively, in order of appearance) of human BACE1 determined by FP competition binding, assay Caliper BACE1 activity assay and HTRF BACE1 activity assay.

| Peptide | N | 1 | 2 | 3 | 4 | 5 | 6 | 7 | 8 | 9 | 10 | 11 | 12 | 13 | 14 | 15 | 16 | C | FP IC50 (µM) | Caliper IC50 (µM) | HTRF IC50 (µM) |
|---|---|---|---|---|---|---|---|---|---|---|---|---|---|---|---|---|---|---|---|---|---|
| BMS1 | Ac | | | | N | L | T | T | Y | P | Y | F | I | P | L | | P | NH2 | >10 | 0.227 ± 0.159 * | |
| BMS2 | Ac | | | | | A | L | Y | P | Y | F | L | P | I | S | A | K | NH2 | >10 | 26.414 ± 43.544 * | |
| BMS4 | Ac | | | | | | | Y | P | Y | F | I | P | L | | | | NH2 | >10 | 1.758 ± 1.260 * | |
| BACE010 | Ac | | | | | | S | G | P | Y | F | I | E | Y | M | S | A | V NH2 | >10 | 2.196 ± 1.644 * | |
| BACE011 | Ac | S | G | C | L | D | Y | P | C | F | V | P | I | S | | | | NH2 | | | |
| BACE017 | Ac | N | E | E | H | I | Y | C | R | L | L | G | L | G | C | G | | NH2 | >10 | >10 | 0.438 |
| BACE018 | Ac | K | E | E | S | I | Y | C | R | L | M | G | L | G | C | G | | NH2 | 0.102 ± 0.029 | 0.054 ± 0.021 | 0.077 |
| BACE019 | Ac | N | E | L | S | P | Y | C | R | L | M | G | L | G | C | D | | NH2 | 0.010 ± 0.003 | 0.015 ± 0.006 | 0.010 |
| BACE020 | Ac | N | E | E | S | M | Y | C | R | L | L | G | I | G | C | G | | NH2 | 0.011 ± 0.002 | 0.011 ± 0.003 | 0.012 |
| BACE021 | Ac | P | E | E | S | L | Y | C | R | L | L | A | L | G | C | G | | NH2 | 0.025 ± 0.000 | 0.017 ± 0.004 | 0.022 |
| BACE025 | Ac | K | E | E | S | I | Y | S | R | L | M | G | L | G | S | G | | NH2 | 10 ± 0 | 10 ± 0 | n.d. |
| BACE026 | Ac | N | E | L | S | P | Y | S | R | L | M | G | L | G | S | D | | NH2 | 13.1 ± 01.4 | 3.893 ± 3.011 | n.d. |
| BACE027 | Ac | N | E | E | S | M | Y | S | R | L | L | G | I | G | S | G | | NH2 | >10 | >10 | n.d. |
| BACE028 | Ac | P | E | E | S | L | Y | S | R | L | L | A | L | G | S | G | | NH2 | >10 | >10 | n.d. |
| BACE029 | Ac | | E | E | S | M | Y | C | R | L | L | G | I | G | C | G | | NH2 | 0.012 ± 0.000 | 0.013 ± 0.008 | |
| BACE030 | Ac | | | E | S | M | Y | C | R | L | L | G | I | G | C | G | | NH2 | 0.023 ± 0.005 | 0.018 ± 0.007 | |
| BACE031 | Ac | | | | S | M | Y | C | R | L | L | G | I | G | C | G | | NH2 | 2.6 ± 1.6 | 1.278 ± 1.188 | |
| BACE032 | Ac | | | | | M | Y | C | R | L | L | G | I | G | C | G | | NH2 | >10 | 8.089 ± 3.309 | |
| BACE033 | Ac | | | | | | Y | C | R | L | L | G | I | G | C | G | | NH2 | >10 | 10.910 ± 1.576 | |
| BACE034 | Ac | | | | | | | C | R | L | L | G | I | G | C | G | | NH2 | >10 | | |
| BACE042 | Ac | A | E | E | S | M | Y | C | R | L | L | G | I | G | C | G | | NH2 | 0.031 ± 0.011 | 0.012 ± 0.008 | |
| BACE043 | Ac | N | A | E | S | M | Y | C | R | L | L | G | I | G | C | G | | NH2 | 0.041 ± 0.009 | 0.013 ± 0.002 | |

TABLE 2-continued

Inhibition activity and binding affinity of peptide ligands (SEQ ID NOS 22-24, 21, 25-26, 14-17, 27-31, 19, 18 and 32-53, respectively, in order of appearance) of human BACE1 determined by FP competition binding, assay Caliper BACE1 activity assay and HTRF BACE1 activity assay.

| Peptide | | | | | | | | Peptide Sequence | | | | | | | | | | | FP IC50 (µM) | Caliper IC50 (µM) | HTRF IC50 (µM) |
|---|---|---|---|---|---|---|---|---|---|---|---|---|---|---|---|---|---|---|---|---|---|
| | N | 1 | 2 | 3 | 4 | 5 | 6 | 7 | 8 | 9 | 10 | 11 | 12 | 13 | 14 | 15 | 16 | C | | | |
| BACE044 | Ac | N | E | A | S | M | Y | C | R | L | L | G | I | G | C | G | | NH2 | 0.131 ± 0.010 | 0.046 ± 0.033 | |
| BACE045 | Ac | N | E | E | A | M | Y | C | R | L | L | G | I | G | C | G | | NH2 | 2.342 ± 0.877 | 0.304 ± 0.111 | |
| BACE046 | Ac | N | E | E | S | A | Y | C | R | L | L | G | I | G | C | G | | NH2 | 1.570 ± 0.787 | 0.435 ± 0.484 | |
| BACE047 | Ac | N | E | E | S | M | A | C | R | L | L | G | I | G | C | G | | NH2 | 0.225 ± 0.074 | 0.093 ± 0.081 | |
| BACE048 | Ac | N | E | E | S | M | Y | C | A | L | L | G | I | G | C | G | | NH2 | >10 | >10 | |
| BACE049 | Ac | N | E | E | S | M | Y | C | R | A | L | G | I | G | C | G | | NH2 | 7.7 ± 1.0 | 1.383 ± 0.691 | |
| BACE050 | Ac | N | E | E | S | M | Y | C | R | L | A | G | I | G | C | G | | NH2 | 0.186 ± 0.027 | 0.049 ± 0.027 | |
| BACE051 | Ac | N | E | E | S | M | Y | C | R | L | L | A | I | G | C | G | | NH2 | 0.036 ± 0.011 | 0.018 ± 0.005 | |
| BACE052 | Ac | N | E | E | S | M | Y | C | R | L | L | G | A | G | C | G | | NH2 | 0.039 ± 0.003 | 0.014 ± 0.004 | |
| BACE053 | Ac | N | E | E | S | M | Y | C | R | L | L | G | I | A | C | G | | NH2 | 0.037 ± 0.010 | 0.007 ± 0.000 | |
| BACE054 | Ac | N | E | E | S | M | Y | C | R | L | L | G | I | G | C | A | | NH2 | 0.012 ± 0.003 | 0.007 ± 0.004 | |
| BACE055 | Ac | N | E | E | S | M | F | C | R | L | L | G | I | G | C | G | | NH2 | 0.027 ± 0.007 | 0.011 ± 0.002 | |
| BACE056 | Ac | N | E | E | H | M | Y | C | R | L | L | G | I | G | C | G | | NH2 | 4.5 ± 2.3 | 3.575 ± 3.646 | |
| BACE057 | Ac | | | E | S | M | Y | C | A | L | L | G | I | G | C | G | | NH2 | >10 | >10 | |
| BACE058 | Ac | | | E | S | M | Y | C | K | L | L | G | I | G | C | G | | NH2 | 0.486 ± 0.171 | 0.074 ± 0.029 | |
| BACE059 | Ac | | | E | S | M | Y | C | X | L | L | G | I | G | C | G | | NH2 | # 0.512 ± 0.149 | 0.222 ± 0.210 | |
| BACE060 | Ac | | | E | S | M | Y | C | X | L | L | G | I | G | C | G | | NH2 | & 2.3 ± 0.4 | 0.772 ± 0.378 | |

Figure 4:
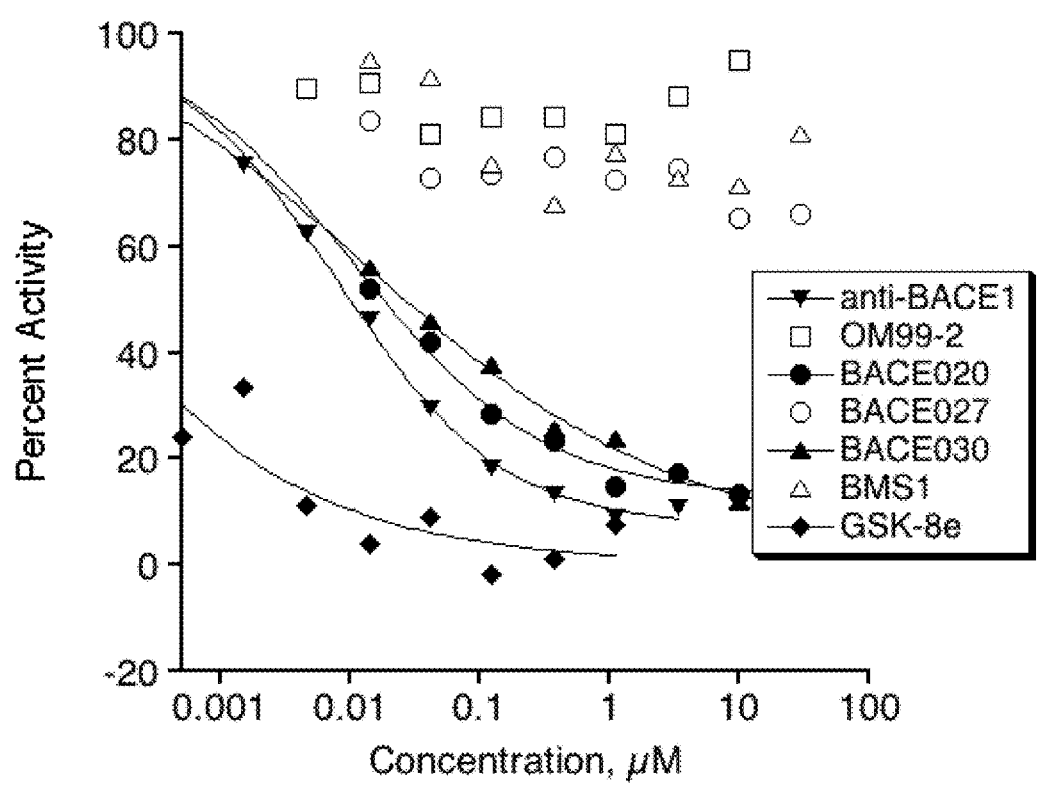
FIG. 4 is a graph showing that BACE1 binding peptides inhibit the production of Aβ in cellular assays. BACE1 binding peptides BACE017-BACE021 show a concentration-dependent reduction in Aβ production in 293-hAPP cells as compared to a BACE1 inhibitory antibody (anti-BACE1), a small molecule inhibitory of BACE1 (OM99-2), a peptide inhibitor of BACE1 (BMS1) and a small molecule inhibitor of BACE1 (GSK-8e, Charrier, et al., *J. Med. Chem.* 51: 3313-3317 (2008)). $IC_{50}$ values were determined using a 4-parameter nonlinear regression curve-fitting program.

\* rate increased, data is EC50 instead of IC50
\# X=L-ornithine
& X=L-citrulline BACE1 Peptide Inhibitors Reduce Aβ Production in Cell-Based Assays As peptides were potent inhibitors of in vitro BACE1 enzymatic activity, it was next determined if they were inhibitors of BACE1 in the context of a cellular environment that is more representative of the physiological state. Concentration dependent inhibition assays were performed using 293-HEK cells stably transfected with APP. BACE020 was indeed a potent inhibitor of the formation of Aβ production (FIG. 4). BACE030, which is truncated by two residues at the N-terminus, also showed potent inhibition (FIG. 4). BACE027, the linear Cys to Ser analog of BACE020, as well as the exosite binding peptide BMS1, showed no inhibition, in accord with the enzymatic results. However, not all enzymatic inhibitors showed cellular activity as evidenced by the potent active site binding peptidomimetic BACE1 inhibitor OM99-2 (FIG. 4). For completeness and comparison, cellular inhibition is also shown for the potent active site binding small molecule inhibitor GSK-8e (Charrier, et al., *J. Med. Chem.* 51: 3313-3317 (2008) and exosite binding anti-BACE1 antibody (FIG. 4) (Atwal, J. K. et al. (2011) *Sci Transl Med* 3: 84ra43).

Example 2

NMR Spectroscopy of BACE020 Solution Structure and Binding to BACE1

NMR Spectroscopy

BACE020 was dissolved in buffer containing 50 mM sodium phosphate pH 6.5 and 150 mM sodium chloride to a final concentration of 2 mM. For measurements in $D_2O$, the sample was lyophilized and redissolved in 100% $D_2O$. NMR spectra ($^1H$ 1D spectra, 2D-2QF COSY, 2D-TOCSY, and 2D-NOESY spectra) were acquired at 280K on a Bruker DRX800 spectrometer equipped with a room temperature triple-resonance probe. Spectra were processed with Topspin (Bruker), and spectral analysis was performed using the CCPN analysis software (Vranken, W. F. et al. (2005) *Proteins* 59: 687-96). The $^1H$ chemical shifts were assigned by standard methods (Wifihrich, K. (1986) NMR of proteins and nucleic acids. New York, Wiley). Distance restraints were derived from $^1H$ homonuclear two-dimensional NOESY spectra with 300 ms mixing time recorded in $H_2O$ and $D_2O$. Restraints for the backbone φ angles were derived from $^3J(H^N,H\alpha)$ coupling constants determined from high resolution 2QF-COSY spectra, with $\omega_2$ cross sections through $H^N$-Hα (Kim, Y. M. et al. (1989) *J Mag Res* 84:

9-13). $^3J(H\alpha,H\beta)$ coupling constants for $\chi_1$ angles were obtained from COSY-35 spectra measured in $D_2O$ (Cavanagh, J. (2007) Protein NMR spectroscopy: Principles and practice. Amsterdam; Boston, Academic Press).

For determining the binding site of BACE020 on the BACE1 protein, a sample of 30 μM fully $^2H/^{15}N$-labeled BACE1 was titrated with increasing amounts of BACE020 until a molar stoichiometry of 1:1.5 was reached. No further change in the recorded TROSY $^1H$, $^{15}N$ correlation spectra was observed beyond a molar stoichiometry of 1:1. For resonances tractable during the titration, the chemical shift perturbations were quantified using the weighted chemical shift change per residue $$\Delta\delta = [\Delta\delta_{H^N}{}^2 + (0.1\Delta\delta_N)^2]^{1/2}$$

where $Dd_HN$ and $Dd_N$ are the changes in chemical shift of $^1H^N$ and $^{15}N$, respectively.

NMR Structure Calculation

The experimentally determined distance and dihedral restraints for BACE020 (see Table 3) were applied in a simulated annealing protocol using ARIA2.2 (Rieping, W. et al. (2007) Bioinformatics 23: 381-2) and CNS (Brunger, A. T. et al. (1998) *Acta Crystallogr D Biol Crystallogr* 54: 905-21). Hydrogen restraints were not employed during the calculation. Structural quality was analyzed using PROCHECK (Laskowski, R. A. et al. (1996) *J Biomol NMR* 8: 477-86). Graphical representations were prepared with MOLMOL (Koradi, R. et al. (1996) *J Mol Graph* 14: 51-5, 29-32) and PyMOL (The PyMOL Molecular Graphics System, Version 1.3, Schrödinger, LLC).

TABLE 3

NMR Structural statistics for the solution structure of the BACE020 peptide

| Number of structural restraints | |
|---|---|
| NOE-derived distance restraints | |
| Total (unambiguous/ambiguous) | 553 (546/7) |
| intraresidual | 157 (157/0) |
| sequential | 129 (125/4) |
| medium range | 186 (183/3) |
| long range | 81 (81/0) |
| Dihedral restraints | |
| φ | 12 |
| $\chi_1$ | 3 |
| Violations | |
| R.m.s.d from experimental restraints | |
| NOE distance restraints (Å) | 0.0050 ± 0.0003 |
| Dihedral restraints (°) | 0.37 ± 0.05 |
| NOE distance violations | |
| Number > 0.1 Å | 0 |
| Dihedral violations | |
| Number > 2° | 0 |
| R.m.s.d. from idealized geometry | |
| Bonds (Å) | 0.00161 ± 0.00007 |
| Angles (°) | 0.375 ± 0.006 |
| Impr (°) | 0.24 ± 0.01 |
| Coordinate precision ¶ | |
| Backbone (residues 2-14) | 0.16 ± 0.04 |
| All heavy atoms (residues 2-14) | 0.49 ± 0.10 |

TABLE 3-continued

NMR Structural statistics for the solution structure of the BACE020 peptide

| Stereochemistry # | |
|---|---|
| Ramachandran plot (%) (all residues) | |
| Percentage in most favored regions | 77.3 ± 6.4 |
| Percentage in additionally allowed regions | 22.7 ± 6.4 |
| Energies (kcal mol$^{-1}$) ‡ | |
| $E_{NOE}$ | 0.69 ± 0.07 |
| $E_{CDIH}$ | 0.12 ± 0.02 |
| $E_{bond}$ | 0.57 ± 0.05 |
| $E_{angles}$ | 8.4 ± 0.3 |
| $E_{impr}$ | 0.97 ± 0.09 |

Statistics are reported on the ensemble of the ten lowest energy solution structures of BACE020 (out of 100 calculated). The CNS $E_{repel}$ function was used to simulate van der Waals interactions with an energy constant of 25.0 kcal mol$^{-1}$Å$^{-4}$ using 'PROLSQ' van der Waals radii.
1 kcal = 4.18 kJ.
¶ Coordinate precision is given as the Cartesian coordinate r.m.s.d. of the ten lowest-energy structures in the NMR ensemble with respect to their mean structure.
Structural quality was analyzed using PROCHECK (Laskowski, R. A. et al. (1996) *J Biomol NMR* 8: 477-86).
‡ NOESY derived distance restraints were used with a soft square-well potential using an energy constant of 50 kcal mol$^{-1}$ Å$^{-2}$. Dihedral angle restraints were applied using an energy constant of 200 kcal mol$^{-1}$ rad$^{-2}$. The force constants were 1000 kcal mol$^{-1}$ Å$^{-2}$ for bond length and 500 kcal mol$^{-1}$ rad$^{-2}$ for angles and improper dihedrals.

NMR Analysis of BACE020 Reveals its Solution Structure

Figure 5A:
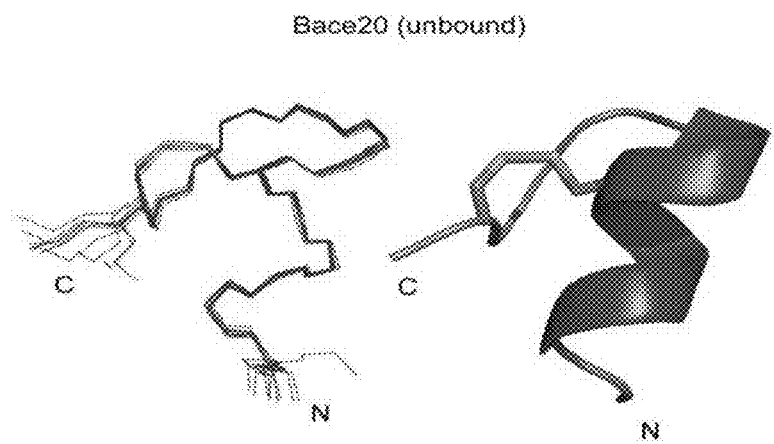
FIG. 5A shows the structure of BACE020 in solution as determined by homonuclear NMR spectroscopy.

Analysis of $^1H$ NMR spectra of BACE020 indicated that BACE020 has a defined structure in solution. Based on this initial assessment, the structure of BACE020 was solved by homonuclear NMR spectroscopy (FIG. 5A). The polypeptide is well defined between Glu3 and Cys14. Residues Glu3 through Leu10 form an N-terminal helix, which is connected to the C-terminus by a disulfide bond between Cys7 and Cys14. The side chains of Tyr6, Leu9, Leu10 and Ile12 form a hydrophobic cluster on one side of the structure. The disulfide bond is critical, as substitution of the cysteine to serine residues (BACE027) results in a loss of both structure and activity.

Mapping of the Binding Site of BACE020 on BACE1

Figure 5B:
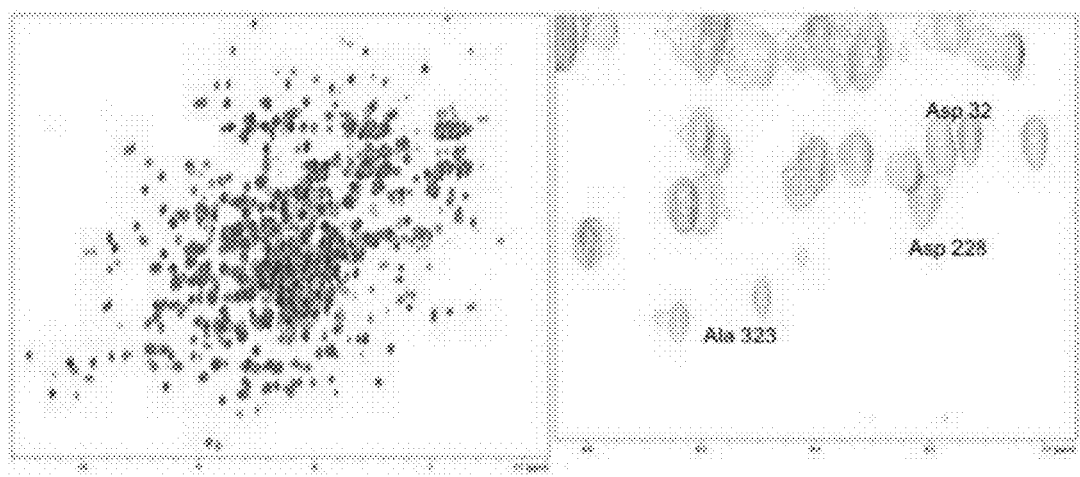
FIG. 5B shows a comparison of the TROSY spectra of unbound BACE1 (blue) compared to BACE1 in complex with BACE020 (red). The right panel highlights changes in the spectra of particular residues including the active site residues Asp 32 and Asp 228.
Figure 5C:
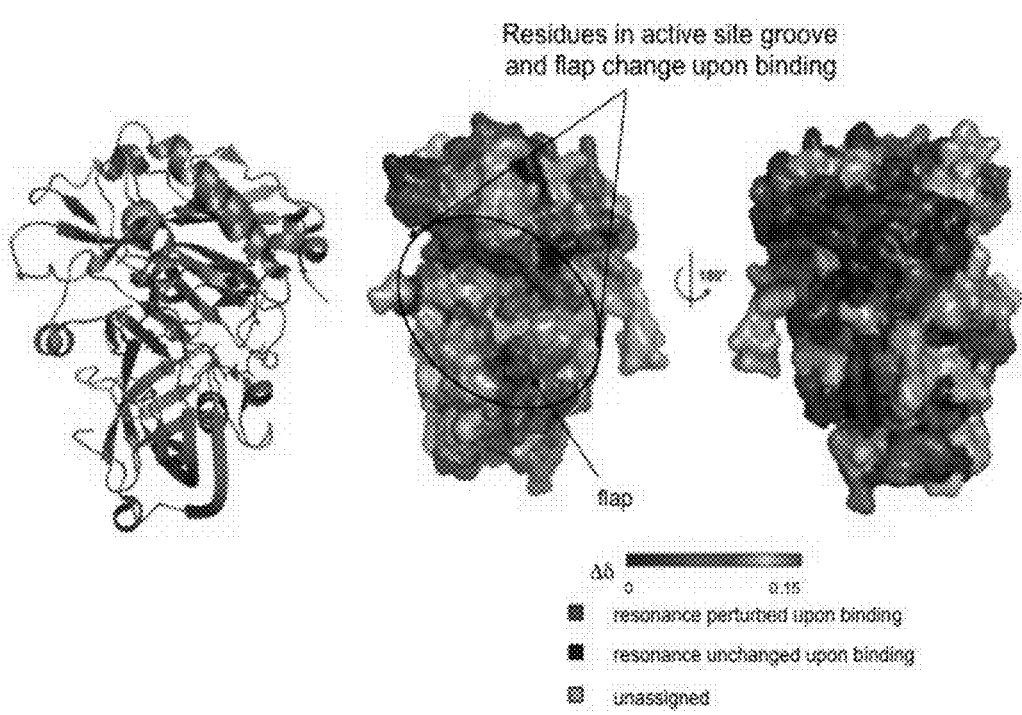
FIG. 5C depicts the structure of BACE1 in the active site groove and flap of BACE1; those BACE1 residues having perturbed resonances upon binding of BACE020 are shown in red.
Figure 6A:
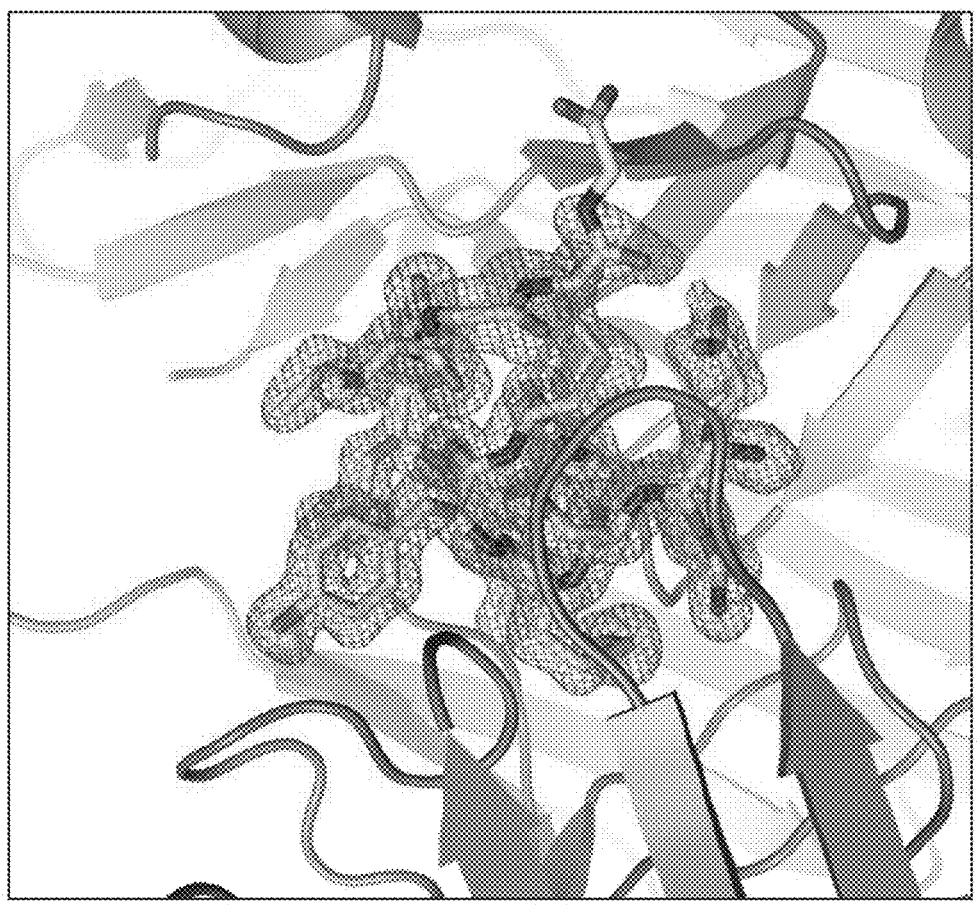
FIGS. 6A-E depicts the crystal structure at 1.5 Å resolution of BACE1 in complex with BACE030.
Figure 6B:
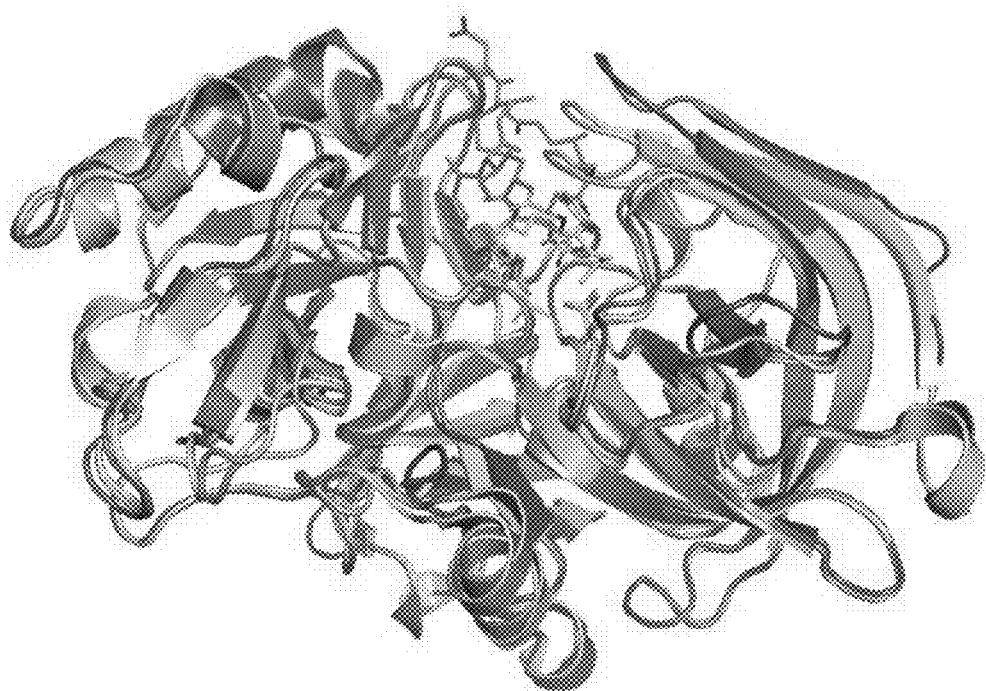
Figure 6C:
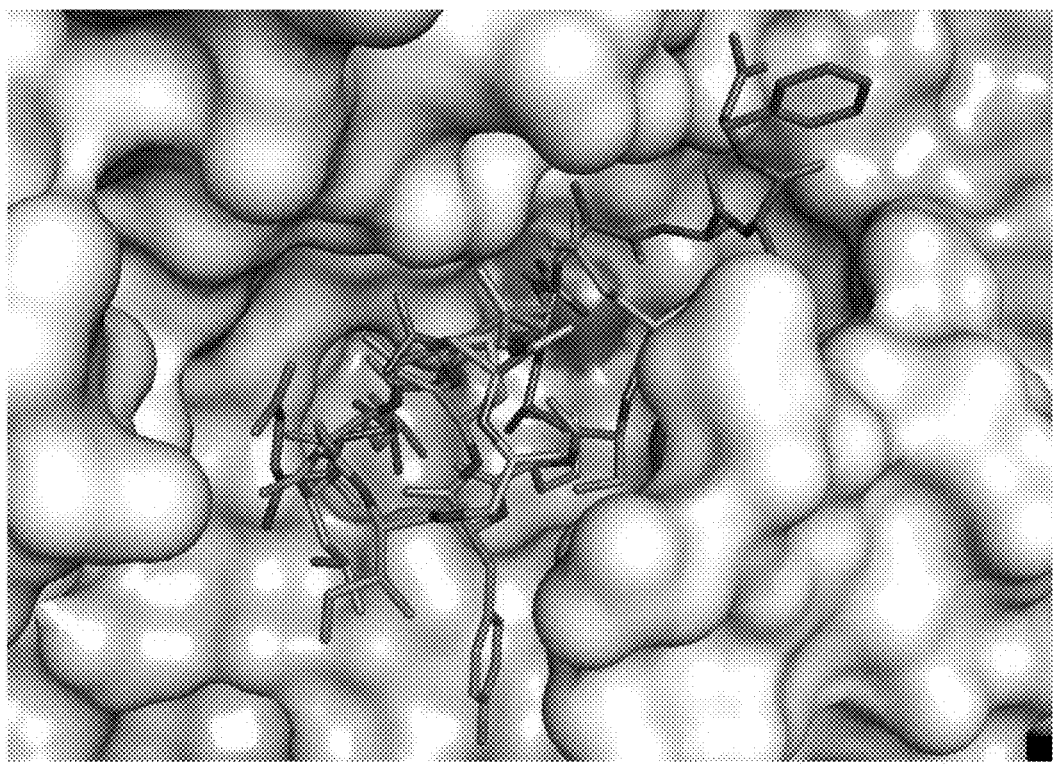
Figure 6D:
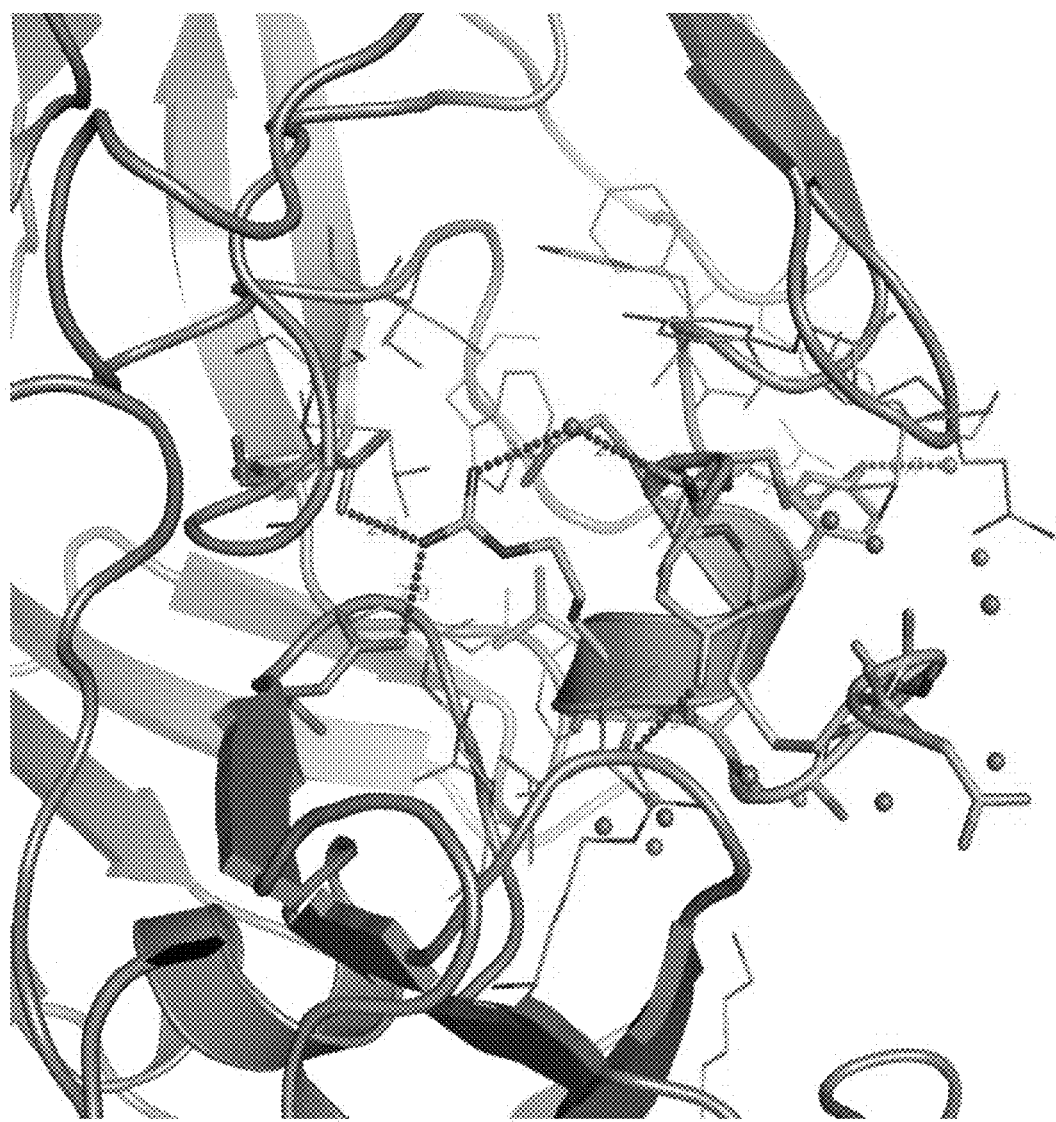
Figure 6E:
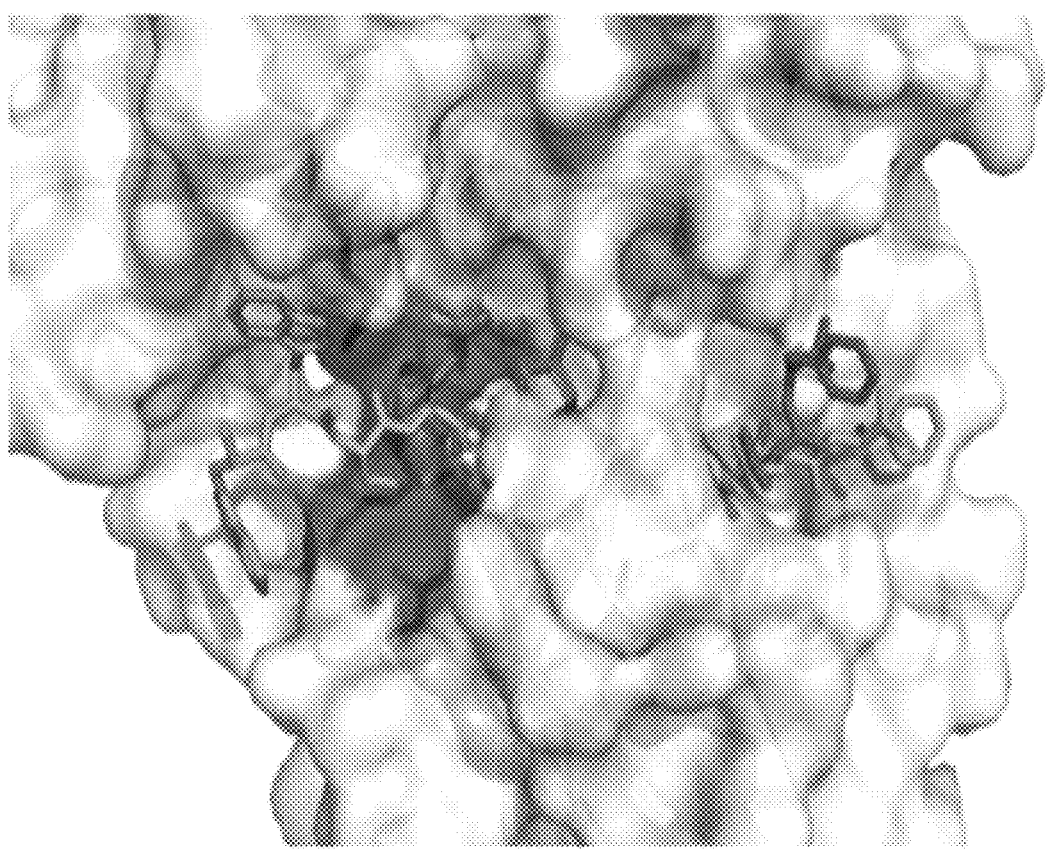

In order to determine the location of the binding site of BACE020 on BACE1, a titration experiment was performed by NMR spectroscopy, employing fully $^2H/^{15}N$ labeled BACE1. The construct of BACE1 (residues 43-453) used for this is very similar to the construct for which chemical shift assignments were published, which allowed the transfer almost all the assignments and follow chemical shift perturbations on a per-residue level (Liu, D. et al. (2004) *J Biomol NMR* 29: 425-6). Upon the addition of BACE020 to BACE1, a number of resonances of the unbound BACE1 disappeared gradually and new signals emerged at different locations in the spectrum. The binding was therefore in the slow exchange regime on the NMR time scale, as expected for a high-affinity interaction. The TROSY spectra of unbound BACE1 was compared to that of BACE1 in complex with BACE020 (See FIG. 5B). For many resonances it was obvious which one in the bound state corresponds to the one in the free state based on proximity. BACE1 resonances that are clearly affected by binding of BACE020 but have unknown new positions were considered as a separate class, because the chemical shift perturbation could not be quantified. Changes induced by BACE020 were localized at the interface between the N- and C-terminal lobes surrounding the substrate-binding groove. (See FIG. 5C). Both catalytic aspartate residues experienced chemical shift perturbation (FIG. 5B), indicating that the binding site is in close proximity to the active site. In addition, many resonances of residues in the flap were affected by addition of BACE020, which further suggests that the peptide binds within the substrate-binding groove. The flap is known to be very sensitive to binding of different molecules at the active site and can adopt multiple conformations to accommodate various ligands.

Example 3

Mapping of the Peptide Binding Site by Site-Directed Mutagenesis of BACE1

Construction, Expression and Purification of Human BACE1 ECD Mutants

Human BACE1 mutants were made in a pRK vector containing the BACE 1 signal peptide followed by its extracellular domain (ECD) (residues 22-457) and a C-terminal $His_8$ tag (SEQ ID NO: 54). Mutations were made using the appropriate oligonucleotide using a QuikChange® II XL Site-Directed Mutagenesis kit (Agilent Technologies Stratagene Products, La Jolla, Calif.) and confirmed by DNA sequencing. Proteins were expressed transiently using Chinese hamster ovary cells growing in 1-liter fermenters and cultures were harvested after 2 weeks. Following centrifugation, mutant proteins from the medium were purified to homogeneity (>95% purity) by chromatography on Ni-NTA agarose (Qiagen, Valencia, Calif.). After washing with PBS containing 10 mM imidazole, proteins were eluted with PBS containing 200 mM imidazole and the eluate was pooled, concentrated using a Vivaspin 20 (Sartorius-stedim, Goettingen, Germany) and applied to a Superdex 200 10/300 GL column (GE Healthcare Bio-Sciences AB, Uppsala, Sweden) equilibrated in 20 mM HEPES pH 7.2, 150 mM NaCl. Protein peaks were collected, concentrated and protein concentration determined by $A_{280}$. Purified proteins showed the correct molecular mass by SDS-PAGE; the thick band observed was likely due to heterogeneous glycosylation.

Biotinylated BACE020 Peptide Binding Assay

Binding of biotinylated BACE020 to recombinant protein was determined by a 96-well plate assay. Maxisorp microtiter plates (Nalge Nunc International, Rochester, N.Y.) were coated overnight at 4° C. with 2 µg/ml BACE 1 mutant in 50 mM carbonate, pH 9.6. The coated wells were washed with buffer (PBS, 0.05% Polysorbate 20) and blocked with assay buffer (PBS, pH 7.4, 0.5% BSA, 0.05% Tween 20, 15 ppm Proclin) for 1 h at room temperature with gentle shaking. After blocking, various concentrations of C-terminal biotin tagged BACE020 peptide with a polyethylene glycol (PEG) spacer (Ac-NEESMYCRLLGIGCG-(PEG)$_3$-biotin (SEQ ID NO: 16); Ac-NEESMYCRLLGIGCG-CONH—CH$_2$—(CH$_2$—CH$_2$—O—)$_3$—(CH$_2$)$_3$—NH-biotin (SEQ ID NO: 16)) diluted in assay buffer were added and plates were incubated for 1 h with gentle shaking at room temperature. After washing, the amount of peptide bound to the plate was detected by the addition of Streptavidin-Horseradish Peroxidase Conjugate (GE Healthcare, Piscataway, N.J.) followed by the addition of TMB/H$_2$O$_2$ substrate (KPL, Gaithersburg, Md.). The reaction was quenched with 1 M phosphoric acid and the $A_{450}$ measured on a Molecular Devices SpectraMax Plus384 microplate reader. Concentrations to give half maximal effective concentration (EC$_{50}$) were determined using a 4-parameter non-linear regression curve-fitting program with Kaleidagraph (Synergy Software, Reading, Pa.). Competition binding experiements were carried out using a fixed amount of biotinylated BACE020 and a concentration dependent addition of peptide (e.g. BACE020, OM99-2 or BMS1). Concentrations to give half maximal inhibition concentration (IC$_{50}$) were determined using a 4-parameter non-linear regression curve-fitting program with Kaleidagraph.

Results

To confirm the active site as the region for peptide binding, mutants of BACE1 were made in the substrate-binding groove defined by OM99-2 binding (Hong, L. et al. (2000) *Science* 290: 150-3). The ability of biotinylated BACE020 to bind to BACE1 and mutants was determined using an ELISA assay. The fold decrease in binding affinity was determined as the relative EC$_{50}$ values of EC$_{50}$ (mut)/EC$_{50}$ (WT), which are listed in Table 3.

TABLE 4

Relative Biotinylated BACE020 binding to BACE1 mutants

| BACE1 Mutant | Fold Decrease in Binding EC50 (Mut)/EC50 (WT) |
|---|---|
| WT | 1.0 |
| G72A (11)* | 6.5 |
| Q73A (12) | 1.7 |
| G74A (13) | 488.0 |
| L91A (30) | 1.0 |
| D93A (32) | 568.0 |
| S96A (35) | 1.0 |
| Y132A (71) | 72.2 |
| T133A (72) | 1.1 |
| Q134A (73) | 1990.0 |
| K168A (107) | 1.0 |
| F169A (108) | 1.9 |
| I171A (110) | 1020.0 |
| W176A (115) | 690.0 |
| I179A (118) | 2.6 |
| R189A (128) | 2.7 |
| K285A (224) | 4.0 |
| D289A (228) | 2210.0 |
| G291A (230) | 0.8 |
| T292A (231) | 73.6 |
| T293A (232) | 349.0 |
| N294A (233) | 2.4 |
| R296A (235) | 70.9 |
| K382A (321) | 4.5 |
| T390A (329) | 0.9 |

*(represents residue number based on structural numbering)

Example 4

Structure Determination by X-Ray Crystallography of BACE030 in Complex with BACE1

BACE1 Protein Expression and Purification

Human BACE1$_{57-453}$ or BACE1$_{43-453}$ DNA with a C-terminal His$_6$ tag (SEQ ID NO: 55) was synthesized by Blue Heron, cloned into a pET29a(+) vector, and transformed into BL21(DE3) cells. Expression was performed at 37° C. for 4 h with 1 mM isopropyl 0-D-1-thiogalactopyranoside (IPTG) induction. Cells were lysed with microfluidizer and inclusion bodies containing BACE1 were isolated and washed twice with TE (10 mM Tris•HCl pH 8.0 and 1 mM ethylenediaminetetraacetic acid (EDTA)) buffer. Inclusion bodies were solubilized with 7.5 M urea, 100 mM AMPSO pH 10.8 and 100 mM β-mercaptoethanol (BME) at room temperature for 2 h before centrifugation at 12,000 rpm for 30 min. The supernatant was then diluted with 7.5 M urea, 100 mM AMPSO pH 10.8 to achieve $OD_{280}$~1.5-2.0. Refolding was performed by first diluting the solubilized BACE1 1:20 fold into cold water then gently stirring the sample at 4° C. for 3 weeks to allow the refolding reaction to take place. Purification of refolded BACE1 involved 3 column steps. The protein was first loaded onto a 50 ml Q sepharose Fast Flow (GE Healthcare) column pre-equilibrated with 20 mM Tris pH 8.0 with 0.4 M urea, and was eluted with a salt gradient of 0-0.5 M NaCl. Peak fractions were pooled, diluted 5-fold with 20 mM Tris pH 8.0 buffer, and loaded onto a Source™ 15Q column (GE Healthcare). A gradient of 0-0.3 M NaCl was deployed to elute BACE1. Fractions containing BACE1 protein were pooled, concentrated and purified further on a Superdex S75 column in 25 mM Hepes pH 7.5, 150 mM NaCl.

Crystallization of BACE030 in Complex with BACE1

Purified $BACE1_{57-453}$ was concentrated to 11 mg/ml in the same buffer as described above, and incubated with 1 mM of peptide BACE030 (originally dissolved at 100 mM in 100% DMSO) for 1 h at 4° C. Crystallization was then set up by mixing 0.2 μl of BACE1 protein stock solution with 0.2 μl of reservoir solution containing 20% PEG 3350 and 0.1 M Bis-Tris pH 5.5 at ambient temperature by the setting drop vapor diffusion method. Crystals appeared and grew to full size in 3 days. Crystals were looped out of the crystallization drop and quickly transferred into a cryoprotectant solution (mother liquor plus 20% glycerol) for a less than 1 min, and were then looped out of the cryoprotectant drop for flash freezing in liquid nitrogen.

Data Collection and Structure Determination

Diffraction data were collected using a monochromatic X-ray beam (0.9796 Å wavelength) at the Diamond Light Source (DLS) beam line 102. The crystal was maintained at cryogenic temperature throughout the data collection. The X-ray detection device was an ADSC quantum-315 CCD detector placed 170 mm away from the crystal. The rotation method was applied to a single crystal for collection of the complete data set, with 0.5° oscillation per frame and a total wedge size of 140°. Data was then indexed, integrated, and scaled using the program HKL2000 (Otwinowski, Z. et al. (1997) *Methods Enzymol.* 276: 307-325). Data processing statistics are shown in Table 5.

The structure was solved using the molecular replacement (MR) method with the program Phaser (McCoy, A. J. et al. (2007) *J Appl Crystallogr* 40: 658-674). Matthews' coefficient calculation results indicated that each asymmetric unit was composed of one BACE1/peptide complex and 50% solvent. Therefore, the MR calculation was directed to search for one set of three subunits of the BACE1 extracellular domain. The search model of BACE1 was from the BACE1 structure 1FKN (Hong, L. et al. (2000) *Science* 290: 150-3). Within the BACE1 active site, a large positive peak was observed in the difference electron density map due to the peptide structure. Significant conformational changes took place in BACE1, especially in the flap region. Manual rebuilding was done with the program COOT (Emsley, 2004). Structure refinement was carried out iteratively with the programs REFMACS (Murshudov, G. N. et al. (1997) *Acta Crystallogr D Biol Crystallogr* 53: 240-55) and PHENIX (Adams, 2010) using the maximum likelihood target functions, the anisotropic individual B-factor refinement method, and the TLS refinement method, to achieve a final R factor of 0.164 and Rfree of 0.194. Structure refinement statistics are shown in Table 5.

TABLE 5

Crystallography data statistics

| Data collection | |
|---|---|
| Space group | C 2 2 2$_1$ |
| Unit cell | a = 75.1Å, |
| | b = 104.6Å, |
| | c = 111.3Å, |
| | α = β = γ = 90° |
| Resolution | 30 – 1.5Å |
| Total number of reflections | 323359 |
| Completeness | 98.8% (90.7%)[2] |
| Redundancy | 5.1 (2.5) |
| I/σ | 23.6(2.3) |
| Rsym[1] | 0.065 (0.452) |
| Refinement | |
| Resolution range | 30 – 1.5Å |
| Rcryst[3]/Rfree[4] | 0.164/0.194 |
| Free R test set size | 5% of observed reflections |
| Non-hydrogen atoms | 3718 |
| Water molecules | 412 |
| Average B, Overall | 23.0 |
| Protein | 21.0 |
| Water | 38.41 |
| r.m.s.d bond lengths | 0.014Å |
| r.m.s.d..angles | 1.538° |

[1]Rsym = Σ|Ihi − Ih|/ΣIhi, where Ihi is the scaled intensity of the ith symmetry-related observation of reflection h and Ih is the mean value.
[2]Values in parentheses are of the highest resolution shell, which is (1.55 – 1.50Å)
[3]Rcryst = Σh|Foh − Fch|/ΣhFoh, where Foh and Fch are the observed and calculated structure factor amplitudes for reflection h.
[4]Value of Rfree is calculated for 5% randomly chosen reflections not included in the refinement.

Structural Basis of an Active Site Targeting Cyclic Peptide Inhibitor

Figure 7A:
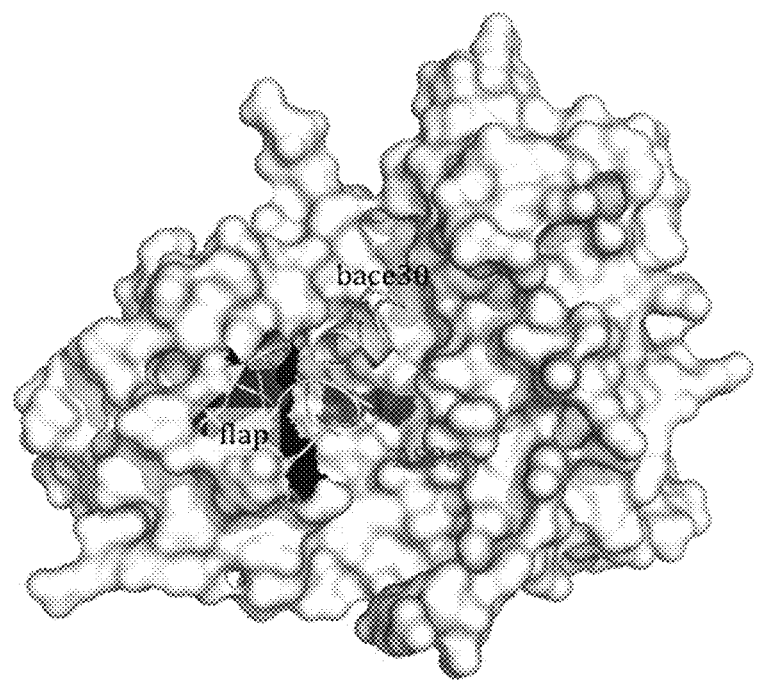
FIG. 7A depicts a distal view of the crystal structure at 1.5 Å resolution of the BACE030 peptide bound to the active site of BACE. BACE030 is shown in yellow, the region of BACE1 containing the catalytic aspartate residues is shown in red, and the flap region of BACE1 is shown as the backbone trace.
Figure 7B:
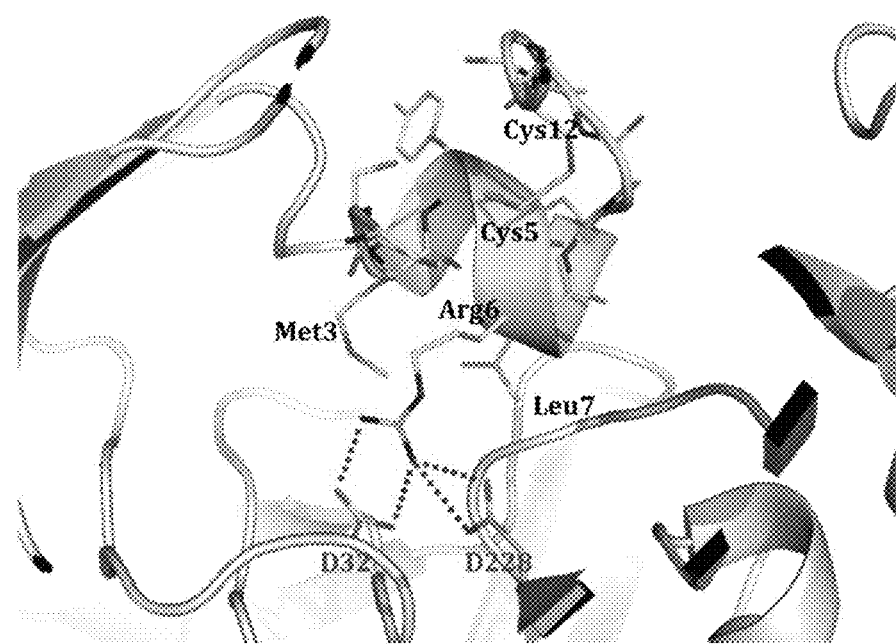
FIG. 7B depicts the interactions of the "arginine finger" (Arg6) of BACE030 with the catalytic aspartate residues of BACE1.
Figure 7C:
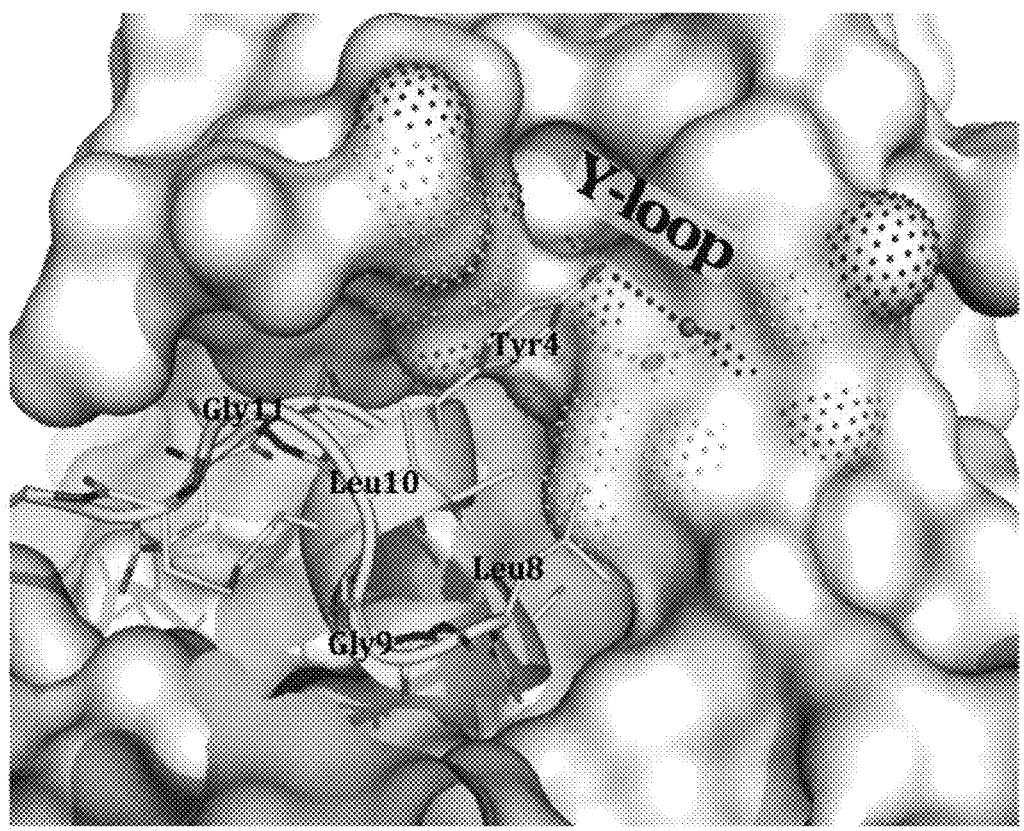
FIG. 7C depicts the interactions of Tyr4 of BACE030 with the Y-loop of BACE1.

To characterize the interactions between BACE030 peptide and BACE1 catalytic domain, the crystal structure of the binary complex was determined at 1.5 Å resolution. The peptide was incorporated by co-crystallization after futile trials of soaking the peptide into several known crystal forms. As shown in FIG. 7A, BACE030 binds to the catalytic groove, underneath a flexible loop segment of BACE1 commonly known as the flap region. The flap region can adopt various conformations as observed in the crystal structures of OM99-2 and small molecule inhibitors bound BACE1 (Hong, L. et al. (2000) *Science* 290: 150-3; Cole et al., (2008) *Bioinorganic Med. Chem. Lett.* 18:1063-1066; Patel et al., (2004) *J. Mol. Biol.* 343: 407-416). Upon BACE030 binding, the flap opens up by about 7 Å (based upon Cα of Thr72) compared to its closed position in the substrate bound conformation observed with the canonical linear substrate-like inhibitor OM99-2 (PDB accession code 1FKN) (Hong, L. et al. (2000) *Science* 290: 150-3) and accommodates the larger helical peptide. BACE030 in the bound state preserved the α-helical structure observed in solution by NMR (see Example 2). The disulfide linkage between Cys5 and Cys12 maintains such a secondary structure, underlining the absolute requirement for cysteine residues at these two positions. It supports the idea of using naïve cyclic phage library for screening, although the natural BACE1 substrates are linear and an α-helical peptide binding to the BACE1 active site seemed counterintuitive. The structure of the complex revealed features that were tightly correlated with the phage display results. Most of the peptide residues are involved in the binding interactions. The invariant Arg6, termed the "arginine finger", presents its side chain into the catalytic center and forms bidentate salt-bridges with the two catalytic aspartates (FIG. 7B). Such functionality closely resembles that of the "warhead" groups often seen in small molecule BACE1 inhibitors. Met3 and Leu7 of BACE030 pack against the hydrophobic pockets S1 and S3 sites on the BACE1 surface, respectively. The S1 site appears promiscuous and can tolerate various hydrophobic residues of similar size (e.g., Ile, Leu, Met, consistent with the peptide phage data), while the S3 site requires a Leu. Tyr4, another highly conserved residue in the peptide, binds to a small groove on BACE1 comprising residues 107-111 (Y-loop), a previously under-appreciated site for inhibitor binding. Given its proximity to the catalytic center, this site could potentially be targeted for small molecule inhibitor design. The Y-loop interactions are enhanced by the presence of Leu8, and in turn by the hydrophobic but less conserved residue Leu10 (FIG. 7C). Gly9 and Gly11 provide flexibility for Leu10 to pack onto the hydrophobic core. On the N-terminus of the peptide, the highly conserved Glu1 side chain forms a salt bridge with Arg 235 of BACE1. Ser2 places a cap to the N-terminus of the helix. Compared to the OM99-2 and OM03-4 non-hydrolyzable substrate mimics (Hong, L. et al. (2000) *Science* 290: 150-3; Turner, R. T., 3rd et al. (2005) *Biochemistry* 44: 105-12), BACE030 occupies the substrate groove on the P side (P1-P4), with peptide bonds tracing in the opposite direction from that of the substrate. BACE030 uses the "arginine finger" to bind to BACE1 at its catalytic aspartate residues, thus precluding any opportunity for presentation of a scissile peptide bond.

What is claimed is:

1. An isolated polynucleotide encoding a polypeptide comprising the amino acid sequence X1-S-X2-Y-C-R-L-X3-X4-X5-X6-C-(X7)$_n$ (SEQ ID NO: 6), wherein X1 is glutamic acid or aspartic acid: wherein X2 is methionine, leucine, isoleucine or valine; wherein X3 is leucine or methionine: wherein X4 is glycine, serine or alanine; wherein X5 is leucine, isoleucine or valine; wherein X6 is glycine or alanine; wherein X7 is glycine, aspartic acid or glutamic acid, and wherein n is 0 or 1, or a complement thereof.

2. A vector comprising the polynucleotide of claim 1.

3. A host cell comprising the vector of claim 2.

4. The polynucleotide of claim 1, wherein the encoded polypeptide comprises an amino acid sequence selected from the group consisting of KEESIYCRLMGLGCG (SEQ ID NO: 14), NELSPYCRLMGLGCD (SEQ ID NO: 15), NEESMYCRLLGIGCG (SEQ ID NO: 16) and PEESLYCRLLALGCG (SEQ ID NO: 17).

5. The polynucleotide of claim 1, wherein the encoded polypeptide comprises the amino acid sequence SMYCRLLGIGCG (SEQ ID NO: 18) (BACE031) or ESMYCRLLGIGCG (SEQ ID NO: 19) (BACE030).

6. The polynucleotide of claim 1, wherein the encoded polypeptide comprises a sequence having cysteines at positions −1 and −8 relative to the C terminus, an arginine or arginine analogue at position −7 relative to the C-terminus, and a leucine at position −6 relative to the C-terminus.

7. The polynucleotide of claim 6, wherein the encoded polypeptide further comprises small amino acids at positions 0, −2 and −4 relative to the C-terminus, or glycine at positions 0, −2 and −4 relative to the C-terminus, or a hydrophobic residue at position −3 relative to the C-terminus, or a leucine at −5 relative to the C-terminus, or a tyrosine or a phenylalanine at position −9 relative to the C-terminus, or a bulky hydrophobic residue at position −10 relative to the C-terminus, or a serine at position −11 relative to the C-terminus, or an acidic residue at position −12 relative to the C-terminus, or glutamic acid at position −12 relative to the C-terminus.

8. The polynucleotide of claim 6, wherein the encoded polypeptide comprises amino acids at positions 0, −2 and −4 that are small amino acids; wherein the amino acid at position −3 is a hydrophobic residue; wherein the amino acid at position −5 is leucine or methionine; wherein the amino acid at position −7 is arginine; wherein the amino acid at position −9 is tyrosine or phenylalanine; wherein the amino acid at position −10 is a bulky hydrophobic residue; wherein the amino acid at position −11 is serine; and wherein the amino acid at position −12 is an acidic amino acid.

9. The polynucleotide of claim 8, wherein the encoded polypeptide comprises amino acids at positions 0, −2 and −4 that are glycines; wherein the amino acid at position −3 is a hydrophobic residue; wherein the amino acid at position −5 is leucine; wherein the amino acid at position −7 is arginine; wherein the amino acid at position −9 is tyrosine; wherein the amino acid at position −10 is a bulky hydrophobic residue; wherein the amino acid at position −11 is serine; and wherein the amino acid at position −12 is glutamic acid.

10. The polynucleotide of claim 6, wherein the encoded polypeptide comprises a sequence selected from the sequences of BACE binding peptides set forth in Table 2 and FIG. 2.

11. The polynucleotide of claim 7, wherein the encoded polypeptide comprises a C terminal amino acid sequence selected from KEESIYCRLMGLGCG (SEQ ID NO: 14), NELSPYCRLMGLGCD (SEQ ID NO: 15), ESMYCRLLGIGCG (SEQ ID NO: 19) and PEESLYCRLLALGCG (SEQ ID NO: 17).

12. The polynucleotide of claim 1, wherein the encoded polypeptide is an inhibitor of BACE1 proteolytic activity.

\* \* \* \* \*